US012668582B2

(12) United States Patent
Ewin et al.

(10) Patent No.: US 12,668,582 B2
(45) Date of Patent: Jun. 30, 2026

(54) PHOSPHODIESTERASE 3 (PDE3) INHIBITORS

(71) Applicant: Zoetis Services LLC, Parsippany, NJ (US)

(72) Inventors: Richard A. Ewin, Kalamazoo, MI (US); Michael P. Curtis, Kalamazoo, MI (US); Todd M. Maddux, Kalamazoo, MI (US); Graham M. Kyne, Kalamazoo, MI (US)

(73) Assignee: Zoetis Services LLC, Parsippany, NJ (US)

( * ) Notice: Subject to any disclaimer, the term of this patent is extended or adjusted under 35 U.S.C. 154(b) by 316 days.

(21) Appl. No.: 18/598,312

(22) Filed: Mar. 7, 2024

(65) Prior Publication Data

US 2024/0308973 A1 Sep. 19, 2024

Related U.S. Application Data

(60) Provisional application No. 63/626,812, filed on Jan. 30, 2024, provisional application No. 63/489,441, filed on Mar. 10, 2023.

(51) Int. Cl.

| | |
|---|---|
| ***C07D 401/14*** | (2006.01) |
| ***A61K 31/433*** | (2006.01) |
| ***A61K 31/437*** | (2006.01) |
| ***A61K 31/4375*** | (2006.01) |
| ***A61K 31/501*** | (2006.01) |
| ***A61K 31/506*** | (2006.01) |
| ***A61K 31/549*** | (2006.01) |
| ***A61K 31/55*** | (2006.01) |
| ***A61K 45/06*** | (2006.01) |
| ***A61P 9/00*** | (2006.01) |
| ***C07D 401/04*** | (2006.01) |
| ***C07D 403/04*** | (2006.01) |
| ***C07D 403/14*** | (2006.01) |
| ***C07D 417/04*** | (2006.01) |
| ***C07D 417/14*** | (2006.01) |
| ***C07D 471/04*** | (2006.01) |

(52) U.S. Cl.

CPC .......... *C07D 401/04* (2013.01); *A61K 31/433* (2013.01); *A61K 31/437* (2013.01); *A61K 31/4375* (2013.01); *A61K 31/501* (2013.01); *A61K 31/506* (2013.01); *A61K 31/549* (2013.01); *A61K 31/55* (2013.01); *A61K 45/06* (2013.01); *C07D 401/14* (2013.01); *C07D 403/04* (2013.01); *C07D 417/04* (2013.01); *C07D 417/14* (2013.01); *C07D 471/04* (2013.01)

(58) Field of Classification Search

CPC .. C07D 401/04; C07D 401/14; C07D 403/04; C07D 417/04; C07D 417/14; C07D 471/04; A61K 31/433; A61K 31/437; A61K 31/4375; A61K 31/501; A61K 31/506; A61K 31/549; A61K 31/55; A61K 45/06

See application file for complete search history.

(56) References Cited

U.S. PATENT DOCUMENTS

| | | | |
|---|---|---|---|
| 4,361,563 | A | 11/1982 | Austel et al. |
| 4,562,190 | A | 12/1985 | Ueda et al. |
| 4,591,591 | A | 5/1986 | Robertson |
| 4,617,302 | A | 10/1986 | Robertson |
| 4,647,564 | A | 3/1987 | Robertson |
| 4,916,128 | A | 4/1990 | Jonas et al. |
| 4,933,336 | A | 6/1990 | Martin et al. |
| 7,282,511 | B2 | 10/2007 | Gronborg et al. |
| 2007/0112010 | A1 | 5/2007 | Kleeman et al. |

FOREIGN PATENT DOCUMENTS

EP 0 381 374 A1 8/1990

OTHER PUBLICATIONS

Combs, D.W., et al., "Heteroatom analogues of Bemoradan: Chemistry and Cardiotonic Activity of 1,4-benzothiazinylpyridazinones. Journal of Medicinal Chemistry;" vol. 35, 1992, pp. 172-176.

Van Der Mey, M., et al., "Synthesis and Structure-Activity Relationships of cis-Tetrahydrophthalazinone/Pyridazinone Hybrids: A Novel Series of Potent Dual PDE3/PDE4 Inibitory Agents. Journal of Medicinal Chemistry," vol. 46, 2003; pp. 2008-2016.

Marie-Claire Forest, et al., "A Novel Class of Cardiotonic Agents: Synthesis and Biological Evaluation of 5-Substituted 3,6-Dihydrothiadiazin-2-ones with Cyclic AMP Phosphodiesterase Inhibiting and Myofibrillar Calcium Sensitizing Properties," Journal of Medicinal Chemistry, 1992, vol. 35, pp. 163-172.

G. Nadler, et al., "Stereospecificity of myofibrillar calcium sensitivity and PDE inhibition in cardiotonic thiadiazinones," European Journal of Medicinal Chemistry (1996), vol. 31, pp. 805-812.

*Primary Examiner* — Rayna Rodriguez
*Assistant Examiner* — Aaron Rafanan Ullman
(74) *Attorney, Agent, or Firm* — Paul M. Misiak

(57) ABSTRACT

The invention describes novel PDE3 inhibitors for treating a cardiovascular disease including myxomatous mitral valve disease, congestive heart failure and/or asymptomatic heart failure in animals, particularly canines.

20 Claims, No Drawings

PHOSPHODIESTERASE 3 (PDE3) INHIBITORS

FIELD OF THE INVENTION

The present invention describes novel multi-modal cardiotonic agents that inhibit phosphodiesterase 3 (PDE3) and lower arrhythmia potential from calcium sensitization; processes for the preparation thereof, compositions thereof and methods of use for the treatment of a cardiovascular disease including myxomatous mitral valve disease, congestive heart failure and/or asymptomatic heart failure in animals.

BACKGROUND

Congestive heart failure (CHF) is a major cause of death in patients with heart disease. Phosphodiesterases are a class of intracellular enzymes responsible for the hydrolysis of cyclic adenosine monophosphate (c-AMP) and cyclic guanosine monophosphate (c-GMP) which are involved in the regulation of important cell functions, such as secretion, contraction, metabolism and growth. On the basis of structure, and substrate specificity, PDE enzymes can be grouped into eleven different families defined as PDE1 through PDE11.

Each PDE isozyme has a conserved C-terminal catalytic domain and unique N-terminal regulatory domain. These isozymes are found in different tissues and cells of animals such as smooth muscle, brain, heart, lung, platelets, lymphocytes and others. Among all subtypes of PDE, PDE3 is predominantly expressed in heart muscle and platelets. The PDE3 family in mammals consists of two isoforms (A and B) that have similar pharmacological properties but can be distinguished based on their expression profiles and affinity for cGMP. PDE3A exists in platelets, kidney, vascular smooth muscle, heart and oocytes. PDE3B is localized in adipocytes, hepatocytes, vascular smooth muscle, developing sperm, kidney, B cells, T-lymphocytes and macrophages. PDE3 is specific for c-AMP and has no effect on c-GMP or calmodulin. Therefore, inhibition of PDE3 isoenzyme in cardiovascular tissues leads to high levels of c-AMP and consequent inotropic effects thereby driving cardiac muscle contraction (inotropy) and smooth muscle vasodilation.

Myxomatous mitral valve disease (MMVD) is the leading cause of cardiovascular disease in dogs. MMVD causes incompetence of the mitral valve leading to mitral regurgitation which promotes sodium and water retention, activation of neurohormonal systems, volume overload, and eventual congestive heart failure (CHF). Synonymous MMVD medical terms used herein, include mitral valve disease (MVD), degenerative mitral valve disease (DMVD); chronic valve disease (CVD); chronic valvular heart disease (CVHD); and atrial ventricular valvular insufficiency (AVVI). The pathology of MMVD involves the differentiation and activation of the normally quiescent mitral valve into a more active myofibroblast phenotype, which mediates many of the histological and molecular changes in the valve tissue. MMVD is present in approximately 30% of all dogs over the age of 10 years and is the most frequent cause of CHF in dogs. MMVD is most prevalent in small dogs such as the Cavalier King Charles Spaniel, Chihuahua, Maltese, Pekinese, toy and miniature poodles. The natural history of the disease is one of adult onset, variable progression with aging, and eventual development of CHF in dogs with severe disease. Current treatments for MMVD includes the use of angiotensin enzyme inhibitors, diuretics, vasodilators, and positive inotropes.

Earlier (1985-1988) citations describe benzothiazolones (U.S. Pat. No. 4,562,190A), thiadiazinones (U.S. Pat. No. 4,916,128A) and pyridazinones (U.S. Pat. No. 4,647,564A) as agents with properties useful as anti-hypertensives, antithrombotics, cardiotonics and positive inotropes that can be used to treat cardiac insufficiency. PDE3 inhibitory data was not presented in these earlier citations. Additionally, a number of non-spirocyclic cardiotonic agents were described in the Journal of Medicinal Chemistry (JMC), Vol. 35, 1992, pp. 163-172; that had PDE3 $IC_{50}$ values ranging from about 0.17-66.0 μM (Table IX) with a reported pimobendan $IC_{50}$ of 0.56 μM (560 nM). According to the JMC citation, small changes in molecular structure can have very different effects on enzyme (PDE and ATPase) inhibition and/or calcium sensitizing properties. For example, it was shown that indolidan with a PDE3 $IC_{50}$ value of 0.52 μM lacked calcium-sensitizing properties and that the introduction of the sulfur atom into the pyridazine ring favored the desired activity and that substitution of the indolone moiety also appeared essential. This was demonstrated in Table IV with the alkyl substitutions on the indole ring. According to the JMC, the addition of a sulfur-containing spirocyclic ring to the indole increased calcium-sensitizing activity 30-fold, but was less potent as an inotropic agent in-vivo. Therefore, it was taught that the requirements for achieving calcium-sensitizing effects were 1) the indolone and heterocyclic parts of the molecule must be able to achieve a relative co-planarity, 2) the heterocyclic part must contain a sulfur (or selenium) atom, and 3) substituents (preferably bulky groups) are required at the 3-position of the indoline ring. In contrast, we have shown that the S-atom and/or bulky groups are not required to attain this dual activity. Further, it was found that the addition of a halogen atom at the 7-position of an oxindole-containing molecule can induce calcium sensitizing properties and/or increase PDE3 inhibition. As such, the compounds of the invention have the desired PDE3 inhibitory activity with nanomolar concentrations and are calcium sensitizers as seen with the positive effect in the contractility assays. As described in the European Journal of Medicinal Chemistry (1996), Vol 31, pp. 805-8120; by Nadler G., et. al., for pyridazinone and thiadiazinone cardiotonic agents with one chiral center, the PDE inhibitory activity generally resides with one enantiomer (e.g., the (S) configuration for the thiadiazinones and the (R) configuration for the pyridazinones) and the myofibrillar calcium sensitization resides in the opposite configurations, respectively. To date, research and development of these dual-modality inotropes seems to have diminished sharply since new compounds have not really been described for at least 28 years or longer.

In fact, the most used inotropic compound being sold today for cardiac insufficiency in animals is pimobendan which is a racemate. Pimobendan is a benzimidazole-pyridazinone derivative that has been used to treat congestive heart failure (CHF) resulting from dilated cardiomyopathy (DCM) or DMVD in animals for about 20 years. The positive inotropic effects of pimobendan are mediated through a combination of increased c-AMP mediated PDE3 inhibition and sensitization of the cardiac contractile apparatus to intra-cellular calcium. Pimobendan was first described in U.S. Pat. No. 4,361,563A which first published February 1980 in an equivalent Australian patent application (AU197950279A). Pimobendan is orally administered twice daily to dogs at a dose of 0.5 mg/kg/day. Pimobendan is safe and well tolerated but must be administered chronically twice daily (q12 hours) which can lead to some common safety issues in animals like racing or abnormal heartbeat, bleeding or bruising, gastro-intestinal disturbances, jaundice, rash and skin redness, and has been known to induce valvular lesions in patients with asymptomatic MVD. In addition, pimobendan should not be used in cases of hypertrophic cardiomyopathy or aortic stenosis. Chronic BID dosing can also lead to administration compliance shortfalls. As with numerous marketed products, there is always a need for newer, safer and more efficacious drugs to treat the respective disease classes. The present invention describes novel dual-modal cardiotonic agents that inhibit PDE3 with nanomolar concentrations and have a positive effect on contractility, a measure of calcium sensitization for the useful treatment of cardiovascular disease including MMVD, CHF and/or asymptomatic heart failure, and/or the inhibition of platelet aggregation, in an animal, preferably canine.

SUMMARY OF THE INVENTION

In one aspect of the invention, are novel PDE3 receptor antagonists useful for the treatment of mitral valve disease and congestive heart failure in animals, particularly canines. In one aspect, are PDE3 inhibitory compounds (Example #) selected from the group consisting of:

8-(2-methoxypyridin-4-yl)-6-(4-methyl-6-oxo-1,4,5,6-tetrahydropyridazin-3-yl)-3,4-dihydroquinolin-2(1H)-one (1);

6-(4-methyl-6-oxo-1,4,5,6-tetrahydropyridazin-3-yl)-8-(thiazol-2-yl)-3,4-dihydroquinolin-2(1H)-one (2);

8-(2-methoxythiazol-5-yl)-6-(4-methyl-6-oxo-1,4,5,6-tetrahydropyridazin-3-yl)-3,4-dihydroquinolin-2(1H)-one (4);

7-chloro-5-(4-methyl-6-oxo-1,4,5,6-tetrahydropyridazin-3-yl)indolin-2-one (6);

7-(4-chlorophenyl)-5-(6-oxo-1,6-dihydropyridazin-3-yl)indolin-2-one (7);

7'-chloro-5'-(4-methyl-6-oxo-1,4,5,6-tetrahydropyridazin-3-yl)spiro[cyclopropane-1,3'-indolin]-2'-one (8);

8-(4-chlorophenyl)-6-(6-oxo-1,6-dihydropyridazin-3-yl)-3,4-dihydroquinolin-2(1H)-one (9);

8-(3-fluorophenyl)-6-(4-methyl-6-oxo-1,4,5,6-tetrahydropyridazin-3-yl)-3,4-dihydroquinolin-2(1H)-one (12);

6-(4-methyl-6-oxo-1,4,5,6-tetrahydropyridazin-3-yl)-8-(pyridin-3-yl)-3,4-dihydroquinolin-2(1H)-one (13);

3,3-dimethyl-5-(4-methyl-6-oxo-1,6-dihydropyridazin-3-yl)-7-(thiazol-4-yl)indolin-2-one (17);

9-(6-methoxypyridin-3-yl)-7-(4-methyl-6-oxo-1,4,5,6-tetrahydropyridazin-3-yl)-1,3,4,5-tetrahydro-2H-benzo[b]azepin-2-one (18);

6-(2-(1-(4-methoxyphenyl)cyclopropyl)-1H-benzo[d]imidazol-6-yl)-5-methyl-4,5-dihydropyridazin-3(2H)-one (19);

7-bromo-3,3-dimethyl-5-(4-methyl-6-oxo-1,4,5,6-tetrahydropyridazin-3-yl)indolin-2-one (23);

7-chloro-3,3-dimethyl-5-(4-methyl-6-oxo-1,4,5,6-tetrahydropyridazin-3-yl)indolin-2-one (24);

7-chloro-3,3-dimethyl-5-(6-oxo-1,6-dihydropyridazin-3-yl)indolin-2-one (25);

7-fluoro-3,3-dimethyl-5-(4-methyl-6-oxo-1,4,5,6-tetrahydropyridazin-3-yl)indolin-2-one (26);

7-fluoro-3,3-dimethyl-5-(6-oxo-1,6-dihydropyridazin-3-yl)indolin-2-one (27);

7'-fluoro-5'-(4-methyl-6-oxo-1,4,5,6-tetrahydropyridazin-3-yl)spiro[cyclopropane-1,3'-indolin]-2'-one (28);

4-chloro-6-(4-methyl-6-oxo-1,4,5,6-tetrahydropyridazin-3-yl)benzo[d]thiazol-2 (3H)-one (29);

6-(2-amino-4-chlorobenzo[d]thiazol-6-yl)-5-methyl-4,5-dihydropyridazin-3(2H)-one (30);

6-(2-amino-4-fluorobenzo[d]thiazol-6-yl)-5-methyl-4,5-dihydropyridazin-3(2H)-one (31);

7-bromo-3,3-dimethyl-5-(6-oxo-1,6-dihydropyridazin-3-yl)indolin-2-one (32); (R)-7-chloro-3,3-dimethyl-5-(4-methyl-6-oxo-1,4,5,6-tetrahydropyridazin-3-yl)indolin-2-one (33);

6-(4-fluoro-2-(methylamino)benzo[d]thiazol-6-yl)-5-methyl-4,5-dihydropyridazin-3(2H)-one (34); 8-chloro-6-(4-methyl-6-oxo-1,4,5,6-tetrahydropyridazin-3-yl)quinolin-2(1H)-one (35);

6-(8-chloro-2-hydroxyquinolin-6-yl)-5-methyl-4,5-dihydropyridazin-3(2H)-one (35a);

7-chloro-6-fluoro-3,3-dimethyl-5-(4-methyl-6-oxo-1,4,5,6-tetrahydropyridazin-3-yl)indolin-2-one (36);

6-(4-fluoro-2-(3-hydroxyazetidin-1-yl)benzo[d]thiazol-6-yl)-5-methyl-4,5-dihydropyridazin-3(2H)-one (37);

2-amino-6-(4-methyl-6-oxo-1,4,5,6-tetrahydropyridazin-3-yl)benzo[d]thiazole-4-carbonitrile (38);

7-chloro-5-(4-methyl-6-oxo-1,4,5,6-tetrahydropyridazin-3-yl)isoindolin-1-one (39);

6-(4-methyl-6-oxo-1,4,5,6-tetrahydropyridazin-3-yl)-2-oxo-1,2-dihydroquinoline-8-carbonitrile (40);

2-hydroxy-6-(4-methyl-6-oxo-1,4,5,6-tetrahydropyridazin-3-yl)quinoline-8-carbonitrile (40a);

7-chloro-3,3-dimethyl-5-(4-methyl-6-oxo-1,4,5,6-tetrahydropyridazin-3-yl)isoindolin-1-one (41);

4-chloro-1-methyl-6-(4-methyl-6-oxo-1,4,5,6-tetrahydropyridazin-3-yl)-1,3-dihydro-2H-benzo[d]imidazol-2-one (42);

7'-fluoro-5'-(4-methyl-6-oxo-1,4,5,6-tetrahydropyridazin-3-yl)spiro[cyclobutane-1,3'-indolin]-2'-one (43);

7-chloro-3,3-dimethyl-5-(6-oxo-1,4,5,6-tetrahydropyridazin-3-yl)indolin-2-one (44);

6-(8-bromo-2-hydroxyquinolin-6-yl)-5-methyl-4,5-dihydropyridazin-3(2H)-one (45);

6-(4-fluoro-2-(((1-methyl-1H-pyrazol-4-yl)methyl)amino)benzo[d]thiazol-6-yl)-5-methyl-4,5-dihydropyridazin-3(2H)-one (46);

6-(7-chloro-3-methyl-1H-indazol-5-yl)-5-methyl-4,5-dihydropyridazin-3(2H)-one (47);

6-(8-cyclopropyl-2-hydroxyquinolin-6-yl)-5-methyl-4,5-dihydropyridazin-3(2H)-one (48);

6-(2-(3-methoxyazetidin-1-yl)benzo[d]thiazol-6-yl)-5-methyl-4,5-dihydropyridazin-3(2H)-one (49);

7-fluoro-5-(4-methyl-6-oxo-1,4,5,6-tetrahydropyridazin-3-yl)indolin-2-one (50);

(S)-7-chloro-3,3-dimethyl-5-(4-methyl-6-oxo-1,4,5,6-tetrahydropyridazin-3-yl)isoindolin-2-one (51);

4-chloro-6-(6-oxo-1,6-dihydropyridazin-3-yl)benzo[d]thiazol-2 (3H)-one (52);

5-(4-methyl-6-oxo-1,4,5,6-tetrahydropyridazin-3-yl)-2-oxoindoline-7-carbonitrile (53);

4-methyl-6-(6-methyl-2-oxo-3,6-dihydro-2H-1,3,4-thiadiazin-5-yl)benzo[d]thiazol-2 (3H)-one (55);

4-chloro-6-(6-methyl-2-oxo-3,6-dihydro-2H-1,3,4-thiadiazin-5-yl)benzo[d]thiazol-2 (3H)-one (56);

5-(7-fluoro-2-oxoindolin-5-yl)-6-methyl-3,6-dihydro-2H-1,3,4-thiadiazin-2-one (57);

5-(7'-chloro-2'-oxospiro[cyclopropane-1,3'-indolin]-5'-yl)-6-methyl-3,6-dihydro-2H-1,3,4-thiadiazin-2-one (58);

5-(7-fluoro-3,3-dimethyl-2-oxoindolin-5-yl)-3,6-dihydro-2H-1,3,4-thiadiazin-2-one (59);

5-(7-chloro-3,3-dimethyl-2-oxoindolin-5-yl)-3,6-dihydro-2H-1,3,4-thiadiazin-2-one (61);

5-(7-chloro-2-oxoindolin-5-yl)-6-methyl-3,6-dihydro-2H-1,3,4-thiadiazin-2-one (62);

6-methyl-5-(7-(4-(methylsulfonyl)phenyl)-2-oxoindolin-5-yl)-3,6-dihydro-2H-1,3,4-thiadiazin-2-one (63);
5-(7-bromo-3,3-dimethyl-2-oxoindolin-5-yl)-3,6-dihydro-2H-1,3,4-thiadiazin-2-one (66);
5-(3,3-dimethyl-2-oxo-7-(thiazol-4-yl)indolin-5-yl)-6-methyl-3,6-dihydro-2H-1,3,4-thiadiazin-2-one (68);
5-(7-(4-chlorophenyl)-2-oxoindolin-5-yl)-6-methyl-3,6-dihydro-2H-1,3,4-thiadiazin-2-one (71);
5-(2-oxo-2,3,4,5-tetrahydro-1H-benzo[b]azepin-7-yl)-3,6-dihydro-2H-1,3,4-thiadiazin-2-one (72);
6-methyl-5-(9-methyl-2-oxo-2,3,4,5-tetrahydro-1H-benzo[b]azepin-7-yl)-3,6-dihydro-2H-1,3,4-thiadiazin-2-one (73);
5-(7-fluoro-3,3-dimethyl-2-oxoindolin-5-yl)-6-methyl-3,6-dihydro-2H-1,3,4-thiadiazin-2-one (74);
5-(7-chloro-3,3-dimethyl-2-oxoindolin-5-yl)-6-methyl-3,6-dihydro-2H-1,3,4-thiadiazin-2-one (75);
5-(7-bromo-3,3-dimethyl-2-oxoindolin-5-yl)-6-methyl-3,6-dihydro-2H-1,3,4-thiadiazin-2-one (76);
5-(6-methyl-2-oxo-3,6-dihydro-2H-1,3,4-thiadiazin-5-yl)-2-oxoindoline-7-carbonitrile (77);
(S)-5-(7-fluoro-2-oxoindolin-5-yl)-6-methyl-3,6-dihydro-2H-1,3,4-thiadiazin-2-one (78);
5-(7-chloro-1-oxoisoindolin-5-yl)-6-methyl-3,6-dihydro-2H-1,3,4-thiadiazin-2-one (79);
5-(7-chloro-3,3-dimethyl-1-oxoisoindolin-5-yl)-6-methyl-3,6-dihydro-2H-1,3,4-thiadiazin-2-one (80);
5-(8-chloro-2-hydroxyquinolin-6-yl)-6-methyl-3,6-dihydro-2H-1,3,4-thiadiazin-2-one (81);
5-(7-chloro-2,2-dioxido-1,3-dihydrobenzo[c]isothiazol-5-yl)-6-methyl-3,6-dihydro-2H-1,3,4-thiadiazin-2-one (82);
6-methyl-5-(8-methyl-2-oxo-1,2,3,4-tetrahydroquinolin-6-yl)-3,6-dihydro-2H-1,3,4-thiadiazin-2-one (83);
4-chloro-6-(2-oxo-2,3-dihydro-1H-pyrrolo[2,3-b]pyridin-5-yl)benzo[d]oxazol-2 (3H)-one (84);
5-(7-chloro-3,3-dimethyl-2-oxoindolin-5-yl)-1,3-dihydro-2H-pyrrolo[2,3-b]pyridin-2-one (85);
7-chloro-3,3-dimethyl-5-(pyrimidin-5-yl)indolin-2-one (86);
6-(7-chloro-3,3-dimethyl-2-oxoindolin-5-yl)-3,4-dihydro-1,8-naphthyridin-2(1H)-one (87);
4-chloro-6-(5-oxo-4,5-dihydro-1,3,4-thiadiazol-2-yl)benzo[d]thiazol-2 (3H)-one (88); and
5-(7-chloro-3,3-dimethyl-2-oxoindolin-5-yl)-1,3,4-thiadiazol-2 (3H)-one (89), stereoisomers thereof, and veterinary acceptable salts thereof.

In another aspect, are PDE3 inhibitors (Example #) selected from the group consisting of:

8-(2-methoxypyridin-4-yl)-6-(4-methyl-6-oxo-1,4,5,6-tetrahydropyridazin-3-yl)-3,4-dihydroquinolin-2(1H)-one (1);
7-chloro-5-(4-methyl-6-oxo-1,4,5,6-tetrahydropyridazin-3-yl)indolin-2-one (6);
7'-chloro-5'-(4-methyl-6-oxo-1,4,5,6-tetrahydropyridazin-3-yl)spiro[cyclopropane-1,3'-indolin]-2'-one (8);
8-(4-chlorophenyl)-6-(6-oxo-1,6-dihydropyridazin-3-yl)-3,4-dihydroquinolin-2(1H)-one (9);
8-(3-fluorophenyl)-6-(4-methyl-6-oxo-1,4,5,6-tetrahydropyridazin-3-yl)-3,4-dihydroquinolin-2(1H)-one (12);
6-(4-methyl-6-oxo-1,4,5,6-tetrahydropyridazin-3-yl)-8-(pyridin-3-yl)-3,4-dihydroquinolin-2(1H)-one (13);
9-(6-methoxypyridin-3-yl)-7-(4-methyl-6-oxo-1,4,5,6-tetrahydropyridazin-3-yl)-1,3,4,5-tetrahydro-2H-benzo[b]azepin-2-one (18);
6-(2-(1-(4-methoxyphenyl)cyclopropyl)-1H-benzo[d]imidazol-6-yl)-5-methyl-4,5-dihydropyridazin-3(2H)-one (19);
7-bromo-3,3-dimethyl-5-(4-methyl-6-oxo-1,4,5,6-tetrahydropyridazin-3-yl)indolin-2-one (23);
7-chloro-3,3-dimethyl-5-(4-methyl-6-oxo-1,4,5,6-tetrahydropyridazin-3-yl)indolin-2-one (24);
7-chloro-3,3-dimethyl-5-(6-oxo-1,6-dihydropyridazin-3-yl)indolin-2-one (25);
7-fluoro-3,3-dimethyl-5-(4-methyl-6-oxo-1,4,5,6-tetrahydropyridazin-3-yl)indolin-2-one (26);
7-fluoro-3,3-dimethyl-5-(6-oxo-1,6-dihydropyridazin-3-yl)indolin-2-one (27);
7'-fluoro-5'-(4-methyl-6-oxo-1,4,5,6-tetrahydropyridazin-3-yl)spiro[cyclopropane-1,3'-indolin]-2'-one (28);
6-(2-amino-4-chlorobenzo[d]thiazol-6-yl)-5-methyl-4,5-dihydropyridazin-3(2H)-one (30);
6-(2-amino-4-fluorobenzo[d]thiazol-6-yl)-5-methyl-4,5-dihydropyridazin-3(2H)-one (31);
7-bromo-3,3-dimethyl-5-(6-oxo-1,6-dihydropyridazin-3-yl)indolin-2-one (32);
(R)-7-chloro-3,3-dimethyl-5-(4-methyl-6-oxo-1,4,5,6-tetrahydropyridazin-3-yl)indolin-2-one (33);
6-(4-fluoro-2-(methylamino)benzo[d]thiazol-6-yl)-5-methyl-4,5-dihydropyridazin-3(2H)-one (34);
8-chloro-6-(4-methyl-6-oxo-1,4,5,6-tetrahydropyridazin-3-yl)quinolin-2(1H)-one (35);
6-(8-chloro-2-hydroxyquinolin-6-yl)-5-methyl-4,5-dihydropyridazin-3(2H)-one (35a);
7-chloro-6-fluoro-3,3-dimethyl-5-(4-methyl-6-oxo-1,4,5,6-tetrahydropyridazin-3-yl)indolin-2-one (36);
6-(4-fluoro-2-(3-hydroxyazetidin-1-yl)benzo[d]thiazol-6-yl)-5-methyl-4,5-dihydropyridazin-3(2H)-one (37);
2-amino-6-(4-methyl-6-oxo-1,4,5,6-tetrahydropyridazin-3-yl)benzo[d]thiazole-4-carbonitrile (38);
7-chloro-5-(4-methyl-6-oxo-1,4,5,6-tetrahydropyridazin-3-yl)isoindolin-1-one (39);
6-(4-methyl-6-oxo-1,4,5,6-tetrahydropyridazin-3-yl)-2-oxo-1,2-dihydroquinoline-8-carbonitrile (40);
2-hydroxy-6-(4-methyl-6-oxo-1,4,5,6-tetrahydropyridazin-3-yl)quinoline-8-carbonitrile (40a);
7-chloro-3,3-dimethyl-5-(4-methyl-6-oxo-1,4,5,6-tetrahydropyridazin-3-yl)isoindolin-1-one (41);
4-chloro-1-methyl-6-(4-methyl-6-oxo-1,4,5,6-tetrahydropyridazin-3-yl)-1,3-dihydro-2H-benzo[d]imidazol-2-one (42);
7'-fluoro-5'-(4-methyl-6-oxo-1,4,5,6-tetrahydropyridazin-3-yl)spiro[cyclobutane-1,3'-indolin]-2'-one (43);
7-chloro-3,3-dimethyl-5-(6-oxo-1,4,5,6-tetrahydropyridazin-3-yl)indolin-2-one (44);
4-chloro-6-(6-methyl-2-oxo-3,6-dihydro-2H-1,3,4-thiadiazin-5-yl)benzo[d]thiazol-2 (3H)-one (56);
5-(7-fluoro-2-oxoindolin-5-yl)-6-methyl-3,6-dihydro-2H-1,3,4-thiadiazin-2-one (57);
5-(7'-chloro-2'-oxospiro[cyclopropane-1,3'-indolin]-5'-yl)-6-methyl-3,6-dihydro-2H-1,3,4-thiadiazin-2-one (58);
5-(7-fluoro-3,3-dimethyl-2-oxoindolin-5-yl)-3,6-dihydro-2H-1,3,4-thiadiazin-2-one (59);
5-(7-chloro-3,3-dimethyl-2-oxoindolin-5-yl)-3,6-dihydro-2H-1,3,4-thiadiazin-2-one (61);
5-(7-chloro-2-oxoindolin-5-yl)-6-methyl-3,6-dihydro-2H-1,3,4-thiadiazin-2-one (62);
6-methyl-5-(7-(4-(methylsulfonyl)phenyl)-2-oxoindolin-5-yl)-3,6-dihydro-2H-1,3,4-thiadiazin-2-one (63);
5-(7-bromo-3,3-dimethyl-2-oxoindolin-5-yl)-3,6-dihydro-2H-1,3,4-thiadiazin-2-one (66);
5-(7-(4-chlorophenyl)-2-oxoindolin-5-yl)-6-methyl-3,6-dihydro-2H-1,3,4-thiadiazin-2-one (71);

6-methyl-5-(9-methyl-2-oxo-2,3,4,5-tetrahydro-1H-benzo[b]azepin-7-yl)-3,6-dihydro-2H-1,3,4-thiadiazin-2-one (73);
5-(7-fluoro-3,3-dimethyl-2-oxoindolin-5-yl)-6-methyl-3,6-dihydro-2H-1,3,4-thiadiazin-2-one (74);
5-(7-chloro-3,3-dimethyl-2-oxoindolin-5-yl)-6-methyl-3,6-dihydro-2H-1,3,4-thiadiazin-2-one (75);
5-(7-bromo-3,3-dimethyl-2-oxoindolin-5-yl)-6-methyl-3,6-dihydro-2H-1,3,4-thiadiazin-2-one (76);
5-(6-methyl-2-oxo-3,6-dihydro-2H-1,3,4-thiadiazin-5-yl)-2-oxoindoline-7-carbonitrile (77);
(S)-5-(7-fluoro-2-oxoindolin-5-yl)-6-methyl-3,6-dihydro-2H-1,3,4-thiadiazin-2-one (78);
5-(7-chloro-1-oxoisoindolin-5-yl)-6-methyl-3,6-dihydro-2H-1,3,4-thiadiazin-2-one (79);
5-(7-chloro-3,3-dimethyl-1-oxoisoindolin-5-yl)-6-methyl-3,6-dihydro-2H-1,3,4-thiadiazin-2-one (80);
6-methyl-5-(8-methyl-2-oxo-1,2,3,4-tetrahydroquinolin-6-yl)-3,6-dihydro-2H-1,3,4-thiadiazin-2-one (83);
5-(7-chloro-3,3-dimethyl-2-oxoindolin-5-yl)-1,3-dihydro-2H-pyrrolo[2,3-b]pyridin-2-one (85); and
7-chloro-3,3-dimethyl-5-(pyrimidin-5-yl)indolin-2-one (86), stereoisomers thereof, and veterinary acceptable salts thereof.

In another aspect is a PDE3 inhibitor (Example #) selected from the group consisting of:
8-(3-fluorophenyl)-6-(4-methyl-6-oxo-1,4,5,6-tetrahydropyridazin-3-yl)-3,4-dihydroquinolin-2(1H)-one (12);
6-(2-(1-(4-methoxyphenyl)cyclopropyl)-1H-benzo[d]imidazol-6-yl)-5-methyl-4,5-dihydropyridazin-3(2H)-one (19);
7-bromo-3,3-dimethyl-5-(4-methyl-6-oxo-1,4,5,6-tetrahydropyridazin-3-yl)indolin-2-one (23);
7-chloro-3,3-dimethyl-5-(4-methyl-6-oxo-1,4,5,6-tetrahydropyridazin-3-yl)indolin-2-one (24);
7-chloro-3,3-dimethyl-5-(6-oxo-1,6-dihydropyridazin-3-yl)indolin-2-one (25);
7-fluoro-3,3-dimethyl-5-(4-methyl-6-oxo-1,4,5,6-tetrahydropyridazin-3-yl)indolin-2-one (26);
7-fluoro-3,3-dimethyl-5-(6-oxo-1,6-dihydropyridazin-3-yl)indolin-2-one (27);
7'-fluoro-5'-(4-methyl-6-oxo-1,4,5,6-tetrahydropyridazin-3-yl)spiro[cyclopropane-1,3'-indolin]-2'-one (28);
6-(2-amino-4-chlorobenzo[d]thiazol-6-yl)-5-methyl-4,5-dihydropyridazin-3(2H)-one (30);
6-(2-amino-4-fluorobenzo[d]thiazol-6-yl)-5-methyl-4,5-dihydropyridazin-3(2H)-one (31);
7-bromo-3,3-dimethyl-5-(6-oxo-1,6-dihydropyridazin-3-yl)indolin-2-one (32);
(R)-7-chloro-3,3-dimethyl-5-(4-methyl-6-oxo-1,4,5,6-tetrahydropyridazin-3-yl)indolin-2-one (33);
4-chloro-6-(6-methyl-2-oxo-3,6-dihydro-2H-1,3,4-thiadiazin-5-yl)benzo[d]thiazol-2 (3H)-one (56);
5-(7-fluoro-2-oxoindolin-5-yl)-6-methyl-3,6-dihydro-2H-1,3,4-thiadiazin-2-one (57);
5-(7'-chloro-2'-oxospiro[cyclopropane-1,3'-indolin]-5'-yl)-6-methyl-3,6-dihydro-2H-1,3,4-thiadiazin-2-one (58);
5-(7-chloro-3,3-dimethyl-2-oxoindolin-5-yl)-3,6-dihydro-2H-1,3,4-thiadiazin-2-one (61);
5-(7-chloro-2-oxoindolin-5-yl)-6-methyl-3,6-dihydro-2H-1,3,4-thiadiazin-2-one (62);
5-(7-bromo-3,3-dimethyl-2-oxoindolin-5-yl)-3,6-dihydro-2H-1,3,4-thiadiazin-2-one (66);
6-methyl-5-(9-methyl-2-oxo-2,3,4,5-tetrahydro-1H-benzo[b]azepin-7-yl)-3,6-dihydro-2H-1,3,4-thiadiazin-2-one (73);
5-(7-fluoro-3,3-dimethyl-2-oxoindolin-5-yl)-6-methyl-3,6-dihydro-2H-1,3,4-thiadiazin-2-one (74);
5-(7-chloro-3,3-dimethyl-2-oxoindolin-5-yl)-6-methyl-3,6-dihydro-2H-1,3,4-thiadiazin-2-one (75);
5-(7-bromo-3,3-dimethyl-2-oxoindolin-5-yl)-6-methyl-3,6-dihydro-2H-1,3,4-thiadiazin-2-one (76);
5-(6-methyl-2-oxo-3,6-dihydro-2H-1,3,4-thiadiazin-5-yl)-2-oxoindoline-7-carbonitrile (77);
(S)-5-(7-fluoro-2-oxoindolin-5-yl)-6-methyl-3,6-dihydro-2H-1,3,4-thiadiazin-2-one (78);
5-(7-chloro-3,3-dimethyl-2-oxoindolin-5-yl)-1,3-dihydro-2H-pyrrolo[2,3-b]pyridin-2-one (85); and
7-chloro-3,3-dimethyl-5-(pyrimidin-5-yl)indolin-2-one (86), stereoisomers thereof, and veterinary acceptable salts thereof.

In another aspect, is a PDE3 inhibitor (Example #) selected from the group consisting of:
6-(2-(1-(4-methoxyphenyl)cyclopropyl)-1H-benzo[d]imidazol-6-yl)-5-methyl-4,5-dihydropyridazin-3(2H)-one (19);
7-bromo-3,3-dimethyl-5-(4-methyl-6-oxo-1,4,5,6-tetrahydropyridazin-3-yl)indolin-2-one (23);
7-chloro-3,3-dimethyl-5-(4-methyl-6-oxo-1,4,5,6-tetrahydropyridazin-3-yl)indolin-2-one (24);
7-chloro-3,3-dimethyl-5-(6-oxo-1,6-dihydropyridazin-3-yl)indolin-2-one (25);
5-(7-fluoro-2-oxoindolin-5-yl)-6-methyl-3,6-dihydro-2H-1,3,4-thiadiazin-2-one (57);
5-(7-chloro-3,3-dimethyl-2-oxoindolin-5-yl)-3,6-dihydro-2H-1,3,4-thiadiazin-2-one (61);
5-(7-chloro-2-oxoindolin-5-yl)-6-methyl-3,6-dihydro-2H-1,3,4-thiadiazin-2-one (62);
6-methyl-5-(9-methyl-2-oxo-2,3,4,5-tetrahydro-1H-benzo[b]azepin-7-yl)-3,6-dihydro-2H-1,3,4-thiadiazin-2-one (73);
5-(7-fluoro-3,3-dimethyl-2-oxoindolin-5-yl)-6-methyl-3,6-dihydro-2H-1,3,4-thiadiazin-2-one (74);
5-(7-chloro-3,3-dimethyl-2-oxoindolin-5-yl)-6-methyl-3,6-dihydro-2H-1,3,4-thiadiazin-2-one (75);
5-(7-bromo-3,3-dimethyl-2-oxoindolin-5-yl)-6-methyl-3,6-dihydro-2H-1,3,4-thiadiazin-2-one (76); and
7-chloro-3,3-dimethyl-5-(pyrimidin-5-yl)indolin-2-one (86), stereoisomers thereof, and veterinary acceptable salts thereof.

In another aspect, is a PDE3 inhibitor (Example #) selected from the group consisting of:
6-(2-(1-(4-methoxyphenyl)cyclopropyl)-1H-benzo[d]imidazol-6-yl)-5-methyl-4,5-dihydropyridazin-3(2H)-one (19);
7-bromo-3,3-dimethyl-5-(4-methyl-6-oxo-1,4,5,6-tetrahydropyridazin-3-yl)indolin-2-one (23);
7-chloro-3,3-dimethyl-5-(4-methyl-6-oxo-1,4,5,6-tetrahydropyridazin-3-yl)indolin-2-one (24);
5-(7-fluoro-2-oxoindolin-5-yl)-6-methyl-3,6-dihydro-2H-1,3,4-thiadiazin-2-one (57);
5-(7-chloro-3,3-dimethyl-2-oxoindolin-5-yl)-3,6-dihydro-2H-1,3,4-thiadiazin-2-one (61);
5-(7-chloro-2-oxoindolin-5-yl)-6-methyl-3,6-dihydro-2H-1,3,4-thiadiazin-2-one (62);
6-methyl-5-(9-methyl-2-oxo-2,3,4,5-tetrahydro-1H-benzo[b]azepin-7-yl)-3,6-dihydro-2H-1,3,4-thiadiazin-2-one (73);
5-(7-fluoro-3,3-dimethyl-2-oxoindolin-5-yl)-6-methyl-3,6-dihydro-2H-1,3,4-thiadiazin-2-one (74);
5-(7-chloro-3,3-dimethyl-2-oxoindolin-5-yl)-6-methyl-3,6-dihydro-2H-1,3,4-thiadiazin-2-one (75); and 5-(7-bromo-3,3-dimethyl-2-oxoindolin-5-yl)-6-methyl-3,6-dihydro-2H-1,3,4-thiadiazin-2-one (76), stereoisomers thereof, and veterinary acceptable salts thereof.

In another aspect, are PDE3 inhibitors (Example #) selected from the group consisting of:

6-(2-(1-(4-methoxyphenyl)cyclopropyl)-1H-benzo[d]imidazol-6-yl)-5-methyl-4,5-dihydropyridazin-3(2H)-one (19);

5-(7-fluoro-2-oxoindolin-5-yl)-6-methyl-3,6-dihydro-2H-1,3,4-thiadiazin-2-one (57);

5-(7-chloro-3,3-dimethyl-2-oxoindolin-5-yl)-3,6-dihydro-2H-1,3,4-thiadiazin-2-one (61);

5-(7-chloro-2-oxoindolin-5-yl)-6-methyl-3,6-dihydro-2H-1,3,4-thiadiazin-2-one (62); and 6-methyl-5-(9-methyl-2-oxo-2,3,4,5-tetrahydro-1H-benzo[b]azepin-7-yl)-3,6-dihydro-2H-1,3,4-thiadiazin-2-one (73), stereoisomers thereof, and veterinary acceptable salts thereof.

In another aspect, are PDE3 inhibitors (Example #) selected from the group consisting of:

7-bromo-3,3-dimethyl-5-(4-methyl-6-oxo-1,4,5,6-tetrahydropyridazin-3-yl)indolin-2-one (23);

7-chloro-3,3-dimethyl-5-(4-methyl-6-oxo-1,4,5,6-tetrahydropyridazin-3-yl)indolin-2-one (24);

7-chloro-3,3-dimethyl-5-(6-oxo-1,6-dihydropyridazin-3-yl)indolin-2-one (25);

5-(7-fluoro-3,3-dimethyl-2-oxoindolin-5-yl)-6-methyl-3,6-dihydro-2H-1,3,4-thiadiazin-2-one (74);

5-(7-chloro-3,3-dimethyl-2-oxoindolin-5-yl)-6-methyl-3,6-dihydro-2H-1,3,4-thiadiazin-2-one (75);

5-(7-bromo-3,3-dimethyl-2-oxoindolin-5-yl)-6-methyl-3,6-dihydro-2H-1,3,4-thiadiazin-2-one (76); and 7-chloro-3,3-dimethyl-5-(pyrimidin-5-yl)indolin-2-one (86), stereoisomers thereof, and veterinary acceptable salts thereof.

In another aspect, are PDE3 inhibitors (Example #) selected from the group consisting of:

6-(2-(1-(4-methoxyphenyl)cyclopropyl)-1H-benzo[d]imidazol-6-yl)-5-methyl-4,5-dihydropyridazin-3(2H)-one (19);

7-bromo-3,3-dimethyl-5-(4-methyl-6-oxo-1,4,5,6-tetrahydropyridazin-3-yl)indolin-2-one (23);

7-chloro-3,3-dimethyl-5-(4-methyl-6-oxo-1,4,5,6-tetrahydropyridazin-3-yl)indolin-2-one (24);

5-(7-fluoro-2-oxoindolin-5-yl)-6-methyl-3,6-dihydro-2H-1,3,4-thiadiazin-2-one (57);

5-(7-chloro-2-oxoindolin-5-yl)-6-methyl-3,6-dihydro-2H-1,3,4-thiadiazin-2-one (62); and 5-(7-chloro-3,3-dimethyl-2-oxoindolin-5-yl)-6-methyl-3,6-dihydro-2H-1,3,4-thiadiazin-2-one (75), stereoisomers thereof, and veterinary acceptable salts thereof.

In another aspect, are PDE3 inhibitors selected from the group consisting of:

6-(2-(1-(4-methoxyphenyl)cyclopropyl)-1H-benzo[d]imidazol-6-yl)-5-methyl-4,5-dihydropyridazin-3(2H)-one (19);

5-(7-fluoro-2-oxoindolin-5-yl)-6-methyl-3,6-dihydro-2H-1,3,4-thiadiazin-2-one (57); and 5-(7-chloro-2-oxoindolin-5-yl)-6-methyl-3,6-dihydro-2H-1,3,4-thiadiazin-2-one (62), stereoisomers thereof, and veterinary acceptable salts thereof.

In another aspect, are PDE3 inhibitors (Example #) selected from the group consisting of:

7-bromo-3,3-dimethyl-5-(4-methyl-6-oxo-1,4,5,6-tetrahydropyridazin-3-yl)indolin-2-one (23);

7-chloro-3,3-dimethyl-5-(4-methyl-6-oxo-1,4,5,6-tetrahydropyridazin-3-yl)indolin-2-one (24); and 5-(7-chloro-3,3-dimethyl-2-oxoindolin-5-yl)-6-methyl-3,6-dihydro-2H-1,3,4-thiadiazin-2-one (75), stereoisomers thereof, and veterinary acceptable salts thereof.

In another aspect, is the PDE3 inhibitor 6-(2-(1-(4-methoxyphenyl)cyclopropyl)-1H-benzo[d]imidazol-6-yl)-5-methyl-4,5-dihydropyridazin-3(2H)-one (19), stereoisomer thereof, and veterinary acceptable salt thereof.

In another aspect, is the PDE3 inhibitor 7-bromo-3,3-dimethyl-5-(4-methyl-6-oxo-1,4,5,6-tetrahydropyridazin-3-yl)indolin-2-one (23), stereoisomer thereof, and veterinary acceptable salt thereof.

In another aspect, is the PDE3 inhibitor 7-chloro-3,3-dimethyl-5-(4-methyl-6-oxo-1,4,5,6-tetrahydropyridazin-3-yl)indolin-2-one (24), stereoisomer thereof, and veterinary acceptable salt thereof.

In another aspect, is the PDE3 inhibitor 7-chloro-3,3-dimethyl-5-(6-oxo-1,6-dihydropyridazin-3-yl)indolin-2-one (25), stereoisomer thereof, and veterinary acceptable salt thereof.

In another aspect, is the PDE3 inhibitor 5-(7-fluoro-2-oxoindolin-5-yl)-6-methyl-3,6-dihydro-2H-1,3,4-thiadiazin-2-one (57), stereoisomer thereof, and veterinary acceptable salt thereof.

In another aspect, is the PDE3 5-(7-chloro-3,3-dimethyl-2-oxoindolin-5-yl)-3,6-dihydro-2H-1,3,4-thiadiazin-2-one (61), stereoisomers thereof, and veterinary acceptable salts thereof.

In another aspect, is the PDE3 inhibitor 5-(7-chloro-2-oxoindolin-5-yl)-6-methyl-3,6-dihydro-2H-1,3,4-thiadiazin-2-one (62), stereoisomers thereof, and veterinary acceptable salts thereof.

In another aspect, is the PDE3 inhibitor 6-methyl-5-(9-methyl-2-oxo-2,3,4,5-tetrahydro-1H-benzo[b]azepin-7-yl)-3,6-dihydro-2H-1,3,4-thiadiazin-2-one (73), stereoisomers thereof, and veterinary acceptable salts thereof.

In another aspect, is the PDE3 inhibitor 5-(7-fluoro-3,3-dimethyl-2-oxoindolin-5-yl)-6-methyl-3,6-dihydro-2H-1,3,4-thiadiazin-2-one (74), stereoisomers thereof, and veterinary acceptable salts thereof.

In another aspect, is the PDE3 inhibitor 5-(7-chloro-3,3-dimethyl-2-oxoindolin-5-yl)-6-methyl-3,6-dihydro-2H-1,3,4-thiadiazin-2-one (75), stereoisomer thereof, and veterinary acceptable salt thereof.

In another aspect, is the PDE3 inhibitor 5-(7-bromo-3,3-dimethyl-2-oxoindolin-5-yl)-6-methyl-3,6-dihydro-2H-1,3,4-thiadiazin-2-one (76), stereoisomers thereof, and veterinary acceptable salts thereof.

In another aspect, is the PDE3 inhibitor 7-chloro-3,3-dimethyl-5-(pyrimidin-5-yl)indolin-2-one (86), stereoisomer thereof, and veterinary acceptable salt thereof.

In another aspect of the invention, is a composition comprising a compound of the invention selected from the group consisting of Example #1, 2, 4, 6-9, 12-13, 17-19, 23-53, 55-59, 61-63, 66, 68, and 71-89, stereoisomer thereof, or a veterinary acceptable salt thereof. In another aspect, is a composition comprising a compound of the invention selected from the group consisting of Example #1, 6, 8, 12-13, 18-19, 23-28, 30-43, 56-59, 61-63, 66, 71, 73-80, 83 and 85-86, stereoisomer thereof, or a veterinary acceptable salt thereof. In another aspect, is a composition comprising a compound of the invention selected from the group consisting of Example #12, 19, 23-28, 30-33, 56-58, 61-62, 66, 73-78, 85 and 86, stereoisomer thereof, or a veterinary acceptable salt thereof. In another aspect, is a composition comprising a compound of the invention selected from the group consisting of Example #19, 23, 24, 57, 61-62 and 73-76, stereoisomer thereof, or a veterinary acceptable salt thereof. In another aspect, is a composition comprising any one of the compounds selected from Example #19, 57, 61, 62 and 73, stereoisomer thereof, or a veterinary acceptable salt thereof. In another aspect, is a composition comprising a compound of the invention selected from the group consisting of Example #23, 24, 25, 74, 75, 76 and 86, stereoisomer thereof, or a veterinary acceptable salt thereof. In another aspect, is a composition comprising a compound of the invention selected from the group consisting of Example #23, 24, 74, 75 and 76, stereoisomer thereof, or a veterinary acceptable salt thereof. In another aspect, is a composition comprising a compound of the invention selected from the group consisting of Example #19, 57 and 62, stereoisomer thereof, or a veterinary acceptable salt thereof. In another aspect, is a composition comprising a compound of the invention selected from the group consisting of Example #23, 24 and 75, stereoisomer thereof, or a veterinary acceptable salt thereof. In another aspect, is a composition comprising Example #19, stereoisomer thereof, and a veterinary acceptable salt thereof. In another aspect, is a composition comprising Example #23, stereoisomer thereof, and a veterinary acceptable salt thereof. In another aspect, is a composition comprising Example #24, stereoisomer thereof, or a veterinary acceptable salt thereof. In another aspect, is a composition comprising Example #25, stereoisomer thereof, or a veterinary acceptable salt thereof. In another aspect, is a composition comprising Example #57, stereoisomer thereof, or a veterinary acceptable salt thereof. In another aspect, is a composition comprising Example #61, stereoisomer thereof, or a veterinary acceptable salt thereof. In another aspect, is a composition comprising Example #62, stereoisomer thereof, or a veterinary acceptable salt thereof. In another aspect, is a composition comprising Example #73, stereoisomer thereof, or a veterinary acceptable salt thereof. In another aspect, is a composition comprising Example #74, stereoisomer thereof, or a veterinary acceptable salt thereof. In another aspect, is a composition comprising Example #75, stereoisomer thereof, or a veterinary acceptable salt thereof. In another aspect, is a composition comprising Example #76, stereoisomer thereof, or a veterinary acceptable salt thereof. In another aspect, is a composition comprising Example #86, stereoisomer thereof, and a veterinary acceptable salt thereof. In another aspect, is a composition comprising Example #86, stereoisomer thereof, or a veterinary acceptable salt thereof. In another aspect, the composition further comprises at least one veterinary acceptable excipient. In yet another aspect, the composition further comprises at least one additional pharmaceutical agent. In another aspect, the at least one additional pharmaceutical agent is selected from the group consisting of an ACE inhibitor, furosemide and a spironolactone. In another aspect, each of the compositions described herein can be in a solid or liquid form. Preferably, the compositions described herein are in solid form; for example, a tablet or a capsule, that can be administered orally. The oral composition can be a film coated tablet or a flavored chewable tablet.

In another aspect of the invention, is a method of treating an animal with MMVD, CHF and/or asymptomatic heart failure, by administering a therapeutic amount of a compound of the invention selected from the group consisting of Example #1, 2, 4, 6-9, 12-13, 17-19, 23-53, 55-59, 61-63, 66, 68, and 71-89, stereoisomer thereof, or a veterinary acceptable salt thereof. In another aspect, is a method of treating an animal with MMVD, CHF and/or asymptomatic heart failure, by administering a therapeutic amount of compound of the invention selected from the group consisting of Example #1, 6, 8, 12-13, 18-19, 23-28, 30-43, 56-59, 61-63, 66, 71, 73-80, 83 and 85-86, stereoisomer thereof, or a veterinary acceptable salt thereof. In another aspect, is a method of treating an animal with MMVD, CHF and/or asymptomatic heart failure, by administering a therapeutic amount of compound of the invention selected from the group consisting of Example #12, 19, 23-28, 30-33, 56-58, 61-62, 66, 73-78, 85 and 86, stereoisomer thereof, or a veterinary acceptable salt thereof. In another aspect, is a method of treating an animal with MMVD, CHF and/or asymptomatic heart failure, by administering a therapeutic amount of compound of the invention selected from the group consisting of Example #19, 23, 24, 57, 61-62 and 73-76, stereoisomer thereof, or a veterinary acceptable salt thereof. In another aspect, is a method of treating an animal with MMVD, CHF and/or asymptomatic heart failure, by administering a therapeutic amount of compound of the invention selected from the group consisting of Example #19, 57, 61, 62 and 73, stereoisomer thereof, or a veterinary acceptable salt thereof. In another aspect, is a method of treating an animal with MMVD, CHF and/or asymptomatic heart failure, by administering a therapeutic amount of compound of the invention selected from the group consisting of Example #23, 24, 25, 74, 75, 76 and 86, stereoisomer thereof, or a veterinary acceptable salt thereof. In another aspect, is a method of treating an animal with MMVD, CHF and/or asymptomatic heart failure, by administering a therapeutic amount of compound of the invention selected from the group consisting of Example #23, 24, 74, 75 and 76, stereoisomer thereof, or a veterinary acceptable salt thereof. In another aspect, is a method of treating an animal with MMVD, CHF and/or asymptomatic heart failure, by administering a therapeutic amount of compound of the invention selected from the group consisting of Example #19, 57 and 62, stereoisomer thereof, or a veterinary acceptable salt thereof. In another aspect, is a method of treating an animal with MMVD, CHF and/or asymptomatic heart failure, by administering a therapeutic amount of compound of the invention selected from the group consisting of Example #23, 24 and 75, stereoisomer thereof, or a veterinary acceptable salt thereof. In another aspect, is a method of treating an animal with MMVD, CHF and/or asymptomatic heart failure, by administering a therapeutic amount of Example #19, stereoisomer thereof, and a veterinary acceptable salt thereof. In another aspect, is a method of treating an animal with MMVD, CHF and/or asymptomatic heart failure, by administering a therapeutic amount of Example #23, stereoisomer thereof, and a veterinary acceptable salt thereof. In another aspect, is a method of treating an animal with MMVD, CHF and/or asymptomatic heart failure, by administering a therapeutic amount of Example #24, stereoisomer thereof, and a veterinary acceptable salt thereof. In another aspect, is a method of treating an animal with MMVD, CHF and/or asymptomatic heart failure, by administering a therapeutic amount of Example #25, stereoisomer thereof, and a veterinary acceptable salt thereof. In another aspect, is a method of treating an animal with MMVD, CHF and/or asymptomatic heart failure, by administering a therapeutic amount of Example #57, stereoisomer thereof, and a veterinary acceptable salt thereof. In another aspect, is a method of treating an animal with MMVD, CHF and/or asymptomatic heart failure, by administering a therapeutic amount of Example #61, stereoisomer thereof, and a veterinary acceptable salt thereof. In another aspect, is a method of treating an animal with MMVD, CHF and/or asymptomatic heart failure, by administering a therapeutic amount of Example

#62, stereoisomer thereof, and a veterinary acceptable salt thereof. In another aspect, is a method of treating an animal with MMVD, CHF and/or asymptomatic heart failure, by administering a therapeutic amount of Example #73, stereoisomer thereof, and a veterinary acceptable salt thereof. In another aspect, is a method of treating an animal with MMVD, CHF and/or asymptomatic heart failure, by administering a therapeutic amount of Example #74, stereoisomer thereof, and a veterinary acceptable salt thereof. In another aspect, is a method of treating an animal with MMVD, CHF and/or asymptomatic heart failure, by administering a therapeutic amount of Example #75, stereoisomer thereof, and a veterinary acceptable salt thereof. In another aspect, is a method of treating an animal with MMVD, CHF and/or asymptomatic heart failure, by administering a therapeutic amount of Example #76, stereoisomer thereof, and a veterinary acceptable salt thereof. In another aspect, is a method of treating an animal with MMVD, CHF and/or asymptomatic heart failure, by administering a therapeutic amount of Example #86, stereoisomer thereof, and a veterinary acceptable salt thereof. In yet another aspect of treating an animal with MMVD, CHF and/or asymptomatic heart failure, by administering a therapeutic amount of any one of the compounds of the invention, is the method of co-administering at least one additional pharmaceutical agent selected from the group consisting of an ACE inhibitor, furosemide and a spironolactone.

In another aspect of the invention, is the use of a compound of the invention selected from the group consisting of Example #1, 2, 4, 6-9, 12-13, 17-19, 23-53, 55-59, 61-63, 66, 68, and 71-89, stereoisomer thereof, or a veterinary acceptable salt thereof, to prepare a medicament for treating an animal with MMVD, CHF and/or asymptomatic heart failure. In another aspect, is the use of a compound of the invention selected from the group consisting of Example #1, 6, 8, 12-13, 18-19, 23-28, 30-43, 56-59, 61-63, 66, 71, 73-80, 83 and 85-86, stereoisomer thereof, or a veterinary acceptable salt thereof, to prepare a medicament for treating an animal with MMVD, CHF and/or asymptomatic heart failure. In another aspect, is the use of a compound of the invention selected from the group consisting of Example #12, 19, 23-28, 30-33, 56-58, 61-62, 66, 73-78, 85 and 86, stereoisomer thereof, or a veterinary acceptable salt thereof, to prepare a medicament for treating an animal with MMVD, CHF and/or asymptomatic heart failure. In another aspect, is the use of a compound of the invention selected from the group consisting of Example #19, 23, 24, 57, 61-62 and 73-76, stereoisomer thereof, or a veterinary acceptable salt thereof, to prepare a medicament for treating an animal with MMVD, CHF and/or asymptomatic heart failure. In another aspect, is the use of a compound of the invention selected from the group consisting of Example #19, 57, 61, 62 and 73, stereoisomer thereof, or a veterinary acceptable salt thereof, to prepare a medicament for treating an animal with MMVD, CHF and/or asymptomatic heart failure. In another aspect, is the use of a compound of the invention selected from the group consisting of Example #23, 24, 25, 74, 75, 76 and 86, stereoisomer thereof, or a veterinary acceptable salt thereof, to prepare a medicament for treating an animal with MMVD, CHF and/or asymptomatic heart failure. In another aspect, is the use of a compound of the invention selected from the group consisting of Example #23, 24, 74, 75 and 76, stereoisomer thereof, or a veterinary acceptable salt thereof, to prepare a medicament for treating an animal with MMVD, CHF and/or asymptomatic heart failure. In another aspect, is the use of a compound of the invention selected from the group consisting of Example #19, 57 and 62, stereoisomers thereof, or a veterinary acceptable salt thereof, to prepare a medicament for treating an animal with MMVD, CHF and/or asymptomatic heart failure. In another aspect, is the use of a compound of the invention selected from the group consisting of Example #23, 24, and 75, stereoisomers thereof, or a veterinary acceptable salt thereof, to prepare a medicament for treating an animal with MMVD, CHF and/or asymptomatic heart failure. In another aspect, is the use of Example #19, stereoisomer thereof, or a veterinary acceptable salt thereof, to prepare a medicament for treating an animal with MMVD, CHF and/or asymptomatic heart failure. In another aspect, is the use of Example #23, stereoisomer thereof, or a veterinary acceptable salt thereof, to prepare a medicament for treating an animal with MMVD, CHF and/or asymptomatic heart failure. In another aspect, is the use of Example #24, stereoisomer thereof, or a veterinary acceptable salt thereof, to prepare a medicament for treating an animal with MMVD, CHF and/or asymptomatic heart failure. In another aspect, is the use of Example #25, stereoisomer thereof, or a veterinary acceptable salt thereof, to prepare a medicament for treating an animal with MMVD, CHF and/or asymptomatic heart failure. In another aspect, is the use of Example #57, stereoisomer thereof, or a veterinary acceptable salt thereof, to prepare a medicament for treating an animal with MMVD, CHF and/or asymptomatic heart failure. In another aspect, is the use of Example #61, stereoisomer thereof, or a veterinary acceptable salt thereof, to prepare a medicament for treating an animal with MMVD, CHF and/or asymptomatic heart failure. In another aspect, is the use of Example #62, stereoisomer thereof, or a veterinary acceptable salt thereof, to prepare a medicament for treating an animal with MMVD, CHF and/or asymptomatic heart failure. In another aspect, is the use of Example #73, stereoisomer thereof, or a veterinary acceptable salt thereof, to prepare a medicament for treating an animal with MMVD, CHF and/or asymptomatic heart failure. In another aspect, is the use of Example #74, stereoisomer thereof, or a veterinary acceptable salt thereof, to prepare a medicament for treating an animal with MMVD, CHF and/or asymptomatic heart failure. In another aspect, is the use of Example #75, stereoisomer thereof, or a veterinary acceptable salt thereof, to prepare a medicament for treating an animal with MMVD, CHF and/or asymptomatic heart failure. In another aspect, is the use of Example #76, stereoisomer thereof, or a veterinary acceptable salt thereof, to prepare a medicament for treating an animal with MMVD, CHF and/or asymptomatic heart failure. In another aspect, is the use of Example #86, stereoisomer thereof, or a veterinary acceptable salt thereof, to prepare a medicament for treating an animal with MMVD, CHF and/or asymptomatic heart failure. In yet another aspect, is the use of any one of the compounds of the invention for preparing a medicament with at least one other additional pharmaceutical agent selected from the group consisting of an ACE inhibitor, furosemide and a spironolactone for treating an animal with MMVD, CHF and/or asymptomatic heart failure.

DESCRIPTION

Definitions

For purposes of the invention, as described and claimed herein, the following terms and phrases are defined as follows:

"Additional veterinary (or pharmaceutical agent(s)" as used herein, unless otherwise indicated, refers to other veterinary or pharmaceutical compounds or products (i.e., drugs) that provide a therapeutically effective amount of said agent(s) that are useful for the treatment of MMVD, CHF and/or asymptomatic heart failure, in an animal, preferably canine.

"Animal(s)", as used herein, unless otherwise indicated, refers to an individual animal that is a mammal. Specifically, mammal refers to a vertebrate animal that is human or non-human, which are members of the taxonomic class Mammalia. Non-exclusive examples of non-human mammals include companion animals. Non-exclusive examples of companion animals include: cat (feline), dog (canine) and horse (equine). The preferred companion animal is canine.

"Asymptomatic (occult, preclinical) heart failure" as used herein, unless otherwise indicated, refers to any contractile disorder or disease of the heart which is due to MMVD.

"Compound(s) of the invention", unless otherwise indicated or claimed, refers to the PDE3 receptor antagonists (inhibitors) that are herein described as Examples #1-89, stereoisomers thereof, and/or veterinary acceptable salts thereof. The compound Example numbers are equivocally correlated with its specific Example name and structure.

"Comprises" or "comprising", as used herein, refers to an inclusive meaning, i.e., that it will be taken to mean an inclusion of not only the listed components it directly references, but also other non-specified components or elements.

"Congestive heart failure", or "heart failure" unless otherwise indicated, refers to a manifested process wherein the heart is unable to keep up with the demands of blood supply to the body and generally results in fluid buildup in the lungs resulting from increased cardiac and pulmonary pressures. The term(s) also relate to any contractile disorder or disease of the heart. Clinical manifestations are as a rule the result of changes to the heart's cellular and molecular components and to mediators that drive homeostatic control that leads to an increase in heart size and deterioration of cardiac function.

"Myxomatous mitral valve disease (MMVD)", unless otherwise indicated, refers to the manifested process of mitral valve degeneration. MMVD is generally detected as a heart murmur by auscultation. MMVD also includes the synonymous medicinal terms including: mitral valve disease (MVD); degenerative mitral valve disease (DMVD); chronic valve disease (CVD); chronic valvular heart disease (CVHD); and atrial ventricular valvular insufficiency (AVVI).

"Stereoisomer(s)" as used herein, refers specifically to those compounds of the invention that possess at least one chiral carbon; and exist as enantiomers (S and R optical isomers) which are mirror images of each other, chemically identical, but non-superimposable. The mixture of the (S) and (R) enantiomers is racemic. For example, Example #33 and Example #51 are the (R) and (S) isomers, respectively, of Example #24 (racemate).

"Therapeutically effective amount", unless otherwise indicated, refers to an amount of a compound of the invention that (i) treats MMVD, CHF and/or asymptomatic heart failure in an animal (ii) attenuates, ameliorates, or eliminates one or more symptoms of MMVD, CHF and/or asymptomatic heart failure in an animal, or (iii) prevents or delays the onset of MMVD, CHF and/or asymptomatic heart failure in an animal.

"Treatment", "treating", "treat", and the like, as used herein, unless otherwise indicated, refers to alleviating, halting, or slowing the progression of MMVD, CHF and/or asymptomatic heart failure in an animal. As used herein, these terms also encompass, depending on the condition of the animal, preventing the onset of a disorder or condition, or of symptoms associated with a disorder or condition, including reducing the severity of a disorder or condition or symptoms associated therewith. Thus, treatment can refer to administration of a compound of the invention to an animal that is not at the time of administration diagnosed with CHF.

"Veterinary acceptable", unless otherwise indicated, refers to a substance or composition that is compatible chemically and/or toxicologically with the animal receiving said substance or composition. The term also contemplates "pharmaceutical or pharmaceutically" acceptable; and is used interchangeably.

As described herein, "and veterinary acceptable salt(s)" also equally describes "or veterinary acceptable salt(s). In some instances, a stereoisomer of the Example or a veterinary acceptable salt of the Example or stereoisomer thereof, can be used in a composition or medicament for treating MMVD, CHF and/or asymptomatic heart failure in an animal.

Myxomatous mitral valve disease (MMVD) is the most common acquired type of heart disease and new heart murmurs in older dogs. A heart murmur is a sound heard with every heartbeat and is caused by turbulent blood flow in the heart. MMVD is a manifestation of a process that can affect the mitral valve. MMVD affects primarily small breed dogs later in life but can affect larger breed dogs. Some smaller breed dogs are affected earlier in life than others with the Cavalier King Charles Spaniel being the most prominent breed described to date.

The mitral valve is the valve between the left atrium and the left ventricle. Oxygenated blood from the lungs enters the left atrium, passes through the mitral valve into the left ventricle and subsequently pumped to the body. The mitral valve closes when the left ventricle contracts which prevents blood from flowing back into the left atrium. A healthy mitral valve is thin and supple and is anchored in place by chordae tendonae (CT). Myxomatous degeneration is a process that occurs when the valve becomes thickened with formation of small nodules which prevent complete closing of the valves allowing back flow (mitral regurgitation) of blood into the left atrium. Over time, the atrium and ventricles compensate by enlarging and the leak progressively worsens. As leaking volume increases, atrial pressure increases. In some instances, CT may rupture causing a partially unanchored mitral valve (mitral valve pro-lapse). The increase in pressure is transmitted to the lungs leading to CHF.

A heart murmur is generally the earliest means by which MMVD can be detected. After the murmur is detected, MMVD symptoms may not appear for three to four years. Often the first outward sign of worsening MMVD is a cough or increased respiratory effort which may be due to airway pressure from the enlarged heart and/or fluid congestion in the lungs, pericardium and heart.

Current medications may slow the progression of MMVD to CHF, particularly in the early stages of the disease. Treatments are administered to manage MMVD, CHF and/or asymptomatic heart failure, including, but not limited to: furosemide, pimobendan, ACE inhibitors (e.g., enalapril) and spironolactone. Furosemide is a potent diuretic that removes water from the body thereby decreasing pulmonary fluid congestion. Pimobendan helps the heart work more effectively, aids in decreasing cardiac remodeling and has been shown to improve survival in MMVD patients. ACE inhibitors and spironolactone block deleterious compensatory mechanisms that occur with severe heart disease and have been shown to prolong survival as well. Side effects of these drugs include allergic reaction, staggering, loss of appetite, lethargy, diarrhea and fainting. Other medications that can be used to manage the symptoms of CHF include hydrochlorothiazide, amlodipine, torsemide and digoxin.

Despite development of new drugs and treatment regimens, uncertainty remains about when to treat and what the best interventions are for some of these animals. In 2009, an objective classification system was developed to categorize heart disease that is based on risk factors and clinical and diagnostic imaging signs.

Heart failure is divided in different stages, which were defined by different classification systems, e.g. the International Small Animal Cardiac Health Council (ISACHC), the New York Heart Association (NYHA) functional classification systems and the currently used classification according to the Consensus Statements of the American College of Veterinary Internal Medicine (ACVIM), 2009. To remove any ambiguity between classification systems, the classification systems described below are to be considered synonymous.

Classification according to the International Small Animal Cardiac Health Council (ISACHC) System: Class I: asymptomatic (also known as occult or preclinical); Class IA: no evidence of compensation for underlying heart disease (no volume overload or pressure overload detected radiographically or echocardiographically); Class IB: clinical signs of compensation for underlying heart disease (volume overload or pressure overload detected radiographically or echocardiographically); Class II: mild to moderate heart failure with clinical signs at rest or with mild exercise (treatment required); Class III: advanced heart failure; clinical signs of severe congestive heart failure; Class IIIA: home treatment possible; and Class IIIB: requires hospitalization.

New York Heart Association (NYHA) functional classification system: Class I: describes patients with asymptomatic heart disease (e.g., chronic valvular heart disease (CVHD) is present, but no clinical signs are evident even with exercise); Class II: describes patients with heart disease that causes clinical signs only during strenuous exercise; Class III: describes patients with heart disease that causes clinical signs with routine daily activities or mild exercise; and Class IV: describes patients with heart disease that causes severe clinical signs even at rest.

The ACVIM system describes four basic stages of heart disease and failure: Stage A: patients at high risk for developing heart disease but that currently have no identifiable structural disorder of the heart; Stage B: patients with structural heart disease (e.g., the typical murmur of mitral valve regurgitation is present), but that have never developed clinical signs caused by heart failure (because of important clinical implications for prognosis and treatment, the panel further subdivided Stage B into Stage B1 and B2). Stage B1: asymptomatic patients that have no radiographic or echocardiographic evidence of cardiac remodeling in response to CVHD. Stage B2: asymptomatic patients that have hemodynamically significant valve regurgitation, as evidenced by radiographic or echocardiographic findings of left sided heart enlargement. Stage C: patients with past or current clinical signs of heart failure associated with structural heart disease. Stage D: patients with end-stage disease with clinical signs of heart failure caused by CVHD that are refractory to standard therapy.

The pathology of the heart begins with ISACHC Class I, NYHA Class I and ACVIM stage B2 in which cardiac murmur or cardiac chamber enlargement, but no clinical symptoms are present (ISACHC Class I or asymptomatic/occult/preclinical stage). Clinical symptoms become manifest in the course of progression of the disease (ISACHC Class II or III, NYHA class II, III or IV, ACVIM stage C and D).

Compounds of the invention have an affinity to PDE3 and may provide a potentially new drug to veterinarians for treating MMVD, CHF and/or asymptomatic heart failure in animals.

The compounds of the invention are useful as PDE3 antagonists for the treatment of MMVP, CHF and/or asymptomatic heart failure in animals, particularly canines. Another aspect of the invention is a veterinary composition comprising a therapeutically effective amount of a compound of the invention, and veterinary acceptable salts thereof. Another aspect of the invention is a veterinary composition comprising a therapeutically effective amount of a compound of the invention, veterinary acceptable salts thereof, and a veterinary acceptable excipient. The compounds of the invention (including the compositions and processes used therein) may also be used in the manufacture of a medicament for the therapeutic applications described herein.

The compounds of the invention can be administered alone or in a formulation appropriate to the specific use envisaged and the species of animal being treated. Generally, it will be administered as a formulation in association with one or more veterinary acceptable excipients. The term "excipient", is used herein to describe any ingredient other than the compound of the invention, or salt thereof, or any additional veterinary agent. The choice of excipient(s) will to a large extent depend on factors such as the particular mode of administration, the effect of the excipient(s) on solubility and stability, and the nature of the dosage form. In addition to the excipient(s), the amount of the compound of the invention that is administered and the dosage regimen for treating a condition or disorder with the compound depends on a variety of factors, including the age, weight, sex and medical condition of the animal, the severity of the disease, the route and frequency of administration, and thus may vary widely.

In one aspect, the veterinary composition comprises a compound of the invention with a veterinary acceptable excipient. The concentration range will vary depending on the composition (e.g., oral or injectable). The range of active (i.e., compound of the invention (e.g., Example #19, #23, #24, #57, #62, #75, and the like) agent is about 0.005 to 10 mg/kg; or about 0.01 to 10 mg/kg; or about 0.1 to 10 mg/kg; or about 0.1 to 5 mg/kg; or about 0.2 to 5 mg/kg; or about 0.2 to about 2.5 mg/kg. The preferable route of administration is oral. The concentration ranges and preferred concentration ranges are considered to be therapeutically effective doses. Further, dose range and preferred dose range can be higher or lower than the concentrations described herein.

The formulations can be prepared using conventional dissolution and mixing procedures. Such compositions and methods for their preparation may be found, for example, in 'Remington's Veterinary Sciences', 19th Edition (Mack Publishing Company, 1995; and "Veterinary Dosage Forms: Tablets, Vol. 1", by H. Lieberman and L. Lachman, Marcel Dekker, N.Y., 1980 (ISBN 0-8247-6918-X).

A typical formulation is prepared by mixing a compound of the invention with at least one veterinary acceptable excipient. Suitable excipients are well known to those skilled in the art and include materials such as carbohydrates, waxes, water soluble and/or swellable polymers, hydrophilic or hydrophobic materials, gelatin, oils, solvents, water, and the like. The particular excipient(s) will depend upon the means and purpose for which the compound of the invention is being applied. Solvents are generally selected based on solvents recognized by persons skilled in the art as safe to be administered to an animal. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents and other known additives to provide an elegant presentation of the drug (i.e., a compound of the invention or veterinary composition thereof) or aid in the manufacturing of the veterinary product (i.e., medicament). The compound of the invention will typically be formulated into veterinary dosage forms to provide an easily controllable dosage form for administration.

The methods by which the compound of the invention may be administered include oral and injectable (e.g., parenteral and subcutaneous).

The compounds of the invention can be administered orally by capsule, bolus, tablet, powders, lozenges, chews, multi and nano-particulates, gels, solid solution, films, sprays, or liquid form. This is a preferred method of administration and as such it is desirable to develop the compound for oral administration. Such formulations may include soft or hard capsules and tablets, soft or hard palatable chews, which typically comprise an excipient, for example, water, ethanol, polyethylene glycol, N-methylpyrrolidone, propylene glycol, methylcellulose, glycerol, magnesium stearate, pregelatinized starch, sodium starch glycolate, animal-based flavorant (chicken, liver, beef, and the like), non-animal based flavorant (e.g., vegetable, fruit, yeast, and the like), and other known pharmaceutical excipients that are designated as fillers, disintegrants, stabilizers, anti-oxidants, preservatives, and the like. Liquid forms include suspensions, solutions, syrups, drenches and elixirs. Liquid formulations may also be prepared by the reconstitution of a solid, for example, from a sachet or lyophilate.

Injectable formulations may be prepared in the form of a sterile solution, which may contain other substances, for example enough salts or glucose to make the solution isotonic with blood. Acceptable liquid excipients include vegetable oils such as sesame oil and cotton seed oil, glycerides such as triacetin, esters such as benzyl benzoate, isopropyl myristate and fatty acid derivatives of propylene glycol, as well as organic solvents such as pyrrolidin-2-one, benzyl alcohol and glycerol formal. The formulations are prepared by dissolving or suspending compounds of the invention alone or with an additional veterinary agent in the liquid excipient(s) such that the final formulation contains from about 0.01 to 30% by weight of the active ingredient.

Suitable devices for injectable administration include needle (including micro needle) injectors, needle-free injectors and infusion techniques. Injectable formulations are typically aqueous solutions which may contain excipients such as salts, carbohydrates and buffering agents (preferably to a pH of from 3 to 9), but, for some applications, they may be more suitably formulated as a sterile non-aqueous solution or as a dry powder form to be used in conjunction with a suitable vehicle such as sterile, pyrogen-free water. The preparation of injectable formulations under sterile conditions, for example, by lyophilization, may readily be accomplished using standard veterinary techniques well known to those skilled in the art. The solubility of a compound of the invention used in the preparation of an injectable solution may be increased by the use of appropriate formulation techniques, such as the incorporation of solubility-enhancing agents.

Administration of the compound of the invention is contemplated to be once or twice daily. Preferably, once a day. Further, the compound of the invention can also be administered once or twice every 2, 3, 4, 5, 6 or 7 days.

The composition of the invention may be administered alone, as described above, or in combination with at least one other additional veterinary agent thereby providing a broader spectrum of veterinary utility. These at least one other additional veterinary agents, including pharmaceutical agents, can be dosed simultaneously with the compound of the invention, or anytime through-out the duration of treatment of the animal.

The following list of additional pharmaceutical (veterinary) cardiovascular agents together with which the compound of the invention can be used to treat cardiac disease (e.g., MMVD, CHF, and/or asymptomatic heart failure) in an animal is intended to illustrate the possible combinations, but not to impose any limitation thereof. Non-limiting examples of additional pharmaceutical (veterinary) agents include: diuretics (e.g., furosemide, chlorothiazide, indapamide, triamterene, hydrochlorothiazide, and the like) to reduce edema and effusion; aldosterone antagonists (e.g., spironolactone, eplerenone, and the like) to reduce aldosterone-mediated myocardial fibrosis, possibly slowing the progression of heart disease and block the reabsorption of sodium which encourages water loss; and an ACE inhibitor (e.g. enalapril, ramipril, benazepril, imidapril, and the like) to inhibit the action of angiotensin-converting enzyme, producing a balanced vasodilation by relaxing blood vessels.

The veterinary composition for application to an animal may be packaged in a variety of ways depending upon the method used for administering the compound of the invention or combination, thereof. Generally, an article for distribution includes a container having deposited therein the veterinary composition in an appropriate form. Suitable containers are well-known to those skilled in the art and include materials such as bottles (plastic and glass), sachets, ampoules, plastic bags, metal cylinders, and the like. The container may also include a tamper-proof assemblage to prevent indiscreet access to the contents of the package. In addition, the container has deposited thereon a label that describes the contents of the container. The label may also include appropriate warnings.

The compounds of the invention (including the compositions and processes used therein) may also be used in the manufacture of a medicament for the therapeutic applications described herein.

The compound structures in the examples below were confirmed by one or more of the following methods: proton magnetic resonance spectroscopy, and mass spectroscopy. Proton magnetic resonance (1H NMR) spectra were determined using a Bruker spectrometer operating at a field strength of 400 megahertz (MHz). Chemical shifts are reported in parts per million (PPM, δ) downfield from an internal tetramethylsilane standard or residual protonated NMR solvents. Mass spectra (MS) data were obtained using an Agilent 1200 Series LC/MS system equipped with an Agilent 6125 or 6140 single quadrupole mass spectrometer and a Waters BEH C8 1.7 μm 2.1×50 mm column using gradient conditions of 0.1% TFA in acetonitrile/water; or similar instrumentation (Waters Acquity or Shimadzu), column (Waters Acquity BEH C8 column, Waters YMC Triart C18, Waters Xbridge C18/Agilent Zorbax C18 or Waters Xbridge C18), and using gradient conditions of mobile phase (A: 0.05% formic acid in water; B: 0.05% formic acid in ACN:water (90:10); or A: 10 mM ammonium acetate in water; B: ACN; or A: 5 mM ammonium acetate in water; B: 5 mM ammonium acetate in ACN:water (90:10); or A: 0.1% formic acid in water; B: 0.1% formic acid in ACN). Compounds of the invention may be synthesized by synthetic routes that include processes analogous to those well known in the chemical arts, particularly in light of the description contained herein. The starting materials are generally available from commercial sources such as Aldrich Chemicals (Milwaukee, Wis.) or are readily prepared using methods well known to those skilled in the art (e.g., prepared by methods generally described in Louis F. Fieser and Mary Fieser, "Reagents for Organic Synthesis", 1; 19, Wiley, New York (1967, 1999 ed.), or Beilsteins Handbuch der organischen Chemie, 4, Aufl. ed. Springer-Verlag, Berlin, including supplements (also available via the Beilstein online database)). For illustrative purposes, the reaction schemes depicted below demonstrate potential routes for synthesizing compounds of the invention, and key intermediates. A more detailed description of the individual reaction steps can be found in the Examples section. The skilled person will appreciate that the compounds of the invention could be made by methods other than those herein described by adaptation of the methods herein described and/or adaptation of methods known in the art, for example the art described herein, or using standard textbooks such as "Comprehensive Organic Transformations—A Guide to Functional Group Transformations", RC Larock, Wiley-VCH (1999 or later editions).

Many of the compounds of the present invention described herein contain at least one asymmetric or chiral center; and therefore, exist in different stereoisomeric forms. Chirality refers to the structural characteristic of a molecule that makes it impossible to superimpose it on its mirror image, (e.g., "R" and "S" enantiomers). Example numbers 7, 9, 15, 25, 27, 32, 44, 52, 59, 61, 66, 72, 84-86 and 88-89 do not contain a chiral carbon. The R and S configurations are based upon knowledge of known chiral inversion/retention chemistry. Unless specified otherwise, it is intended that the stereoisomeric forms of the compounds of the invention as well as racemic mixtures thereof, form part of the present invention. Racemic mixtures of enantiomers can be separated into their individual enantiomeric forms by the skilled artisan on the basis of their physical chemical differences by methods well known to those skilled in the art, such as chromatography and/or fractional crystallization. A more detailed description of techniques that can be used to resolve stereoisomers of compounds from their racemic mixture can be found in Jean Jacques Andre Collet, Samuel H. Wilen, Enantiomers, Racemates and Resolutions, John Wiley and Sons, Inc. (1981). One skilled in the art will appreciate that one stereoisomer may be more active and/or may exhibit beneficial effects when enriched relative to the other stereoisomeric form when separated from the racemic mixture.

The examples and general procedures useful for the preparation and isolation of compounds of the invention are described herein. It is to be understood, however, that the invention, as fully described herein and as recited in the claims, is not intended to be limited by the details of the following schemes or modes of preparation. In the schemes and examples described herein, the following reactants and miscellaneous abbreviations include: acetic acid (AcOH); acetonitrile (Acn or MeCN); aluminum chloride ($AlCl_3$); carbonyldiimidazole (CDI); dichloromethane (DCM); $CH_2CL_2$); N, N-dimethylformamide (DMF); dimethylsulfoxide (DMSO); 1,1'-bis(diphenylphosphino)ferrocene (dppf); ethyl acetate (EtOAc); ethanol (EtOH); ethylmagnesium bromide (EtMgBr); [dimethylamino(triazolo[4,5-b]pyridin-3-yloxy)methylidene]-dimethyl-azanium hexafluorophosphate (HATU); hydrochloric acid (HCl); high pressure liquid chromatography (HPLC); isopropylmagnesium-chloride·lithium chloride (iPrMgCl·LiCl); potassium carbonate ($K_2CO_3$); tripotassium phosphate ($K_3PO_4$); potassium bis(trimethylsilyl)amide (KHMDS); potassium acetate (KOAc); potassium thiocyanate (KSCN); lithium borohydride ($LiBH_4$); liquid chromatography mass spectrometry (LCMS); lithium bis(trimethylsilyl)amide (LiHMDS); lithium hydroxide (LiOH); methanol (MeOH); 2-methyltetrahydrofuran (MeTHF); sodium carbonate ($Na_2CO_3$); sodium bicarbonate ($NaHCO_3$); sodium nitrite ($NaNO_2$); sodium sulfate ($Na_2SO_4$); N-bromosuccinimide (NBS); n-butyllithium (n-Buli); N-chlorosuccinimide (NCS); hydrazine ($NH_2NH_2$); nuclear magnetic resonance (NMR); N,N-diisopropylethylamine (DIPEA); p-methoxybenzyl (PMB); room temperature (RT); triethylamine (TEA); trifluoroacetic acid (TFA); tetrahydrofuran (THF); thin layer chromatography (TLC); palladium (Pd); palladium on carbon (Pd/C); [1,1'-bis(diphenylphosphino)ferrocene]-dichloropalladium(II) (Pd(dppf)$Cl_2$); tris(dibenzylideneacetone) dipalladium(0) ($Pd_2(dba)_3$); [1,1'-Bis(di-tert-butylphosphino)-ferrocene]dichloropalladium(II) (Pd-118, Pd(dtbpf)$Cl_2$); [1,1'-bis(diphenyl-phosphino)ferrocene]-dichloropalladium(II) complex with dichloromethane (1:1; Pd(dppf)$Cl_2$·DCM); potassium tert-butoxide (t-BuOK); tri-tert-butylphosphine ($P(tBu)_3$)); water ($H_2O$); 2-dicyclohexylphosphino-2',4',6'-triisopropylbiphenyl (XPhos); 2-dicyclohexylphosphino-2',4',6'-triisopropylbiphenyl[2-(2'-amino-1,1'biphenyl)]palladium(II) methane sulfonate (XPhos Pd G3); and zinc cyanide ($Zn(CN_2)$).

The veterinary acceptable salts of compounds of the invention may also be prepared in a conventional manner. For example, a solution of a free base may be treated with the appropriate acid, either neat or in a suitable solvent, and the resulting salt isolated either by filtration or by evaporation under reduced pressure of the reaction solvent. For a review on suitable salts, see "Handbook of Pharmaceutical Salts: Properties, Selection, and Use" by Stahl and Wermuth (Wiley-VCH, Weinheim, Germany, 2002).

The compound of the invention may be used in its native form or as a salt. In cases where forming a stable nontoxic acid or base salt is desired, administration of the compound as a veterinary acceptable salt may be appropriate. Veterinary acceptable salts of the compounds of the invention include, but are not limited to: acetate, ascorbate, aspartate, benzoate, besylate, bicarbonate/carbonate, bisulphate/sulphate, borate, camsylate, citrate, edisylate, etoglutarate, esylate, formate, fumarate, gluceptate, gluconate, glucuronate, glycerophosphate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, saccharate, stearate, succinate, tartrate, tosylate, and trifluoroacetate salts.

For illustrative purposes, the reaction schemes depicted below demonstrate potential routes for synthesizing the compounds of the invention. Those skilled in the art will appreciate that other suitable starting materials, reagents and synthetic routes may be used to prepare the intermediates and compounds of the invention.

EXAMPLES

The following examples provide a more detailed description of each compound and the process conditions for preparing said compounds of the invention. It is to be understood, however, that the invention as fully described herein and as recited in the claims, is not intended to be limited by the details of the following modes of preparation. Examples #35 and #40 exist as tautomers wherein the hydrogen atom and double bond of the quinolinyl ring interconvert spontaneously and are in a state of equilibrium.

Preparation of Example #3 (8-bromo-6-(4-methyl-6-oxo-1,4,5,6-tetrahydropyridazin-3-yl)-3,4-dihydroquinolin-2(1H)-one) and Example #12 (8-(3-fluorophenyl)-6-(4-methyl-6-oxo-1,4,5,6-tetrahydropyridazin-3-yl)-3,4-dihydroquinolin-2(1H)-one)

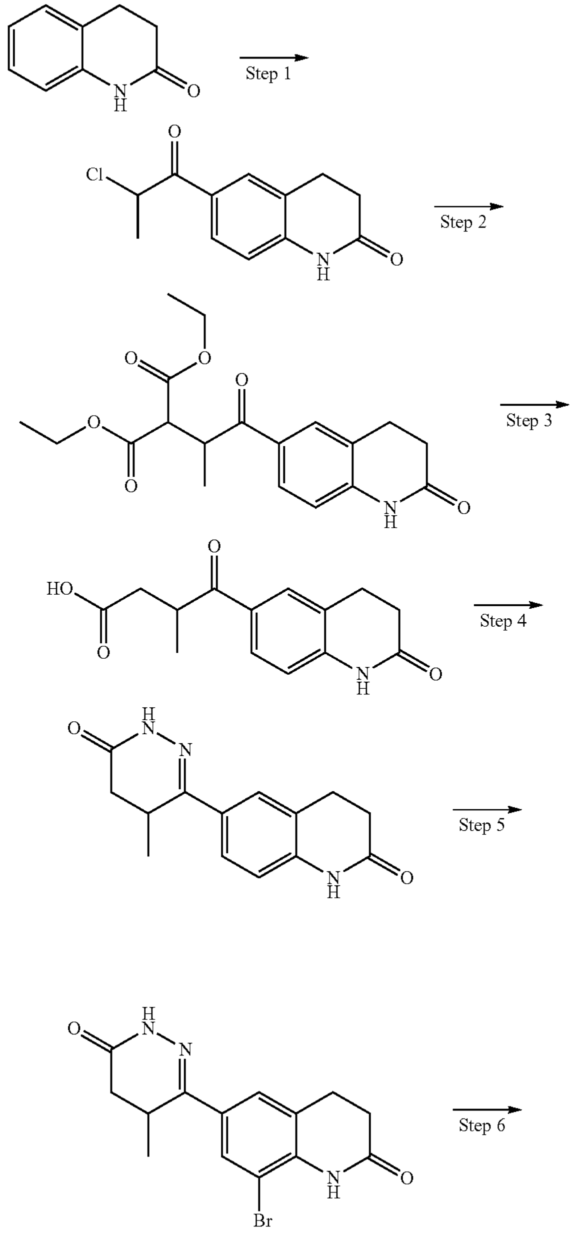

(3)

-continued

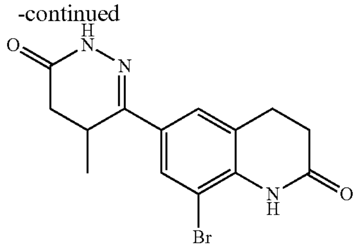

(12)

Step 1: To a 1,2-dichloroethane (25 mL) solution of 3,4-dihydroquinolin-2(1H)-one (2.5 g, 17 mmol) was added 2-chloropropanoyl chloride (4.25 g, 34 mmol, 2 eq) followed by the addition of aluminum trichloride (9 g, 68 mmol, 4 eq) in three equal portions over 10 minutes while stirring. The mixture in an inert atmosphere of nitrogen was then heated to 50° C. After 3.5 hours the reaction was judged complete based on LCMS analysis. The reaction mixture was poured directly into a beaker of ice. After the ice melted the mixture was poured into a separatory funnel. Methylene chloride (100 mL) was added, and the product was extracted. The organic phase was again washed with saturated aqueous $NaHCO_3$ (1×50 mL) and brine (1×50 mL). The organic layer was dried and concentrated to give 6-(2-chloropropanoyl)-3,4-dihydroquinolin-2(1H)-one (2.75 g, 11.6 mmol) which was used directly in the next step.

Step 2: Potassium tert-butoxide (1.7 g, 15.1 mmol) was added in three equal portions over 20 minutes to a stirring solution of DMSO (40 mL). The mixture was allowed to stir for an additional 20 minutes. A solution of diethylmalonate (2.4 g, 15.1 mmol) in DMSO (5 mL) was added dropwise over 10 minutes. The solution was stirred for 20 minutes before the addition of 6-(2-chloropropanoyl)-3,4-dihydroquinolin-2(1H)-one (2.75 g, 11.6 mmol) as a solution in DMSO (10 mL). The reaction mixture was then warmed to 35° C. and stirred for 3 hours. The mixture was cooled to room temperature and acetic acid (1.2 g, 20 mmol) was added. The mixture was then partitioned between ethyl acetate (150 mL) and water (100 mL). The organic layer was washed with water (4×70 mL). The organic phase was dried ($Na_2SO_4$) and concentrated to give crude diethyl 2-(1-oxo-1-(2-oxo-1,2,3,4-tetrahydroquinolin-6-yl)propan-2-yl)malonate (3.5 g, 9.7 mmol).

Step 3: To diethyl 2-(1-oxo-1-(2-oxo-1,2,3,4-tetrahydroquinolin-6-yl)propan-2-yl)malonate (3.5 g, 9.7 mmol) was added 6N HCl (100 mL) and dioxane (20 mL). The reaction was then heated at 90° C. for 16 hours. The reaction mixture was poured into a beaker of ice water. Once the ice melted, the mixture was poured into a separatory funnel and the product was extracted using methylene chloride (4×50 mL). The combined organic washes were dried over sodium sulfate and concentrated to give crude 3-methyl-4-oxo-4-(2-oxo-1,2,3,4-tetrahydroquinolin-6-yl)butanoic acid (1.8 g, 6.9 mmol).

Step 4: Ethanol (30 mL) was added to 3-methyl-4-oxo-4-(2-oxo-1,2,3,4-tetrahydroquinolin-6-yl)butanoic acid (1.8 g, 6.9 mmol) followed by addition of hydrazine monohydrate (1.75 g, 35 mmol). The solution was heated at 65° C. for 4 hours. The mixture was poured into ice water (200 mL) causing a beige precipitate to form. The precipitate was collected using suction filtration to provide the product, 6-(4-methyl-6-oxo-1,4,5,6-tetrahydropyridazin-3-yl)-3,4-dihydroquinolin-2(1H)-one (1.35 g, 5.2 mmol) upon drying.

Step 5: To a DMF (20 mL) solution of 6-(4-methyl-6-oxo-1,4,5,6-tetrahydropyridazin-3-yl)-3,4-dihydroquinolin-2(1H)-one (1.35 g, 5.2 mmol) was added NBS (1.1 g, 6.2 mmol). The mixture was stirred at 55° C. for 10 hours. A second portion of NBS (0.55 g, 3.1 mmol) was added with stirring a 55° C. for 3 more hours. The reaction was then poured into ice water (150 mL). The beige precipitate was collected by suction filtration and washed with water (3×50 mL). Upon drying, the crude product, 8-bromo-6-(4-methyl-6-oxo-1,4,5,6-tetrahydropyridazin-3-yl)-3,4-dihydroquinolin-2(1H)-one (Example #3; 1.45 g, 4.3 mmol) was obtained. Pure product was obtained using flash column chromatography (3.5% MeOH in $CH_2Cl_2$). 1H NMR (400 MHz, DMSO-d6): δ 10.97 (s, 1H), 9.31 (s, 1H), 7.82 (d, 1H), 7.65 (d, 1H), 3.34-3.45 (m, 1H), 2.98 (t, 2H), 2.67 (dd, 1H), 2.52-2.55 (m, 2H), 2.18-2.28 (m, 1H), 1.05 (d, 3H).

Step 6: To 8-bromo-6-(4-methyl-6-oxo-1,4,5,6-tetrahydropyridazin-3-yl)-3,4-dihydroquinolin-2(1H)-one, (120 mg, 0.36 mmol) was added dioxane (4 mL) and water (0.5 mL). Next, (3-fluorophenyl)boronic acid (80 mg, 0.57 mmol) and sodium hydrogen carbonate (165 mg, 1.9 mmol) were added. The mixture was then degassed by several vacuum purges, refilling with nitrogen. Finally, 1,1-Bis(diphenylphosphino)-ferrocene]dichloropalladium(II) (60 mg, 0.06 mmol) was added. The mixture was then heated at 75° C. for 3 hours. The reaction was filtered through a Celite plug. The plug was washed with methylene chloride (20 mL). The organic phase was washed with water (1×10 mL). The organic phase was concentrated. The crude residue was dissolved in DMF (4.5 mL) and purified using reverse phase HPLC to afford the Example #12 compound (68 mg, 0.18 mmol) after lyophilization. 1H NMR (400 MHz, DMSO-d6): δ 10.92 (s, 1H), 9.03 (s, 1H), 7.68 (s, 1H), 7.54-7.48 (m, 2H), 7.27-7.23 (m, 3H), 3.44-3.40 (m, 1H), 2.99-2.96 (m, 2H), 2.68-2.62 (m, 1H), 2.55-2.50 (m, 2H), 2.39-2.19 (m, 1H), 1.06 (d, J=7.2 Hz, 3H). LCMS: Retention time=2.51 minutes; HPLC purity=98.20%

Preparation of Example #1, 8-(2-methoxypyridin-4-yl)-6-(4-methyl-6-oxo-1,4,5,6-tetrahydropyridazin-3-yl)-3,4-dihydroquinolin-2(1H)-one, was conducted in a similar fashion to Example #12 but for using (2-methoxypyridin-4-yl) boronic acid instead of (3-fluorophenyl)boronic acid in Step 6 to afford the Example #1 compound. 1H NMR (400 MHz, DMSO-d6): δ 10.92 (s, 1H), 9.23 (s, 1H), 8.24 (d, 1H), 7.83-7.60 (m, 1H), 7.01 (dd, 1H), 7.49 (d, 1H), 4.39 (br s, 1H), 6.85 (s, 1H), 3.90 (s, 3H), 3.43-3.22 (m, 1H), 2.98 (br t, 2H), 2.66 (dd, 1H), 2.58-2.52 (m, 1H), 2.22 (d, 1H), 1.06 (d, 3H).

Preparation of Example #2, 6-(4-methyl-6-oxo-1,4,5,6-tetrahydropyridazin-3-yl)-8-(thiazol-2-yl)-3,4-dihydroquinolin-2(1H)-one, was conducted in a similar fashion to Example #12 but for using thiazol-2-ylboronic acid instead of (3-fluorophenyl)boronic acid in Step 6 to afford the Example #2 compound. 1H NMR (400 MHz, DMSO-d6): δ 11.12 (s, 1H), 10.95 (s, 1H), 9.43 (d, 1H), 8.42 (d, 1H), 8.13-7.93 (m, 1H), 7.72-7.67 (m, 1H), 3.66-3.39 (br, m, 1H), 3.03 (t, 2H), 2.70 (dd, 1H), 2.61-2.52 (m, 1H), 1.30 (br d, 1H), 1.09 (d, 3H).

Preparation of Example #4, 8-(2-methoxythiazol-5-yl)-6-(4-methyl-6-oxo-1,4,5,6-tetrahydropyridazin-3-yl)-3,4-dihydroquinolin-2(1H)-one, was conducted in a similar fashion to Example #12 but for using 2-methoxythiazol-5-yl boronic acid instead of (3-fluorophenyl)boronic acid in Step 6 to afford the Example #4 compound. 1H NMR (400 MHz, DMSO-d6): δ 10.93 (s, 1H), 9.38 (s, 1H), 7.82-7.61 (m, 1H), 7.55 (d, 1H), 7.26 (s, 1H), 4.07 (s, 3H), 3.57-3.37 (m, 2H), 3.07-2.85 (m, 2H), 2.80-2.59 (m, 1H), 2.58-2.52 (m, 1H), 2.23 (d, 1H), 1.06 (d, 3H).

Preparation of Example #13, 6-(4-methyl-6-oxo-1,4,5,6-tetrahydropyridazin-3-yl)-8-(pyridin-3-yl)-3,4-dihydroquinolin-2(1H)-one, was conducted in a similar fashion to Example #12 but for using 3-pyridinyl boronic acid instead of (3-fluorophenyl)boronic acid in Step 6 to afford the Example #13 compound. 1H NMR (400 MHz, DMSO-d6): δ 10.91 (s, 1H). 9.34 (s, 1H), 8.64-8.53 (m, 2H), 7.90-7.75 (m, 1H), 7.74-7.61 (m, 1H), 7.60-7.36 (m, 2H), 3.66-3.39 (m, 2H), 3.17-2.90 (m, 2H), 2.82-2.60 (m, 1H), 2.56-2.51 (m, 1H), 2.22 (d, 1H), 1.07 (d, 3H).

Preparation of Example #17, 3,3-dimethyl-5-(4-methyl-6-oxo-1,6-dihydropyridazin-3-yl)-7-(thiazol-4-yl)indolin-2-one, was conducted in a similar fashion to Example #12, Step 6, but for thiophene-4-boronic acid instead of (3-fluorophenyl)boronic acid and Example #47 instead of 8-bromo-6-(4-methyl-6-oxo-1,4,5,6-tetrahydropyridazin-3-yl)-3,4-dihydroquinolin-2(1H)-one to afford the Example #17 compound. 1H NMR (400 MHz, DMSO-d6): δ 10.91 (s, 1H), 10.12 (s, 1H), 9.29 (s, 1H), 8.35 (s, 1H), 8.09 (s, 1H), 7.78 (s, 1H), 3.57-3.54 (m, 1H), 2.74-2.68 (m, 1H), 2.32-2.24 (m, 1H), 1.34 (s, 6H), 1.10 (d, J=7.2 Hz, 3H).

Preparation of Example #18, 9-(6-methoxypyridin-3-yl)-7-(4-methyl-6-oxo-1,4,5,6-tetrahydropyridazin-3-yl)-1,3,4,5-tetrahydro-2H-benzo[b]azepin-2-one, was conducted in a similar fashion to Example #12, Step 6, but for using (2-methoxypyridin-5-yl)boronic acid and 9-bromo-7-(4-methyl-6-oxo-1,4,5,6-tetrahydropyridazin-3-yl)-1,3,4,5-tetrahydro-2H-benzo[b]azepin-2-one to afford the Example #18 compound. 1H NMR (400 MHz, DMSO-d6): δ 8.96 (s, 1H). 8.21-8.14 (d, 1H), 7.76-7.70 (m, 2H), 7.61-7.56 (d, 1H), 6.94-6.87 (d, 1H), 3.92-3.87 (s, 3H), 3.50-3.42 (m, 1H), 3.05-3.00 (m, 1H), 2.81-2.74 (br, t, 2H), 2.73-2.64 (dd, 1H), 2.30-2.24 (m, 2H), 2.19-2.10 (m, 2H), 1.76-1.71 (m, 1H), 1.07-1.11 (d, 3H).

Preparation of Example #63, 6-methyl-5-(7-(4-(methylsulfonyl)phenyl)-2-oxoindolin-5-yl)-3,6-dihydro-2H-1,3,4-thiadiazin-2-one, was conducted in a similar fashion to Example #12 but for (4-(methylsulfonyl)phenyl)boronic acid instead of (3-fluorophenyl)boronic acid in Step 6 and 5-(7-bromo-2-oxoindolin-5-yl)-6-methyl-3,6-dihydro-2H-1,3,4-thiadiazin-2-one instead of 8-bromo-6-(4-methyl-6-oxo-1,4,5,6-tetrahydropyridazin-3-yl)-3,4-dihydroquinolin-2(1H)-one to afford the Example #63 compound. 1H NMR (400 MHz, DMSO-d6): δ 11.62 (s, 1H), 10.63 (brs, 1H), 8.01 (d, J=8.0 Hz, 2H), 7.79-7.77 (m, 3H), 7.66 (s, 1H), 4.85-4.80 (m, 1H), 3.64 (s, 2H), 3.26 (s, 3H), 1.48 (d, J=7.2 Hz, 3H).

Preparation of Example #68, 5-(3,3-dimethyl-2-oxo-7-(thiazol-4-yl)indolin-5-yl)-6-methyl-3,6-dihydro-2H-1,3,4-thiadiazin-2-one, was conducted in a similar fashion to Example #12 but for 4-thiazol-boronic acid instead of (3-fluorophenyl)boronic acid and Example 76 instead of 8-bromo-6-(4-methyl-6-oxo-1,4,5,6-tetrahydropyridazin-3-yl)-3,4-dihydroquinolin-2(1H)-one in Step 6 to afford the Example #68 compound. 1H NMR (400 MHz, DMSO-d6): δ 11.65 (s, 1H), 10.17 (s, 1H), 9.30 (d, J=1.8 Hz, 1H), 8.36 (d, J=1.8 Hz, 1H), 8.14 (d, J=1.6 Hz, 1H), 7.80 (d, J=1.6 Hz, 1H), 4.92-4.82 (m, 1H), 1.51 (d, J=7.2 Hz, 3H), 1.35 (s, 6H).

Preparation of Example #71, 5-(7-(4-chlorophenyl)-2-oxoindolin-5-yl)-6-methyl-3,6-dihydro-2H-1,3,4-thiadiazin-2-one, was conducted in a similar fashion to Example #12 but for 4-chlorophenyl-boronic acid instead of (3-fluorophenyl)boronic acid and 5-(7-bromo-2-oxoindolin-5-yl)-6-methyl-3,6-dihydro-2H-1,3,4-thiadiazin-2-one instead of 8-bromo-6-(4-methyl-6-oxo-1,4,5,6-tetrahydropyridazin-3-yl)-3,4-dihydroquinolin-2(1H)-one in Step 6 to afford the Example #71 compound. 1H NMR (400 MHz, DMSO-d6): δ 11.59 (s, 1H), 10.53 (s, 1H), 7.71 (s, 1H), 7.60 (s, 1H), 7.52 (s, 4H), 4.83-4.78 (m, 1H), 3.62 (s, 2H), 1.47 (d, J=7.2 Hz, 3H).

Preparation of Example #6, 7-chloro-5-(4-methyl-6-oxo-1,4,5,6-tetrahydropyridazin-3-yl)indolin-2-one was prepared according to the following steps:

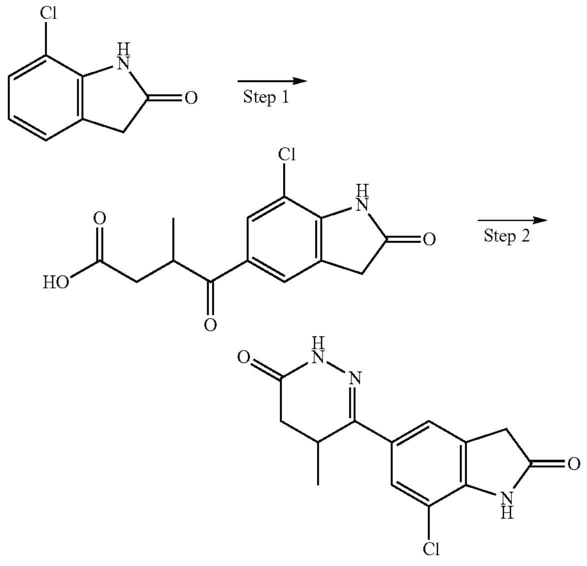

(6)

Step 1: A slurry of $AlCl_3$ (7.9 g, 59.39 mmol) and DMF (1.4 ml, 18.02 mmol) was heated at 70° C. for 15 minutes then cooled to 40° C. 7-chloro-2,3-dihydro-1H-indol-2-one (1.0 g, 5.98 mmol) and 3-methyloxolane-2,5-dione (886 mg, 7.78 mmol) were slowly added. The resulting mixture was heated at 70° C. for 1 hour, poured into ice cooled water and extracted with ethyl acetate. Combined organic layer was washed with brine, dried over anhydrous sodium sulphate, filtered and concentrated under reduced pressure. Crude product thus obtained was triturated with diethyl ether-pentane to afford 4-(7-chloro-2-oxoindolin-5-yl)-3-methyl-4-oxobutanoic acid (800 mg, 47%) as brown gum. It was carried to the next step without further purification. MS (ESI): m/z 282.0 [M+1]+.

Step 2: To a stirred solution of 4-(7-chloro-2-oxoindolin-5-yl)-3-methyl-4-oxobutanoic acid (400.0 mg, 1.42 mmol) in ethanol (20.0 mL) was added hydrazine mono hydrate (0.27 ml, 5.69 mmol). Resulting mixture was heated at 80° C. for 16 hours. Crude LCMS showed formation of two peaks with product mass (undesired:desired=4:1). Reaction mixture was evaporated under reduced pressure, residue was taken up in EtOH and stirred under cooling. Solid thus formed was filtered and discarded [contains major undesired isomer]. Filtrate was concentrated under reduced pressure and crude mass was purified by combiflash column chromatography (60-70% EtOAc in hexane) followed by reverse phase preparative HPLC to afford the Example #6 compound (40 mg, 10%) as an off-white solid. 1H NMR (400 MHz, DMSO-d6): δ 10.95 (s, 1H), 10.92 (s, 1H), 7.62-760 (m, 2H), 3.64 (s, 2H), 3.38-3.34 (m, 1H), 2.69-2.63 (m, 1H), 2.22 (d, J=16 Hz, 1H), 1.04 (d, J=8 Hz, 3H).

Preparation of Example #44 (7-chloro-3,3-dimethyl-5-(6-oxo-1,4,5,6-tetrahydropyridazin-3-yl)indolin-2-one), was conducted in a similar fashion to Example #6, but for 7-chloro-2,3-dimethyl-1H-indol-2-one instead of 7-chloro-2,3-dihydro-1H-indol-2-one and succinic anhydride instead of 3-methyloxolane-2,5-dione to afford the Example #44 compound. 1H NMR (400 MHz, DMSO-d6): δ 10.94 (s, 1H), 10.87 (s, 1H), 7.68 (s, 1H), 7.60 (s, 1H), 2.93 (t, 2H), 2.43 (t, 2H), 1.30 (s, 6H).

Preparation of Example #39 (7-chloro-5-(4-methyl-6-oxo-1, 4, 5, 6-tetrahydropyridazin-3-yl)-2, 3-dihydro-1H-isoindol-1-one)

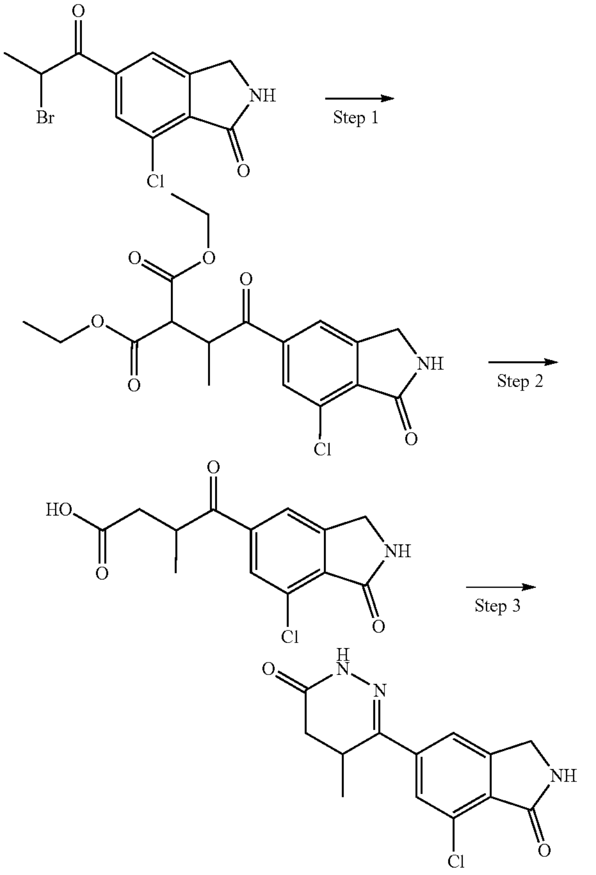

(39)

Step 1. To a stirred solution of potassium tert-butoxide (38.7 mg, 0.35 mmol) in dimethyl sulfoxide (5 mL) was added a solution of diethyl malonate (58 mg, 0.35 mmol) in DMSO (1 mL) drop wise over 10 minutes and stirred at room temperature for 40 minutes. A solution of 5-(2-bromopropanoyl)-7-chloro-2,3-dihydro-1H-isoindol-1-one (80 mg, 0.27 mmol) in DMSO (1 mL) was added drop wise over 10 minutes at 0° C. under argon atmosphere. Resulting mixture was slowly warmed to room temperature and stirred for 3 hours. After completion, reaction mixture was quenched with saturated aqueous ammonium chloride solution at 0° C. and extracted with ethyl acetate. Combined organic layer was washed with brine, dried over anhydrous sodium sulphate, filtered and concentrated under reduced pressure. Crude product was purified by combiflash chromatography (30-50% EtOAc in hexane) to afford 1, 3-diethyl 2-[1-(7-chloro-1-oxo-2,3-dihydro-1H-isoindol-5-yl)-1-oxopropan-2-yl]propanedioate (55 mg, 54%) as yellow solid. MS (ESI): m/z 382[M+1]+.

Step 2. A solution of diethyl 1,3-diethyl 2-[1-(7-chloro-1-oxo-2,3-dihydro-1H-isoindol-5-yl)-1-oxopropan-2-yl] propanedioate (220 mg, 0.58 mmol) in 6N aqueous hydrochloric acid (8 mL) was heated at 90° C. for 16 hours. After completion, volatiles were removed under reduced pressure and the residue was co-distilled with toluene for twice. Crude product was triturated with diethyl ether to obtain 4-(7-chloro-1-oxo-2,3-dihydro-1H-isoindol-5-yl)-3-methyl-4-oxobutanoic acid (90 mg, 55%) as brown gum which was carried to the next step without further purification. MS (ESI): m/z 282.0 [M+1]+.

Step 3. To a stirred solution of 4-(7-chloro-1-oxo-2,3-dihydro-1H-isoindol-5-yl)-3-methyl-4-oxobutanoic acid (80.0 mg, 0.28 mmol) in ethanol (10 mL) was added hydrazine mono hydrate (0.1 ml, 1.14 mmol) at room temperature. Resulting mixture was heated at 90° C. for 16 hours. After completion, volatiles were removed under reduced pressure and obtained crude product was purified by reverse phase preparative HPLC to afford the Example #39 compound (9 mg) as off-white solid (99.89% purity). 1H NMR (400 MHz, DMSO-d6): δ 11.17 (s, 1H), 8.74 (s, 1H), 7.90 (s, 1H), 7.80 (s, 1H), 4.37 (s, 2H), 3.46-3.43 (m, 1H), 2.77-2.66 (m, 1H), 2.32-2.25 (m, 1H), 1.08 (d, J=7.2 Hz, 3H).

Preparation of Example #7, 7-(4-chlorophenyl)-5-(6-oxo-1,6-dihydropyridazin-3-yl)indolin-2-one, was prepared according to the following steps:

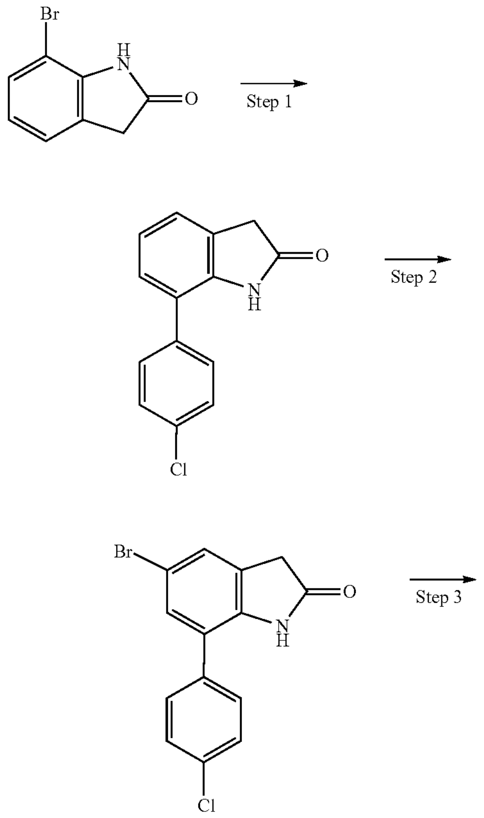

-continued

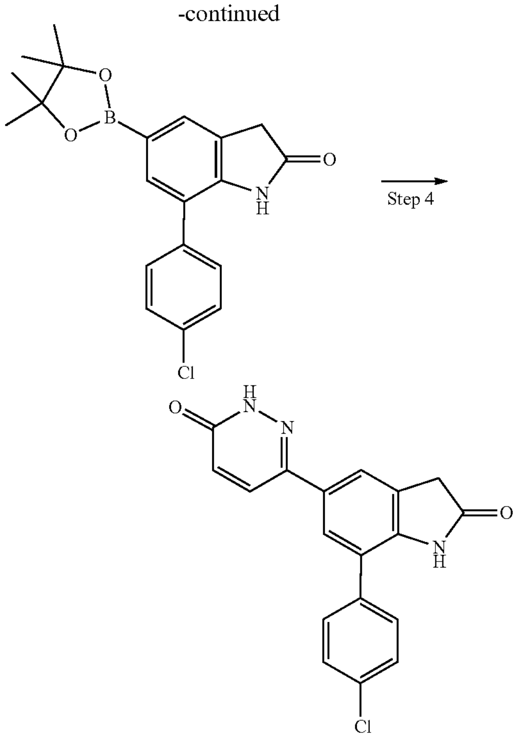

(7)

Step 1: To a stirred solution of 7-bromo-2,3-dihydro-1H-indol-2-one (200.0 mg, 0.94 mmol) in 1,4-dioxane (5.0 ml) and water (2.0 ml) was added potassium phosphate (500 mg, 2.36 mmol) followed by 4-chlorophenyl boronic acid (222 mg, 1.42 mmol) and resulting mixture was purged with argon for 10 minutes. $Pd(dppf)Cl_2 \cdot CH_2Cl_2$ (77.0 mg, 0.09 mmol) was added and reaction mixture was heated at 100° C. for 16 hours. After completion, reaction mixture was diluted with water and extracted with ethyl acetate. Combined organic layer was washed with brine, dried over anhydrous sodium sulphate, filtered and concentrated under reduced pressure. Crude product was purified by combiflash column chromatography (10-15% EtOAc in hexane) to afford 7-(4-chlorophenyl)-2,3-dihydro-1H-indol-2-one (160 mg, 70%) as brown solid. MS (ESI): m/z 244.02 [M+1]+.

Step 2: To a stirred solution of 7-(4-chlorophenyl)-2,3-dihydro-1H-indol-2-one (100.0 mg, 0.41 mmol) in trifluoroacetic acid (3.0 ml) was added N-bromo succinimide (52.0 mg, 0.53 mmol) portion wise and reaction mixture was stirred at room temperature for 16 hours. After completion, volatiles were removed under reduce pressure. Residue was diluted with water and extracted with ethyl acetate. Organic layer was dried over anhydrous sodium sulphate, filtered and concentrated under reduce pressure. Crude mass was purified by combiflash column chromatography (10-15% EtOAc in hexane) to afford 5-bromo-7-(4-chlorophenyl)-2,3-dihydro-1H-indol-2-one (60 mg, 45%) as off-white solid. MS (ESI): m/z 323.8 [M+1]+.

Step 3: To a stirred solution of 5-bromo-7-(4-chlorophenyl)-2,3-dihydro-1H-indol-2-one (250.0 mg, 0.77 mmol) in 1,4-dioxane (5.0 ml) was added bis(pinacolato)-diboron (238 mg, 0.93 mmol) followed by potassium acetate (153 mg, 1.55 mmol) and resulting mixture was purged with argon for 10 minutes. $Pd(dppf)Cl_2 \cdot CH_2Cl_2$ (64 mg, 0.07 mmol) was added and reaction mixture was heated at 85° C. for 16 hours. After completion, reaction mixture was diluted with water and extracted with ethyl acetate. Combined organic layer was washed with brine, dried over anhydrous sodium sulphate, filtered and concentrated under reduced pressure. Crude mass was purified by combiflash column chromatography (30-40% EtOAc in hexane) to afford 7-(4-chlorophenyl)-5-(tetramethyl-1,3,2-dioxaborolan-2-yl)-2,3-dihydro-1H-indol-2-one (200 mg, 69%) as off-white solid. MS (ESI): m/z 370.3 [M+1]+.

Step 4: To a stirred solution of 7-(4-chlorophenyl)-5-(tetramethyl-1,3,2-dioxaborolan-2-yl)-2,3-dihydro-1H-indol-2-one (200.0 mg, 0.54 mmol) in 1,4-dioxane (10.0 ml) and water (2.0 ml) was added potassium phosphate (288.0 mg, 1.35 mmol) followed by 6-bromo-2,3-dihydro-pyridazin-3-one (143.0 mg, 0.81 mmol) and resulting mixture was purged with argon for 10 minutes. Pd(dppf) $Cl_2 \cdot CH_2Cl_2$ (44.0 mg, 0.05 mmol) was added and reaction mixture was heated at 100° C. for 16 hours. After completion, reaction mixture was diluted with water and extracted with ethyl acetate. Combined organic layer was washed with brine, dried over anhydrous sodium sulphate, filtered and concentrated under reduced pressure. Crude product was purified by combiflash column chromatography (50-60% EtOAc in hexane) to afford the Example #7 compound (10 mg, 6%) as an off-white solid. 1H NMR (400 MHz, DMSO-d6): δ 13.10 (s, 1H), 10.49 (s, 1H), 8.01 (s, 1H), 7.74 (s, 1H), 7.65 (s, 1H), 7.52 (s, 4H), 6.95 (d, J=10 Hz, 1H), 3.63 (s, 2H).

Preparation of Example #9, 8-(4-chlorophenyl)-6-(6-oxo-1,6-dihydropyridazin-3-yl)-3,4-dihydroquinolin-2(1H)-one, was conducted in a similar fashion to Example #7 but for 6-bromo-3,4-hydro-quinolone instead of 7-bromo-2,3-dihydro-1H-indol-2-one to afford the Example #9 compound. 1H NMR (400 MHz, DMSO-d6): δ 13.11 (s, 1H), 9.01 (s, 1H), 8.08 (d, J=9.6 Hz, 1H), 7.76 (s, 1H), 7.55-7.53 (m, 3H), 7.46-7.44 (m, 2H), 6.96 (d, J=9.6 Hz, 1H), 3.01-2.98 (m, 2H), 2.52-2.48 (m, 2H).

Preparation of Example #8, 7'-chloro-5'-(4-methyl-6-oxo-1,4,5,6-tetrahydropyridazin-3-yl)spiro[cyclopropane-1,3'-indolin]-2'-one, was prepared according to the following steps:

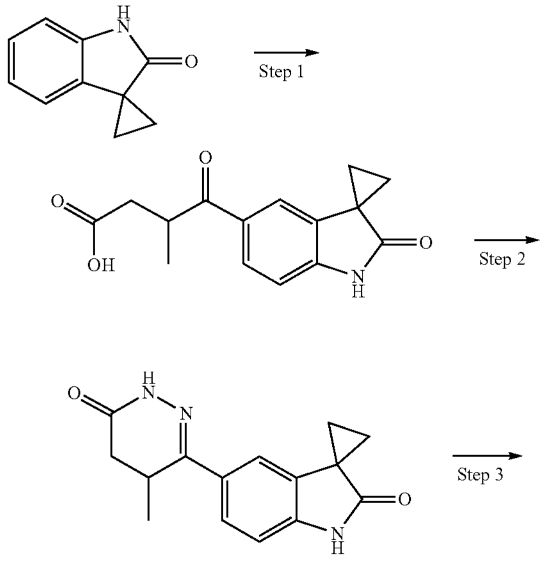

-continued

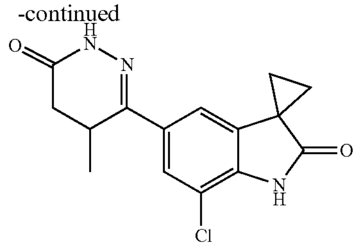

(8)

Step 1. A slurry of anhydrous $AlCl_3$ (20.97 g, 157.23 mmol) and DMF (0.004 mL, 47.17 mmol) was heated at 70° C. for 15 minutes and then cooled to 40° C. Spiro[cyclopropane-1,3'-indolin]-2'-one (2.5 g, 15.72 mmol) and 3-methyldihydrofuran-2,5-dione (2.15 g, 18.89 mmol) were slowly added. Resulting mixture was heated at 70° C. for 2 hours then poured into ice cooled water and extracted with ethyl acetate. Combined organic layer was washed with brine, dried over anhydrous sodium sulphate, filtered and concentrated under reduced pressure. Crude product thus obtained was triturated with diethyl ether-pentane to afford 3-methyl-4-oxo-4-{2'-oxo-1',2'-dihydrospiro[cyclo-propane-1,3'-indole]-5'-yl}butanoic acid (3.0 g, crude, mixture of products) as a brown gum. It was carried to the next step without further purification. MS (ESI): m/z 274.2 [M+1]+.

Step 2. To a stirred solution of 3-methyl-4-oxo-4-{2'-oxo-1',2'-dihydrospiro[cyclo-propane-1,3'-indole]-5'-yl}butanoic acid (3.0 g, 10.99 mmol) in ethanol (30.0 mL) was added hydrazine mono-hydrate (1.41 mL, 43.96 mmol). Resulting mixture was heated at 80° C. for 16 hours. Crude LCMS showed formation of two peaks with product mass (undesired:desired=4:1). Reaction mixture was evaporated under reduced pressure, residue was taken up in EtOH and stirred under cooling. Solid thus formed was filtered and discarded [contains major undesired isomer]. Filtrate was concentrated under reduced pressure and crude mass was purified by combiflash column chromatography (60-70% EtOAc in hexane) to afford 5'-(4-methyl-6-oxo-1,4,5,6-tetrahydropyridazin-3-yl)-1',2'-dihydrospiro[cyclopropane-1,3'-indole]-2'-one (270 mg, 7% in two steps) as off-white solid. MS (ESI): m/z 270.2 [M+1]+.

Step 3. To a stirred solution of 5'-(4-methyl-6-oxo-1,4,5,6-tetrahydropyridazin-3-yl)-1',2'-dihydrospiro[cyclopropane-1,3'-indole]-2'-one (270.0 mg, 1.00 mmol) in DMF (5.0 mL) was added NCS (200.99 mg, 1.51 mmol) at room temperature. Resulting reaction mixture was heated at 70° C. for 3 hours. After completion, reaction mixture was diluted with ice water and extracted with ethyl acetate. Combined organic layer was washed with brine, dried over anhydrous sodium sulphate, filtered and concentrated under reduced pressure. Crude product was purified by combiflash column chromatography (50-60% EtOAc in hexane) to afford the Example #8 compound. 1H NMR (400 MHz, DMSO-d6): δ 11.16 (s, 1H), 10.90 (s, 1H), 7.61 (s, 1H), 7.35 (s, 1H), 3.41-3.38 (m, 1H), 2.68-2.62 (m, 1H), 2.22 (d, J=16.8 Hz, 1H), 1.71-170 (m, 2H), 1.55-154 (m, 2H), 1.03 (d, J=7.2 Hz, 3H).

Preparation of Example #19 (6-(2-(1-(4-methoxy-phenyl)cyclopropyl)-1H-benzo[d]imidazol-6-yl)-5-methyl-4,5-dihydropyridazin-3(2H)-one)

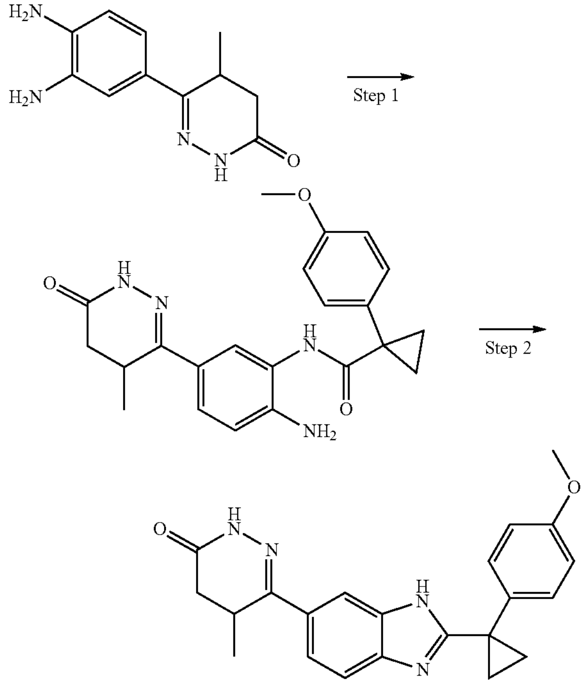

(19)

Step 1. To a stirred solution of 1-(4-methoxyphenyl) cyclopropane-1-carboxylic acid (200 mg, 1.04 mmol) in DMF (5 mL) at 0° C., was added 4-methyl morpholine (0.23 mL, 2.08 mmol) followed by HATU (395.64 mg, 1.041 mmol) and the resulting mixture was stirred at 0° C. for 10 minutes. 6-(3,4-diaminophenyl)-5-methyl-2,3,4,5-tetrahydropyridazin-3-one (227 mg, 1.04 mmol) was added and the resulting mixture was stirred at room temperature for 16 hours. After completion, the reaction mixture was diluted with water and extracted with 10% MeOH in DCM. Combined organic layer was washed with brine, dried over anhydrous sodium sulphate, filtered and concentrated under reduced pressure to get N-[2-amino-5-(4-methyl-6-oxo-1,4,5,6-tetrahydropyridazin-3-yl)phenyl]-1-(4-methoxyphenyl) cyclopropane-1-carboxamide (200 mg, crude) as yellow semi-solid [mixture of two regio-isomers]. It was used in the next step without further purification. MS (ESI): m/z 392.9 and 393.3 [M+1]+.

Step 2. A stirred solution of N-[2-amino-4-(4-methyl-6-oxo-1,4,5,6-tetrahydropyridazin-3-yl)phenyl]-1-(4-methoxyphenyl)cyclopropane-1-carboxamide (200 mg, 0.53 mmol) in acetic acid (5 mL) was heated at 100° C. for 16 hours. The reaction mixture was cooled to room temperature and volatiles were removed under reduce pressure. Crude product thus obtained was purified by reverse phase prep-HPLC to afford the Example #19 compound (110 mg, 58%) as an off white solid. $^{1}H$ NMR (400 MHz, DMSO-d6): δ 11.79 & 11.74 (s, 1H), 10.85 & 10.83 (s, 1H), 7.86 & 7.69 (s, 1H), 7.66 & 7.56 (d, J=8.2 Hz, 1H), 7.49 & 7.33 (d, J=8.2 Hz, 1H), 7.35-7.31 (m, 2H), 6.94 (m, 2H), 3.76 (s, 3H), 3.46 & 3.37 (m, 1H), 2.72 & 2.68 (m, 1H), 2.25 & 2.20 (m, 1H), 1.60-1.57 (m, 2H), 1.33-1.30 (m, 2H), 1.08 (d, J=6.8 Hz, 3H). LCMS: Retention time=2.20 minutes; HPLC purity=99.72%. Note: 1H NMR indicated the product to be a mixture of isomers.

Preparation of Example #21 (5-methyl-6-(1-methyl-2-(phenylamino)-1H-benzo[d]imidazol-6-yl)-4,5-dihydropyridazin-3(2H)-one)

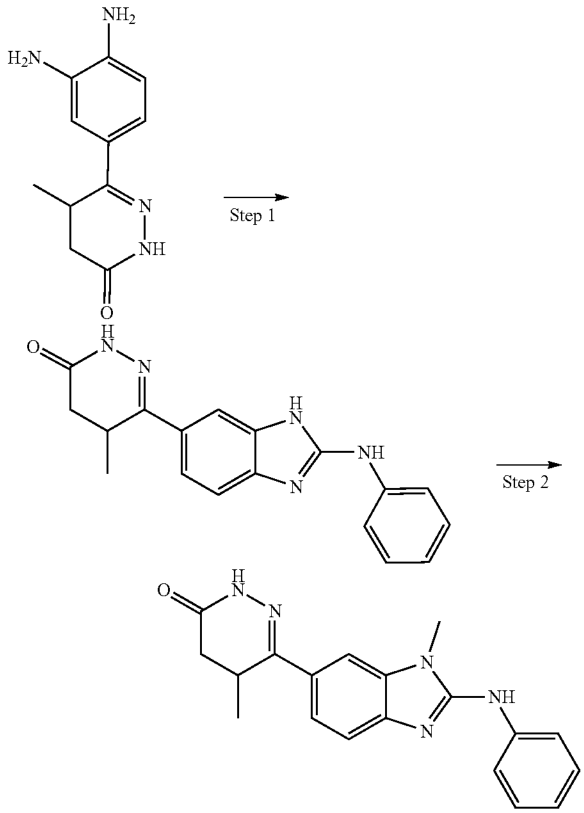

(21)

Step 1. Isothiocyanatobenzene (1.2 mL, 10.00 mmol) in N,N-dimethylformamide (15 mL) at room temperature, was added to a solution of 3-(3,4-diaminophenyl)-4-methyl-4,5-dihydro-1H-pyridazin-6-one (2.183 g, 10.00 mmol) in N,N-dimethylformamide (15 mL) and the contents were stirred at room temperature. After 2 hours, N,N'diisopropyl-methanediimine (1.86 mL, 12.00 mmol) was then added to the reaction mixture and the contents were stirred at 70° C. overnight. The reaction mixture was then cooled to room temperature and purified directly by reverse phase chromatography to give 3-(2-anilino-3H-benzimidazol-5-yl)-4-methyl-4,5-dihydro-1H-pyridazin-6-one (m/z [M+H]=320).

Step 2. A 60% sodium hydride dispersion in mineral oil (138 mg, 3.44 mmol) was added to a tetrahydrofuran (20 mL) solution of 3-(2-anilino-3H-benzimidazol-5-yl)-4-methyl-4,5-dihydro-1H-pyridazin-6-one (1.00 g, 3.13 mmol) at 0° C. and stirred for 1 hour. Methyl iodide (0.214 mL, 3.44 mmol) was then added and the mixture stirred overnight. The resulting mixture was diluted with ethyl acetate and washed with water and brine. The organic layer was concentrated under reduced pressure and the residue purified by reverse phase preparative HPLC to afford the Example #21 compound. dH (d6-DMSO) 10.83 (s, 1H), 9.00 (s, 1H), 7.87 (d, 2H), 7.71 (s, 1H), 7.55 (d, 1H), 7.25-7.40 (m, 3H), 6.97 (t, 1H), 3.75 (s, 3H), 3.45-3.60 (m, 1H), 2.70 (dd, 1H), 2.26 (d, 1H), 1.12 (d, 3H).

Preparation of Example #24 (7-chloro-3,3-dimethyl-5-(4-methyl-6-oxo-1,4,5,6-tetrahydropyridazin-3-yl)indolin-2-one)

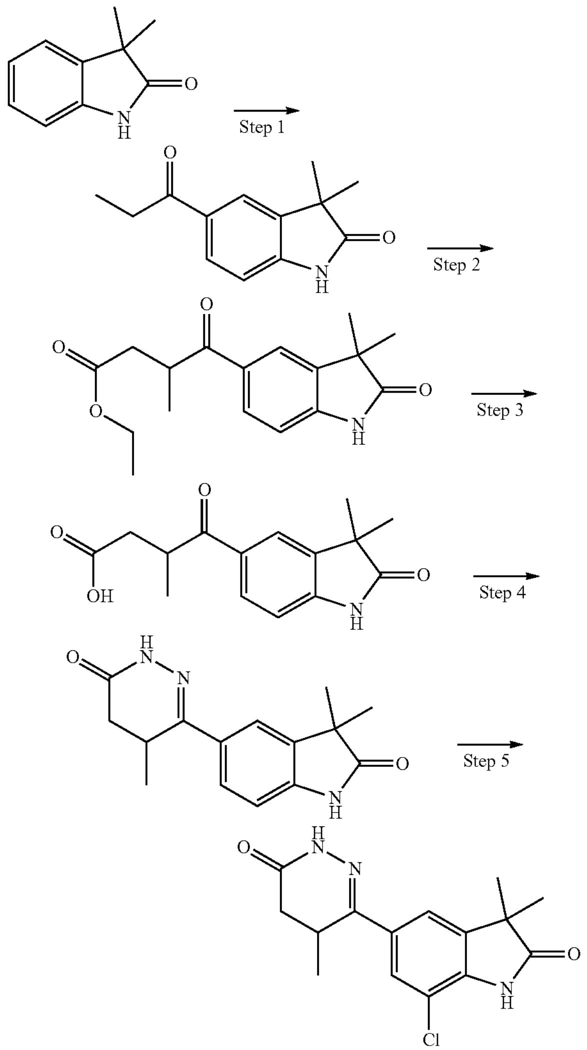

(24)

Step 1. To a stirred solution of 3,3-dimethyl-2,3-dihydro-1H-indol-2-one (5.0 g, 31.02 mmol) in 1,2-dichloroethane (150 mL) at 0° C., was added anhydrous aluminum chloride (10.4 g, 77.54 mmol) and stirred at 10° C. for 30 minutes. Propionyl chloride (5.8 g, 62.04 mmol) was added drop wise to the reaction mixture and stirred at 80° C. for 16 hours. After completion, reaction mixture was diluted with ice cooled water and extracted with DCM. Combined organic layer was washed with brine, dried over anhydrous sodium sulphate, filtered and concentrated under reduced pressure. Crude product was purified by combiflash chromatography (30-40% EtOAc in hexane) to afford 3,3-dimethyl-5-propanoyl-2,3-dihydro-1H-indol-2-one (3 g, 44%) as an off white solid. MS (ESI): m/z 218.0 [M+1]+.

Step 2. A solution of 3,3-dimethyl-5-propanoyl-2,3-dihydro-1H-indol-2-one (2 g, 9.20 mmol) in THE (30 mL) was added to a stirred solution of LiHMDS (11.1 mL, 11.1 mmol, 1 M in THF) in THE (30 mL) at −78° C. and resulting mixture was stirred at −78° C. for 1 hour. A solution of ethyl 2-bromoacetate (1.85 g, 11.05 mmol) in THF (30 mL) was added drop wise over 20 minutes and stirred additional 1 hour at −78° C. After completion, reaction mixture was quenched with 1 N HCl and extracted with ethyl acetate. Combined organic layer was washed with brine, dried over anhydrous sodium sulphate, filtered and concentrated under reduced pressure. Crude product was purified by combiflash chromatography (40-50% EtOAc in hexane) to afford ethyl 4-(3,3-dimethyl-2-oxo-2,3-dihydro-1H-indol-5-yl)-3-methyl-4-oxobutanoate (900 mg, 32%) as off white solid. MS (ESI): m/z 304.0 $[M+1]^+$.

Step 3. To a stirred solution of ethyl 4-(3,3-dimethyl-2-oxo-2,3-dihydro-1H-indol-5-yl)-3-methyl-4-oxobutanoate (700 mg, 2.31 mmol) in EtOH (20 mL) and MeOH (5 mL) at 0° C., was added $LiOH{\cdot}H_2O$ (11.5 mL, 11.54 mmol, 1 M in $H_2O$) drop wise and stirred at room temperature for 16 hours. After completion, reaction mixture was evaporated under reduced pressure, residue was diluted with water and extracted with 50% ethyl acetate in hexane. Organic portion was discarded. Aqueous part was acidified with 2N HCl to pH ~4 and extracted with 10% MeOH in ethyl acetate. Combined organic layer was washed with brine, dried over anhydrous sodium sulphate, filtered and concentrated under reduced pressure to afford 4-(3,3-dimethyl-2-oxo-2,3-dihydro-1H-indol-5-yl)-3-methyl-4-oxobutanoic acid (470 mg, 74%) as a white solid. MS (ESI): m/z 274.4 $[M-1]^+$.

Step 4. To a stirred solution of 4-(3,3-dimethyl-2-oxo-2,3-dihydro-1H-indol-5-yl)-3-methyl-4-oxobutanoic acid (470 mg, 1.71 mmol) in ethanol (15 mL) was added hydrazine monohydrate (89.7 mg, 1.79 mmol) and stirred at 80° C. for 16 hours. After completion, volatiles were removed under reduced pressure and crude product was purified by combiflash column chromatography (60-70% ethyl acetate in hexane) to afford 3,3-dimethyl-5-(4-methyl-6-oxo-1,4,5,6-tetrahydropyridazin-3-yl)-2,3-dihydro-1H-indol-2-one (200 mg, 43%) as off white solid. MS (ESI): m/z 271.9 $[M+1]^+$.

Step 5. To a stirred solution of 3,3-dimethyl-5-(4-methyl-6-oxo-1,4,5,6-tetrahydropyridazin-3-yl)-2,3-dihydro-1H-indol-2-one (50 mg, 0.18 mmol) in DMF (1 mL) was added N-chlorosuccinimide (27 mg, 0.2 mmol) and stirred at room temperature for 1 hour. After completion, reaction mixture was poured into ice-water. Solid thus formed was filtered, washed with diethyl ether and dried under vacuum to afford the Example #24 compound (20 mg, 35%) as a white solid. 1H NMR (400 MHz, DMSO-d6): δ 10.95 (s, 1H), 10.92 (s, 1H), 7.71 (s, 1H), 7.62 (s, 1H), 3.42-3.37 (m, 1H), 2.71-2.65 (m, 1H), 2.22 (d, J=16.8 Hz, 1H), 1.30 (s, 6H), 1.06 (d, J=7.2 Hz, 3H). LCMS: Retention time=1.56 minutes; HPLC purity=98.00%. Enantiomers of Example #24 are Example #33 and Example #51. Example #33 is the (R)-isomer and was resolved by HPLC (column Chiralpak IG 250×4.6 mm, 5μ; mobile phase (hexane/DCM/EtOH/isopropylamine (50/25/25/0.1) at a flow rate of 1.0 mL/minute. HPLC retention time for Example #33 and #24 was 5.88 and 6.63 minutes, respectively.

Preparation of Example #23, 7-bromo-3,3-dimethyl-5-(4-methyl-6-oxo-1,4,5,6-tetrahydropyridazin-3-yl)indolin-2-one, was conducted in a similar fashion to Example #24 but for 7-bromo-3,3-dimethylindolin-2-one instead of 7-chloro-3,3-dimethylindolin-2-one to afford the Example #23 compound. 1H NMR (400 MHz, DMSO-d6): δ 10.92 (s, 1H), 10.83 (s, 1H), 7.74 (s, 2H), 3.42-3.38 (m, 1H), 2.70-2.65 (m, 1H), 2.22 (d, J=16.8 Hz, 1H), 1.29 (s, 6H), 1.05 (d, J=7.2 Hz, 3H).

Preparation of Example #26 (7-fluoro-3,3-dimethyl-5-(4-methyl-6-oxo-1,4,5,6-tetrahydropyridazin-3-yl) indolin-2-one)

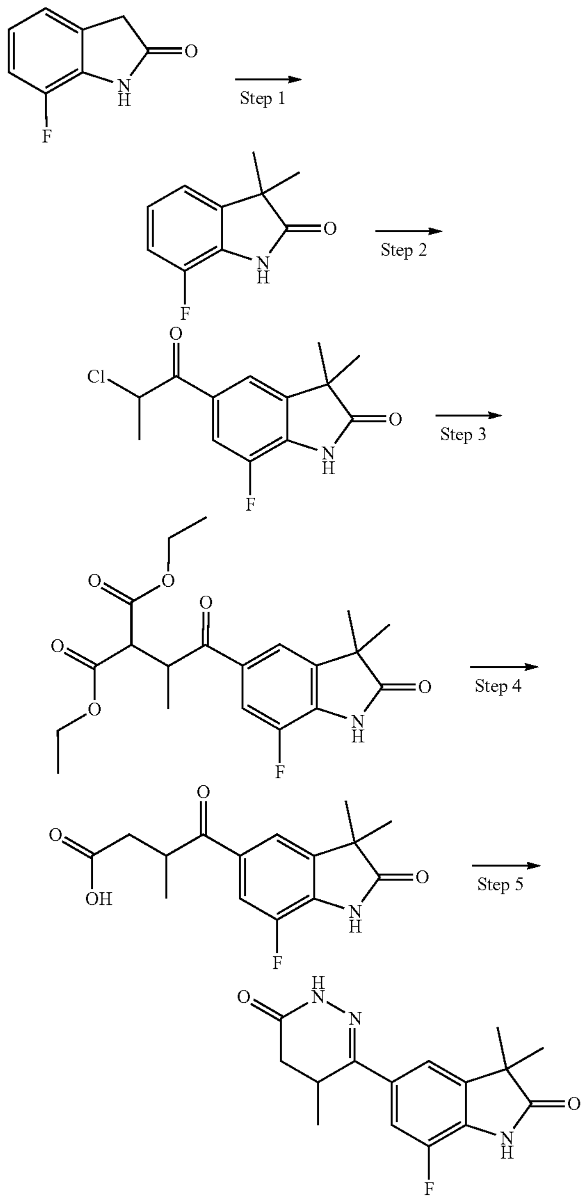

(26)

Step 1. To a stirred solution of 7-fluoroindolin-2-one (5 g, 33.11 mmol) in dry THF (50 mL) was added lithium chloride (4.2 g, 99.34 mmol) and resulting mixture was cooled to −78° C. Lithium diisopropylamide (33.1 mL, 66.2 mmol, 2.0 M in THF/heptane/ethylbenzene) was added and stirred at −78° C. for 15 minutes. Methyl iodide (1.8 mL, 66.2 mmol) was added and reaction mixture was stirred at room temperature for 5 hours. After completion, reaction mixture was quenched with aqueous ammonium chloride solution and extracted with ethyl acetate. Combined organic layer was washed with brine, dried over anhydrous sodium sulphate, filtered and concentrated under reduce pressure. Crude product was purified by column chromatography (10-20% EtOAc in hexane) to afford 7-fluoro-3,3-dimethyl-2,3-dihydro-1H-indol-2-one (2.7 g, 46%) as white solid. MS (ESI): m/z 180.1 [M+1]+.

Step 2. DMF (3.78 mL, 49.54 mmol) was added drop wise to anhydrous $AlCl_3$ (19.98 g, 150.12 mmol) and resultant mixture was stirred at 70° C. for 15 minutes and then cooled to 40° C. 7-fluoro-3,3-dimethyl-2,3-dihydro-1H-indol-2-one (2.7 g, 15.08 mmol) and 2-chloropropanoyl chloride (1.86 ml, 18.75 mmol, 1.25 eq.) were slowly added to the $AlCl_3$ melt and heated to 70° C. for 4 hours. After completion, reaction mixture was allowed to attain ambient temperature, poured into crushed ice slowly and extracted with ethyl acetate. Combined organic layer was washed with brine, dried over anhydrous sodium sulphate, filtered and concentrated under reduced pressure. Crude product was purified by column chromatography (10-20% EtOAc in hexane) to afford 5-(2-chloropropanoyl)-7-fluoro-3,3-dimethylindolin-2-one (1.4 g, 35%) as yellow solid. MS (ESI): m/z 270.2 [M+1]+.

Step 3. To a stirred solution of potassium tert-butoxide (850 mg, 7.55 mmol) in DMSO (20 mL) was added diethylmalonate (1.2 gm, 7.55 mmol) in DMSO (12 mL), drop wise over 10 minutes. The solution was stirred for 20 minutes and 5-(2-chloropropanoyl)-7-fluoro-3,3-dimethyl-indolin-2-one (1.4 gm, 5.8 mmol) in DMSO (5 mL) was added. Resulting mixture was stirred at room temperature for 3 hours. After completion, reaction mixture was quenched with acetic acid (0.6 mL, 10 mmol) and extracted with ethyl acetate. Combined organic layer was washed with brine, dried over anhydrous sodium sulphate, filtered and concentrated under reduced pressure. Crude product was purified by column chromatography (30-40% ethyl acetate in hexane) to afford diethyl 2-(1-(7-fluoro-3,3-dimethyl-2-oxoindolin-5-yl)-1-oxopropan-2-yl)malonate (800 mg, 27%) as off white solid. MS (ESI): m/z 394.1 [M+1]+.

Step 4. A solution of diethyl 2-(1-(7-fluoro-3,3-dimethyl-2-oxoindolin-5-yl)-1-oxopropan-2-yl)malonate (800 mg, 2.03 mmol) in 6N HCl (50 ml) and dioxane (15 mL) was heated to 90° C. for 16 hours. Reaction mixture was cooled to room temperature, diluted with water and extracted ethyl acetate. Combined organic layer was washed with brine, dried over anhydrous sodium sulphate, filtered and concentrated under reduced pressure to afford 4-(7-fluoro-3,3-dimethyl-2-oxoindolin-5-yl)-3-methyl-4-oxobutanoic acid (600 mg, crude) as colorless gum. MS (ESI): m/z 294.3 [M+1]+.

Step 5. To a stirred solution of 4-(7-fluoro-3,3-dimethyl-2-oxoindolin-5-yl)-3-methyl-4-oxobutanoic acid (600 mg, crude) in ethanol (20 mL) was added hydrazine monohydrate (3 mL) and heated to 90° C. for 16 hours. After completion, reaction mixture was quenched with water and extracted with 10% MeOH in DCM. Combined organic layer was washed with brine, dried over anhydrous sodium sulphate, filtered and concentrated under reduced pressure. Crude product was purified by column chromatography (1-5% MeOH in DCM) to afford the Example #26 compound (340 mg, 54% in two steps) as an off white solid. 1H NMR (400 MHz, DMSO-d6): δ 11.02 (s, 1H), 10.92 (s, 1H), 7.61 (s, 1H), 7.50-7.48 (m, 1H), 3.40-3.38 (m, 1H), 2.689-2.66 (m, 1H), 2.24-2.20 (m, 1H), 1.29 (s, 6H), 1.05 (bs, 3H). Retention time=6.11 minutes; HPLC purity=96.27%

Preparation of Example #27 (7-fluoro-3,3-dimethyl-5-(6-oxo-1,6-dihydropyridazin-3-yl)indolin-2-one)

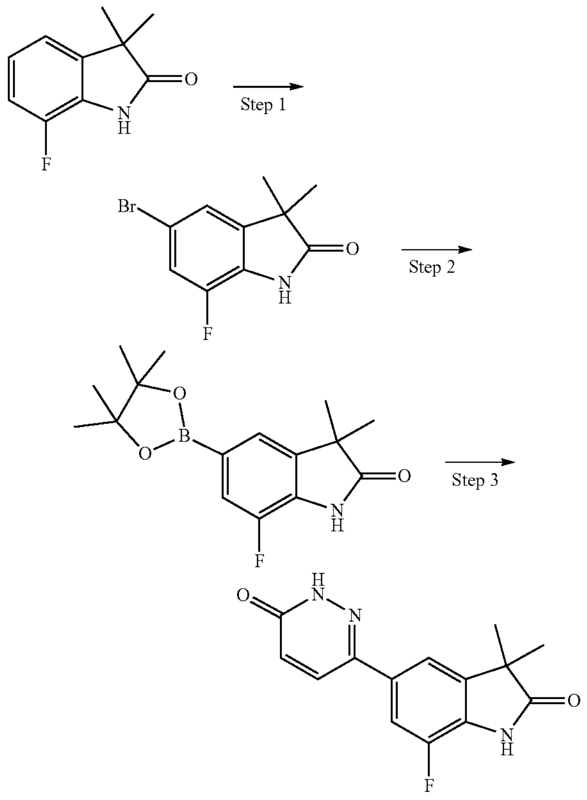

(27)

Step 1. To a stirred solution of 7-fluoro-3,3-dimethyl-2,3-dihydro-1H-indol-2-one (2.7 gm, 15.08 mmol) in trifluoroacetic acid (30 mL) was added N-bromosuccinimide (4 g, 22.63 mmol) portion wise and reaction mixture was stirred at room temperature for 16 hours. After completion, trifluoroacetic acid was evaporated under reduced pressure. Residue was diluted with ethyl acetate, water and layers were separated. Organic layer was dried over anhydrous sodium sulphate, filtered, concentrated under reduced pressure. Crude product thus obtained was purified by combi flash column chromatography (30-40% ethyl acetate in hexane) to afford 5-bromo-7-fluoro-3,3-dimethylindolin-2-one (2 g, 52%) as off-white solid. MS (ESI): m/z 257.6 [M+1]+.

Step 2. To a stirred solution of 5-bromo-7-fluoro-3,3-dimethylindolin-2-one (2 g, 7.72 mmol) in dioxane (5 mL) was added bis(pinacolato)diboron (2.37 g, 9.33 mmol) followed by KOAc (1.51 g, 15.44 mmol) and resulting mixture was purged with argon for 10 minutes. Pd(dppf)$Cl_2$·DCM (630 mg, 0.772 mmol) was added and reaction mixture was heated at 95° C. for 16 hours. After completion, reaction mixture was diluted with water and extracted with ethyl acetate. Combined organic layer was washed with brine, dried over anhydrous sodium sulphate, filtered and concentrated under reduced pressure. Crude product was purified by combi flash column chromatography (30-40% EtOAc in hexane) to afford 7-fluoro-3,3-dimethyl-5-(4,4,5,5-tetramethyl-1,3,2-dioxaborolan-2-yl)indolin-2-one (1.5 g, 63%) as off-white solid. MS (ESI): m/z 305.9 [M+1]+.

Step 3. 7-fluoro-3,3-dimethyl-5-(6-oxo-1,6-dihydropyridazin-3-yl)indolin-2-one

To a stirred solution 7-fluoro-3,3-dimethyl-5-(4,4,5,5-tetramethyl-1,3,2-dioxaborolan-2-yl)indolin-2-one (1.5 g, 4.92 mmol) in a mixture of 1,4-dioxane (15 mL) and water (5 mL) was added 6-bromo-2,3-dihydropyridazin-3-one (1.29 g, 7.38 mmol) followed by $K_3PO_4$ (2.61 g, 12.3 mmol) and resulting mixture was purged with argon for 10 minutes. Pd-118 (321 mg, 0.49 mmol) was added and reaction mixture was heated in sealed tube at 100° C. for 16 hours. After completion, reaction mixture was diluted with water and extracted with 10% MeOH in DCM. Combined organic layer was washed with brine, dried over anhydrous sodium sulphate, filtered and concentrated under reduced pressure. Crude product thus obtained was purified combi flash column chromatography (1-5% MeOH in DCM) to afford the Example #27 compound (220 mg, 17%) as an off-white solid. 1H NMR (400 MHz, DMSO-d6): δ 13.16 (s, 1H), 11.04 (s, 1H), 8.06 (d, J=9.9 Hz, 1H), 7.71 (s, 1H), 7.61 (d, J=11.7 Hz, 1H), 6.99 (d, J=9.9 Hz, 1H), 1.32 (s, 6H). LCMS: Retention time=1.80 minutes; HPLC purity=98.01%

Preparation of Example #28 (7'-fluoro-5'-(4-methyl-6-oxo-1,4,5,6-tetrahydropyridazin-3-yl)spiro[cyclopropane-1,3'-indolin]-2'-one)

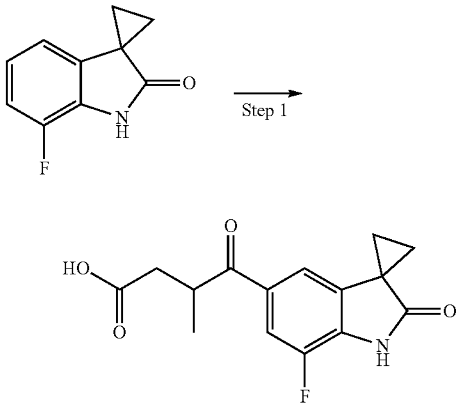

(1:4)

+

-continued

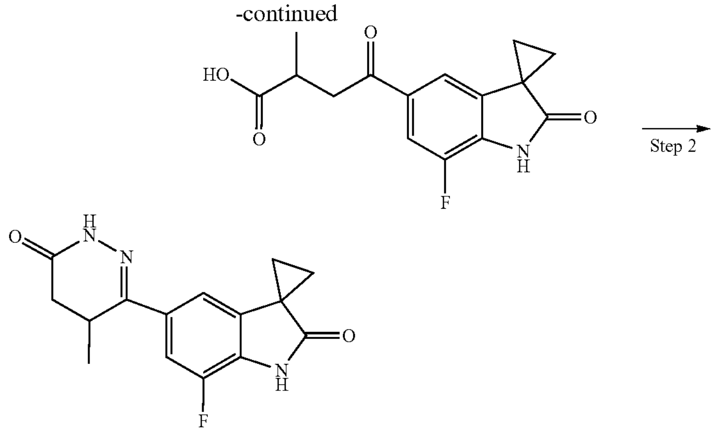

(28)

Step 1. A slurry of $AlCl_3$ (7.5 g, 56.44 mmol) and DMF (1.3 mL, 16.93 mmol) was heated at 70° C. for 15 minutes then cooled to 40° C. 7'-fluorospiro[cyclopropane-1,3'-indolin]-2'-one (1.0 g, 5.64 mmol) and 3-methyldihydrofuran-2,5-dione (590 mg, 7.34 mmol) were slowly added. Resulting mixture was heated at 70° C. for 8 hours, poured into crushed ice and extracted with ethyl acetate. Combined organic layer was washed with brine, dried over anhydrous sodium sulphate, filtered and concentrated under reduced pressure. Crude product thus obtained was triturated with diethyl ether-pentane to afford a mixture of 4-(7'-fluoro-2'-oxospiro[cyclopropane-1,3'-indolin]-5'-yl)-3-methyl-4-oxobutanoic acid and 4-(7'-fluoro-2'-oxospiro[cyclopropane-1,3'-indolin]-5'-yl)-2-methyl-4-oxobutanoic acid (800 mg, crude, desired:undesired=1:4) as brown gum.

It was carried to the next step without further purification. MS (ESI): m/z 291.7 [M+1]+.

Step 2. To a stirred solution of 4-(7'-fluoro-2'-oxospiro [cyclopropane-1,3'-indolin]-5'-yl)-3-methyl-4-oxobutanoic acid (800.0 mg, 2.75 mmol) in ethanol (20.0 mL) was added hydrazine mono hydrate (0.66 mL, 13.74 mmol). Resulting mixture was heated at 80° C. for 16 hours. Crude LCMS showed formation of two peaks with product mass (undesired:desired=4:1). Reaction mixture was evaporated under reduced pressure, residue was taken up in EtOH and stirred under cooling. Solid thus formed was filtered and discarded [contained major undesired isomer]. Filtrate was concentrated under reduced pressure and purified by reverse phase prep HPLC to afford the Example #28 compound (60 mg, 4% in two steps) as an off-white solid. 1H NMR (400 MHz, DMSO-d6): δ 10.90 (bs, 2H), 7.48 (d, J=12 Hz, 1H), 7.26 (s, 1H), 3.38 (t, J=7.0 Hz, 1H), 2.68-2.62 (m, 1H), 2.24-2.20 (m, 1H), 1.71-1.69 (m, 2H), 1.54-1.53 (m, 2H), 1.04 (d, J=7.2 Hz, 3H). LCMS: Retention time=2.11 minutes; HPLC purity=99.66%

Preparation of Example #30 (6-(2-amino-4-chlorobenzo[d]thiazol-6-yl)-5-methyl-4,5-dihydropyridazin-3(2H)-one)

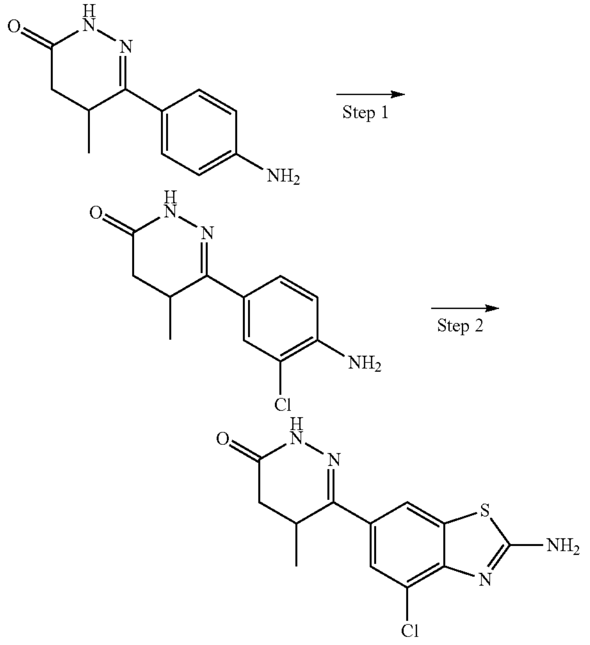

(30)

Step 1: 6-(4-amino-3-chlorophenyl)-5-methyl-4,5-dihydropyridazin-3(2H)-one

To a solution of 3-(4-aminophenyl)-4-methyl-4,5-dihydro-1H-pyridazin-6-one (2.0 g, 9.8 mmol) in DMF (15 mL) was added NCS (1.31 g, 9.8 mmol). The reaction was warmed to 45° C. and stirred overnight. Next, the reaction mixture was cooled to room temperature, diluted with water, and extracted with EtOAc:MeOH (90:10 2×100 mL). The combined organic phase was dried ($Na_2SO_4$) and concentrated under vacuum. The crude material was chromatographed (40 g Redi-Sep column) eluting from 100% hexanes to 60:40 EtOAc:hexanes to afford the intermediate as a solid (1.52 g, 65%). LC/MS M+H=238.

Step 2: To a solution of 6-(4-amino-3-chlorophenyl)-5-methyl-4,5-dihydropyridazin-3(2H)-one (2.0 g, 8.4 mmol) in AcOH (50 mL), cooled slightly in ice bath, was added potassium thiocyanate (3.3 g, 33.6 mmol). The contents were stirred at room temperature for 15 minutes. Next, bromine (0.45 mL, 8.4 mmol), dissolved in AcOH (2 mL), was added dropwise and the reaction was stirred at room temperature overnight. The reaction was neutralized with saturated $NaHCO_3$ and the resulting precipitate was filtered and air-dried to afford the intermediate as an orange solid (2.9 g, 97%). 500 mg of the crude product was purified using SFC chromatography to afford the Example #30 compound (253 mg) as a solid. LC/MS M+H=295; 1H NMR (400 MHz, DMSO-d6): δ 10.94 (s, 1H), 8.06 (s, 1H), 8.02 (br s, 2H), 7.71 (s, 1H), 3.40 (q, 1H), 2.70-2.66 (m, 1H), 2.23 (d, 1H), 1.07 (d, 3H).

Preparation of Example #31: 6-(2-amino-4-fluorobenzo[d]thiazol-6-yl)-5-methyl-4,5-dihydropyridazin-3(2H)-one

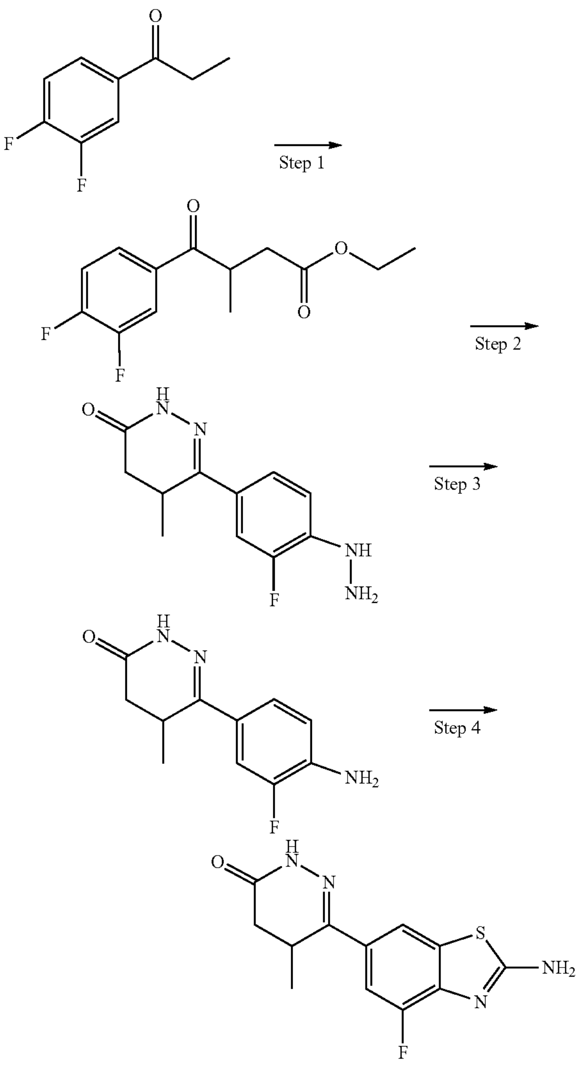

(31)

Step 1: ethyl 4-(3,4-difluorophenyl)-3-methyl-4-oxobutanoate

To a 1 M solution of KHMDS in THE (22.0 mL, 22.0 mmol) was added to THE (25 mL) in a round bottom flask and cooled to −78° C. Next, 1-(3,4-difluorophenyl)propan-1-one (3.75 g, 22.0 mmol) in 10 mL THE was added dropwise and the reaction mixture was stirred at −78° C. for 1 hour. Ethyl 2-bromoacetate (4.8 g, 28.6 mmol) in 10 mL THE was slowly added and the reaction mixture was allowed to warm to 0° C. while stirring for 1 hour. The reaction was quenched with 1 N HCl and extracted with EtOAc (2×75 mL). The combined organic phase was dried ($Na_2SO_4$) and concentrated under vacuum. The crude product was chromatographed (120 g Redi-Sep column) eluting from 100% hexanes to 10:90 EtOAc:hexanes to afford the intermediate as a clear oil (3.9 g, 69%). LC/MS M+H=257.

Step 2: 6-(3-fluoro-4-hydrazineylphenyl)-5-methyl-4,5-dihydropyridazin-3(2H)-one To a solution of ethyl 4-(3,4-difluorophenyl)-3-methyl-4-oxo-butanoate (1.0 g, 3.9 mmol) in 2-MeTHF (15 mL) was added a hydrazine hydrate (0.5 mL, 15.6 mmol). The reaction was heated to 110° C. for 6 hours under microwave irradiation. Next, the crude mixture was cooled in an ice-bath while stirring and the resulting precipitate was filtered, washed with cold EtOH, and air-dried to afford the intermediate as a colorless solid (0.7 g, 76%). LC/MS M+H=237.

Step 3: 6-(4-amino-3-fluorophenyl)-5-methyl-4,5-dihydropyridazin-3(2H)-one

To a solution of 6-(3-fluoro-4-hydrazineylphenyl)-5-methyl-4,5-dihydropyridazin-3(2H)-one (750 mg, 3.2 mmol) in MeOH (200 mL) and AcOH (1 mL) was added 10% Pd/C (200 mg). The reaction mixture was hydrogenated at room temperature on a Parr shaker at 20 psi for 2 hours and subsequently filtered through celite. The mother liquor was concentrated under vacuum to afford the intermediate as a semi-solid. (0.67 g, 95%). LC/MS M+H=222.

Step 4: To a solution of 6-(4-amino-3-fluorophenyl)-5-methyl-4,5-dihydropyridazin-3(2H)-one (1.1 g, 4.9 mmol) in AcOH (35 mL), cooled slightly in ice bath, was added potassium thiocyanate (1.9 g, 19.9 mmol). The contents were stirred at room temperature for 15 minutes. Next, bromine (0.25 mL, 4.9 mmol), dissolved in AcOH (1 mL), was added dropwise and the reaction was stirred at room temperature overnight. The reaction was neutralized with saturated $NaHCO_3$ and extracted with EtOAc:MeOH (100 mL, 90:10) to afford the crude product (1.2 g, 88%) as a gum after concentration. 100 mg of the crude product was purified using reverse-phase chromatography eluting from 95:5:0.1 water:MeCN:TFA to 80:20:0.1 MeCN:water:TFA over 20 minutes to afford the Example #31 compound (31 mg) as a solid. LC/MS M+H=279; 1 H NMR (400 MHz, DMSO-d6): δ 10.94 (s, 1H), 7.95 (s, 1H), 7.91 (br s, 2H), 7.50 (d, 1H), 3.39 (q, 1H), 2.71-2.67 (m, 1H), 2.23 (d, 1H), 1.08 (d, 3H).

Preparation of Example #32 (7-bromo-3,3-dimethyl-5-(6-oxo-1,6-dihydropyridazin-3-yl)indolin-2-one)

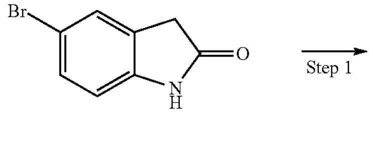

-continued

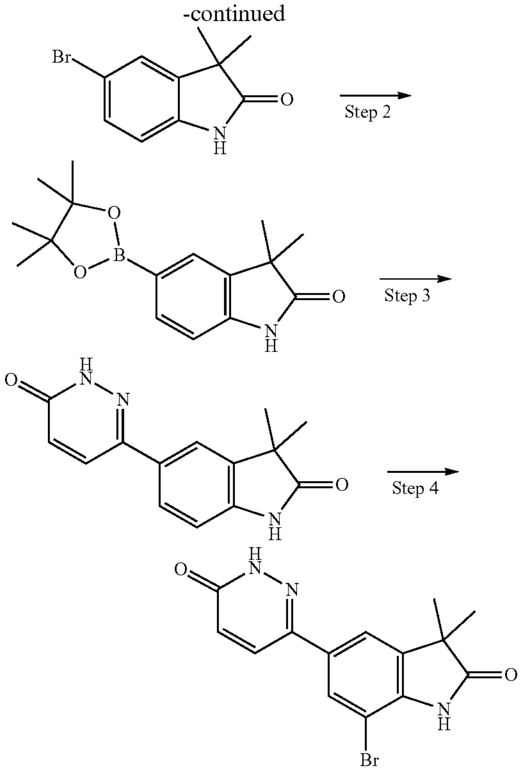

(32)

Step 1. To a stirred solution of 5-bromoindolin-2-one (5 g, 23.58 mmol) in dry THE (50 mL) was added lithium chloride (2.9 g, 70.75 mmol) and resulting mixture was cooled to −78° C. Lithium diisopropylamide (23.5 mL, 47.17 mmol, 2.0 M in THF/heptane/ethylbenzene) was added and stirred at −78° C. for 15 minutes. Methyl iodide (2.9 mL, 47.17 mmol) was added and reaction mixture was stirred at room temperature for 5 hours. After completion, reaction mixture was quenched with aqueous ammonium chloride solution and extracted with ethyl acetate. Combined organic layer was washed with brine, dried over anhydrous sodium sulphate, filtered and concentrated under reduce pressure. Crude product was purified by column chromatography (10-20% EtOAc in hexane) to afford 5-bromo-3,3-dimethylindolin-2-one (2.3 g, 41%) as white solid. MS (ESI): m/z 240 [M+1]+.

Step 2. To a stirred solution of 5-bromo-3,3-dimethylindolin-2-one (2.3 g, 9.58 mmol) in dioxane (15 mL) was added bis(pinacolato)diboron (2.9 g, 11.5 mmol) followed by KOAc (1.8 g, 19.16 mmol) and resulting mixture was purged with argon for 10 minutes. Pd(dppf)$Cl_2$·DCM (0.783 g, 0.958 mmol) was added and reaction mixture was heated at 95° C. for 16 hours. After completion, reaction mixture was diluted with water and extracted with ethyl acetate. Combined organic layer was washed with brine, dried over anhydrous sodium sulphate, filtered and concentrated under reduced pressure. Crude was purified by combi flash chromatography (30-40% EtOAc in hexane) to afford 3,3-dimethyl-5-(4,4,5,5-tetramethyl-1,3,2-dioxaborolan-2-yl)-2,3-dihydro-1H-indol-2-one (1.45 g, 53%) as off-white solid. MS (ESI): m/z 288 [M+1]+.

Step 3. To a stirred solution 3,3-dimethyl-5-(4,4,5,5-tetramethyl-1,3,2-dioxaborolan-2-yl)-2,3-dihydro-1H-indol-2-one (640 mg, 2.23 mmol) in a mixture of 1,4-dioxane (10 mL) and water (5 mL) was added 6-bromo-2,3-dihydropyridazin-3-one (585 mg, 3.34 mmol) followed by $K_3PO_4$ (1.2 g, 5.57 mmol) and resulting mixture was purged with argon for 10 minutes. Xphos (213 mg, 0.446 mmol) and Xphos Pd G3 (175 mg, 0.223 mmol) were added and reaction mixture was heated in sealed tube at 100° C. for 16 hours. After completion, reaction mixture was diluted with water and extracted with 10% MeOH in DCM. Combined organic layer was washed with brine, dried over anhydrous sodium sulphate, filtered and concentrated under reduced pressure. Crude product thus obtained was purified by combi flash column chromatography (1-5% MeOH in DCM) to afford 3,3-dimethyl-5-(6-oxo-1,6-dihydropyridazin-3-yl)-2,3-dihydro-1H-indol-2-one (170 mg, 30%) as off-white solid. MS (ESI): m/z 256 [M+1]+.

Step 4. To a stirred solution of 3,3-dimethyl-5-(6-oxo-1,6-dihydropyridazin-3-yl)-2,3-dihydro-1H-indol-2-one (170 mg, 0.667 mmol) in DMF (5 mL) was added N-bromosuccinimide (142 mg, 0.8 mmol) portion wise and resulting mixture was stirred at room temperature for 16 hours. After completion, reaction mixture was diluted with water and extracted with 10% MeOH in DCM. Combined organic layer was washed with brine, dried over anhydrous sodium sulphate, filtered and concentrated under reduced pressure. Crude product (Example #32) thus obtained was purified by combi flash chromatography (1-5% MeOH in DCM) to afford the Example #32 compound (65 mg, 29%) as an off-white solid. 1H NMR (400 MHz, DMSO-d6): δ 13.15 (br s, 1H), 10.85 (br s, 1H), 8.07 (d, J=10 Hz, 1H), 7.86 (s, 1H), 7.83 (s, 1H), 6.98 (d, J=11.2 Hz, 1H), 3.31 (s, 6H). LCMS: Retention time=2.17 minutes; HPLC purity [at 254 nm]=98.61%

Preparation of Example #34 (6-(4-fluoro-2-(methylamino)benzo[d]thiazol-6-yl)-5-methyl-4,5-dihydropyridazin-3(2H)-one)

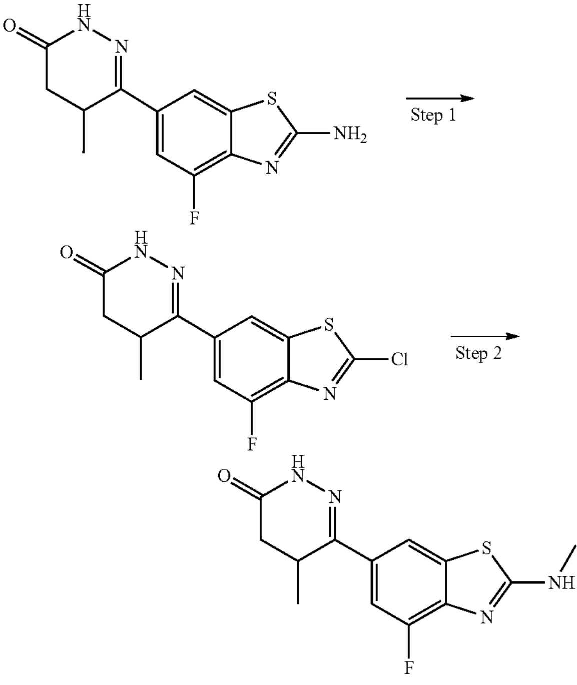

(34)

Step 1. 3-(2-amino-4-fluoro-1,3-benzothiazol-6-yl)-4-methyl-4,5-dihydro-1H-pyridazin-6-one (1.0 g, 3.6 mmol) was charged to a mixture of copper powder (195 mg, 2.9 mmol) in concentrated HCl (10.0 mL) and water (3.0 mL) at 0° C. Next, an excess of $NaNO_2$ (750 mg, 10.8 mmol) dissolved in 3 mL water was slowly added. The reaction was allowed to warm to room temperature and stirred for 3 hours. Next, the reaction mixture was diluted with water (25 mL), filtered, and air-dried to afford 6-(2-chloro-4-fluorobenzo[d]thiazol-6-yl)-5-methyl-4,5-dihydropyridazin-3(2H)-one as a solid (598 mg, 56%). LC/MS M+H=298.

Step 2. To a solution of 3-(2-chloro-1,3-benzothiazol-6-yl)-4-methyl-4,5-dihydro-1H-pyridazin-6-one (55 mg, 0.2 mmol) in EtOH (5 mL) was added N-methylamine (0.2 g, 2.0 mmol; 33 weight % in EtOH). The reaction mixture was heated at 80° C. for 2 hours, then cooled to room temperature. The crude product was purified using reverse-phase chromatography eluting from 95:5:0.1 water:MeCN:TFA to 75:25:0.1 MeCN:water:TFA over 20 minutes to afford the Example #34 compound (32 mg, 54%) as a solid. LC/MS M+H=293; 1H NMR (400 MHz, DMSO-d6): δ 10.94 (s, 1H), 8.34 (br s, 1H), 7.96 (s, 1H), 7.51 (d, 1H), 3.39 (q, 1H), 2.98 (s, 3H), 2.71-2.67 (m, 1H), 2.23 (d, 1H), 1.08 (d, 3H).

Preparation of Example #37, 6-(4-fluoro-2-(3-hydroxyazetidin-1-yl)benzo[d]thiazol-6-yl)-5-methyl-4,5-dihydropyridazin-3(2H)-one, was conducted in a similar fashion to Example #34 but for using 3-hydroxyazetidine-HCl and $K_2CO_3$ in IPA instead of N-methylamine in Step 2 to afford the Example #37 compound. 1H NMR (400 MHz, DMSO-d6): δ 10.97 (s, 1H), 8.06 (s, 1H), 7.55 (d, 1H), 4.72-4.66 (m, 1H), 4.40-4.36 (m, 2H), 3.96-3.92 (m, 2H), 3.40 (q, 1H), 2.71-2.67 (m, 1H), 2.24 (d, 1H), 1.08 (d, 3H).

Preparation of Example #46, 6-(4-fluoro-2-(3-hydroxyazetidin-1-yl)benzo[d]thiazol-6-yl)-5-methyl-4,5-dihydropyridazin-3(2H)-one, was conducted in a similar fashion to Example #34 but for using (1-methylpyrazol-4-yl) methanamine in IPA instead of N-methylamine in Step 2 to afford the Example #46 compound. 1H NMR (400 MHz, DMSO-d6): δ 10.95 (s, 1H), 8.61 (t, 1H), 7.96 (s, 1H), 7.69 (s, 1H), 7.52 (d, 1H), 7.44 (s, 1H), 4.43 (d, 2H), 3.80 (s, 3H), 3.39 (q, 1H), 2.72-2.68 (m, 1H), 2.24 (d, 1H), 1.08 (d, 3H).

Preparation of Example #35 (8-chloro-6-(4-methyl-6-oxo-1,4,5,6-tetrahydropyridazin-3-yl)quinolin-2(1H)-one)

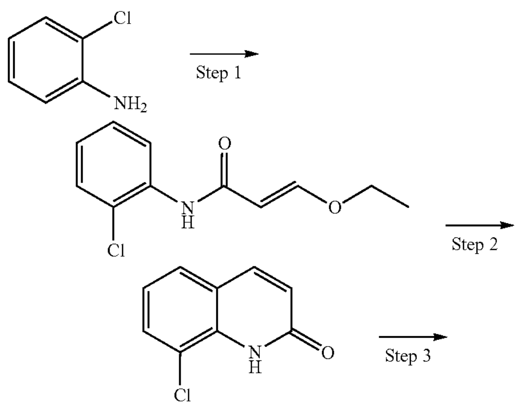

-continued

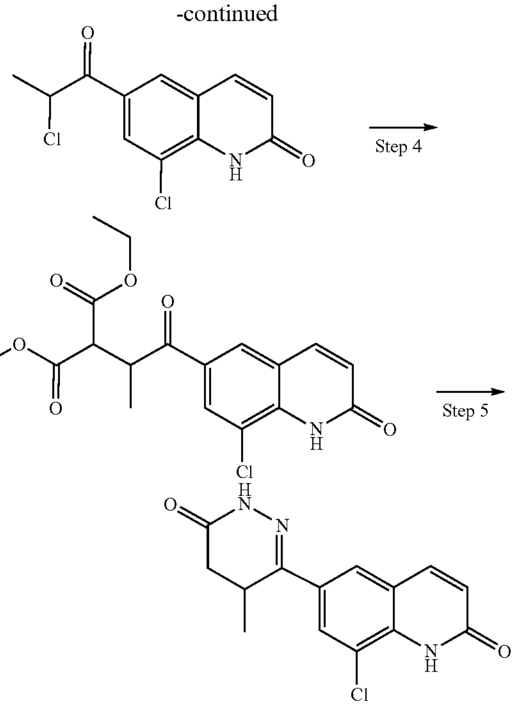

(35)

Step 1. 2-chloroaniline (1.0 g, 7.8 mMol) was dissolved in ethyl acetate (50 mL). Solid sodium bicarbonate (2.0 equiv.) was added followed by the addition of 3-ethoxy-acryloyl chloride (1.2 g, 9.4 mmol, 1.2 equiv.) at room temperature. The mixture was stirred for 3 hours then quenched by the addition of water (10 mL). The reaction was poured into a separatory funnel. The organic layer was collected and washed with water (2×15 mL). The organic phase was collected and dried over sodium sulfate. The volatiles were removed by rotary evaporation to provide (E)-N-(2-chlorophenyl)-3-ethoxyacrylamide which was used directly in the next step.

Step 2. (E)-N-(2-chlorophenyl)-3-ethoxyacrylamide (0.80 g, 3.5 mmol)) was added to cold sulfuric acid (5 mL). The solution was allowed to warm to room temperature where it was stirred for 3 hours. The reaction mixture was poured into ice water (50 mL) resulting in a precipitate forming. The precipitate was collected by suction filtration and washed with water before oven drying overnight to prepare 8-chloroquinolin-2(1H)-one (0.771 g, 4.3 mmol).

Step 3. Aluminium chloride (2.3 g, 17.2 mmol) was added portion wise to a solution of 2-chloropropanoyl chloride (1.6 g, 12.9 mmol) in DCM (10 mL) while the temperature was kept below 30° C. 8-chloroquinolin-2(1H)-one (0.771 g, 4.3 mmol) was added while the temperature was kept below 30° C. The mixture was stirred and refluxed for 15 hours, cooled and poured out into ice water. The precipitate was filtered off, washed with water and taken up in DCM (2 mL). The organic solution was stirred at 0° C. and filtered. The precipitate was dried, yielding 0.79 g (2.7 mmol) of 8-chloro-6-(2-chloropropanoyl)quinolin-2(1H)-one.

Step 4. To anhydrous DMSO (25 mL) was added t-BuOK (490 mg, 4.4 mmol) in an atmosphere of $N_2$. The mixture was stirred for 30 minutes at 30° C. Diethyl malonate (656 mg, 4.4 mmol) was diluted with DMSO (5 mL) and added to the stirring mixture dropwise over a period of 1 hour. The reaction solution was stirred an additional hour at 30° C.

8-chloro-6-(2-chloropropanoyl)quinolin-2(1H)-one (790 mg, 2.7 mmol) was added in three portions to the reaction mixture over a 15 minute period. The reaction was then stirred for 2 hours at 40° C. The reaction mixture was cooled to room temperature and quenched with the addition of acetic acid (2 mL). Water (100 mL) and methylene chloride (50 mL) were added to the reaction in a separatory funnel. The layers were mixed and allowed to partition. The organic phase was collected and washed with brine (3×20 mL). The organic phase was dried over sodium sulfate and concentrated to give the crude product, diethyl 2-(1-(8-chloro-2-oxo-1,2-dihydroquinolin-6-yl)-1-oxopropan-2-yl)malonate, that was used directly in the next step.

Step 5. diethyl 2-(1-(8-chloro-2-oxo-1,2-dihydroquinolin-6-yl)-1-oxopropan-2-yl)malonate (2.7 mmol) was suspended in a 1:1 solution of dioxane/water (10 mL). Sodium hydroxide (0.540 g, 13.5 mmol) was added to the mixture. The mixture was heated at 60° C. for 12 hours. The reaction mixture was allowed to cool to room temperature before AcOH (15 mmol) was added. The reaction mixture was stirred for 10 minutes, frozen and lyophilized to give a crude mixture of diacid and inorganic salts. The mixture was suspended in EtOH and hydrazine monohydrate (0.30 g, 6 mmol) was added to the mixture. The reaction was heated at 65° C. overnight. The reaction mixture was allowed to cool to room temperature. The volatile components were evaporated using rotary evaporation at low pressure to give a white solid. Water (20 mL) was added to the solid and the insoluble material was filtered off to give the crude product as a brown solid (0.4 g). Purification by reverse phase HPLC to afford the Example #35 compound (156 mg, 0.56 mmol). $^1$H NMR (400 MHz, DMSO-d6) δ ppm 1.05-1.13 (m, 3H) 2.24-2.31 (m, 1H) 2.68-2.77 (m, 1H) 3.41-3.51 (m, 1H) 6.61-6.68 (m, 1H) 8.01-8.10 (m, 3H) 11.03-11.07 (m, 1H) 11.22-11.27 (m, 1H).

Example #35 exists as a tautomer, 6-(8-chloro-2-hydroxyquinolin-6-yl)-5-methyl-4,5-dihydropyridazin-3(2H)-one (#35a), shown below:

(35a)

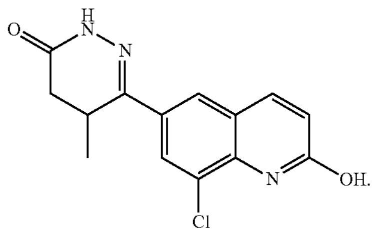

Preparation of Example #36 (7-chloro-6-fluoro-3,3-dimethyl-5-(4-methyl-6-oxo-1,4,5,6-tetrahydropyridazin-3-yl)indolin-2-one)

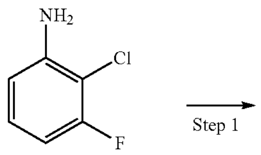

-continued

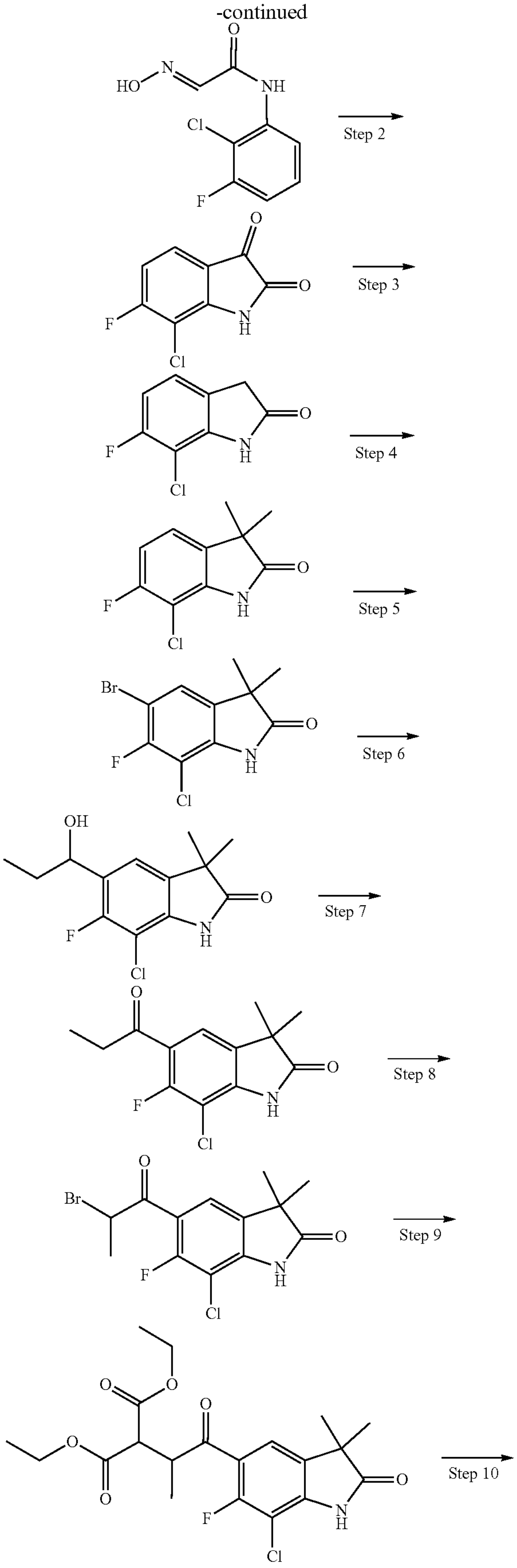

-continued

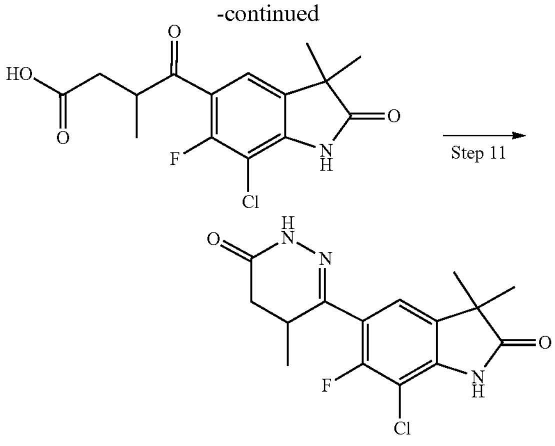

(36)

Step 1. To a stirred solution of chloral hydrate (15.9 g, 96.18 mmol) and sodium sulphate (54.6 g, 384.72 mmol) in water (70 mL) was added 2-chloro-3-fluoroaniline (10.0 g, 68.7 mmol) in concentrated hydrochloric acid (6.9 mL) at room temperature and stirred for 1 hour. Hydroxylamine hydrochloride (6.68 g, 96.18 mmol) was added to the reaction mixture and resulting mixture was heated at 80° C. for 16 hours. Reaction mixture was poured into water and extracted with ethyl acetate. Organic layer was concentrated under reduced pressure to afford (E)-N-(2-chloro-3-fluorophenyl)-2-(hydroxyimino)acetamide (10 g) which was carried to the next step without further purification. MS (ESI): m/z 217.2 $[M+1]^+$.

Step 2. To a stirred solution of (E)-N-(2-chloro-3-fluorophenyl)-2-(hydroxyimino)acetamide (10 g, 46.17 mmol) in concentrate sulphuric acid (30 mL) at 80° C. for 3 hours. Reaction mixture was poured into ice-water and extracted with ethyl acetate. Organic layer was dried over anhydrous sodium sulphate, filtered, and concentrated under reduced pressure. Crude product was purified by combi flash chromatography (20-40% ethyl acetate in hexane) to afford 7-chloro-6-fluoroindoline-2,3-dione (5.6 g, 26%, after two steps) as off white solid. MS (ESI): m/z 200.2 $[M+1]^+$.

Step 3. To a stirred solution of 7-chloro-6-fluoroindoline-2,3-dione (5.6 g, 28.06 mmol) in ethylene glycol (50 mL) was added hydrazine monohydrate (2.81 g, 56.12 mmol) at room temperature and stirred for 4 hours at 130° C. and then at room temperature for 16 hours. Water (50 mL) and concentrate hydrochloric acid (5 mL) was added to the reaction mixture and stirred at 50° C. for 1 hour. The reaction mixture was poured into ice water and extracted with ethyl acetate. Organic layer was dried over anhydrous sodium sulphate, filtered, and concentrated under reduced pressure. Crude product was purified by combiflash chromatography (30-40% EtOAc in hexane) to afford 7-chloro-6-fluoroindolin-2-one (3.9 g, 75%) as brown solid. MS (ESI): m/z 186.2 $[M+1]^+$.

Step 4. To a stirred solution of 7-chloro-6-fluoroindolin-2-one (3.9 g, 21.02 mmol) in tetrahydrofuran (40 mL) was added lithium chloride (2.67 g, 63.05 mmol) at room temperature and the reaction mixture was cooled to −78° C. followed by addition of LDA (2M in THF, 21 mL, 42.03 mmol). Reaction mixture was allowed to stir at −78° C. for 15 minutes followed by addition of methyl iodide (2.6 mL, 42.03 mmol). After addition the reaction mixture was allowed to attain room temperature and stirred for 2 hour. Reaction mixture was quenched with saturated ammonium chloride solution and extracted with ethyl-acetate. The organic layer was dried over anhydrous sodium sulphate, filtered, and concentrated under reduced pressure. Crude product was purified by combi flash chromatography (20-30% ethyl acetate in hexane) to afford 7-chloro-6-fluoro-3,3-dimethylindolin-2-one (1.5 g, 33%) as brown solid. MS (ESI): m/z 214.2 $[M+1]^+$.

Step 5. To a stirred solution of 7-chloro-6-fluoro-3,3-dimethylindolin-2-one (3.0 g, 14.04 mmol) in concentrate sulphuric acid (30 mL) was added n-bromo succinimide (3.75 g, 21.06 mmol) portion wise at room temperature and stirred for 1 hour. Reaction mixture was poured into ice water and extracted with ethyl acetate. Organic layer was dried over anhydrous sodium sulphate, filtered, and concentrated under reduced pressure. Crude product was purified by combi flash chromatography (30-40% ethyl acetate in hexane) to afford 5-bromo-7-chloro-6-fluoro-3,3-dimethylindolin-2-one (3.8 g, 92%) as off white solid. MS (ESI): m/z 292.2 $[M+1]^+$.

Step 6. To a stirred nBuLi (13.4 mL, 28.32 mmol, 2M in THF) in THF (30 mL) was added iPrMgCl·LiCl (10.52 mL, 2 equivalents, 1.3M in THF) at 0° C. and stirred for 10 minutes. A solution of 5-bromo-7-chloro-6-fluoro-3,3-dimethylindolin-2-one (2 g, 7.08 mmol) in THF (10 mL) was added to the reaction mixture and stirred for 1 hour. The reaction mixture was cooled to −78° C. and added propionaldehyde (2.47 g, 42.47 mmol), stirred at −78° C. for 2 hours. Reaction mixture was quenched with saturated ammonium chloride and extracted with ethyl acetate. Organic layer was dried over anhydrous sodium sulphate, filtered, and concentrated under reduced pressure. Crude product was purified by combi flash chromatography (30-40% ethyl acetate in hexane) to afford 7-chloro-6-fluoro-5-(1-hydroxypropyl)-3,3-dimethylindolin-2-one (0.85 g, 44%) as liquid. MS (ESI): m/z 272.2 $[M+1]^+$.

Step 7. To a stirred solution of compound 7-chloro-6-fluoro-5-(1-hydroxypropyl)-3,3-dimethylindolin-2-one (1.7 g, 6.25 mmol) in dichloromethane (50 mL) was added Dess martin periodinane (5.308 mg, 12.51 mmol) at temperature and then stirred at room temperature for 16 hours. The reaction mixture was filtered through celite bed and washed with ethyl acetate. Filtrate was concentrated under reduced pressure to get crude compound which was purified by combi flash column chromatography (40-50% ethyl acetate in hexane) to afford 7-chloro-6-fluoro-3,3-dimethyl-5-propionylindolin-2-one (0.5 g, 30%) as liquid. MS (ESI): m/z 270.2 $[M+1]^+$.

Step 8. To a stirred solution of 7-chloro-6-fluoro-3,3-dimethyl-5-propionylindolin-2-one (500 mg, 0.37 mmol) in tetrahydrofuran (20 mL) was added n-bromo succinimide (660 mg, 3.71 mmol) portion wise at room temperature and stirred for 16 hours. Reaction mixture was poured into ice water and extracted with ethyl acetate. Combined organic layer was washed with brine, dried over anhydrous sodium sulphate, filtered, and concentrated under reduced pressure. Crude product was purified by combi flash column chromatography (20-30% ethyl acetate in hexane) to afford 5-(2-bromopropanoyl)-7-chloro-6-fluoro-3,3-dimethylindolin-2-one (0.6 g, 92%) as yellow solid. MS (ESI): m/z 348.2 $[M+1]^+$.

Step 9. To a stirred solution of DMSO (7 mL) was added portion-wise three times of potassium tert-butoxide (251 mg, 2.24 mmol) at room temperature and stirred for 20 minutes. A solution of diethyl malonate (238 mg, 3.75 mmol) in DMSO (1 mL) was added to the reaction mixture and stirred for 20 minutes. A solution of 5-(2-bromopropanoyl)-7-chloro-6-fluoro-3,3-dimethylindolin-2-one (600 mg, 1.72 mmol) in DMSO (2 mL) was added to the reaction mixture and stirred for 3 hours. After completion of the reaction quenched with acetic acid (176 mg, 2.93 mmol). The reaction mixture was diluted with water and extracted with ethyl acetate. Organic layer was dried over anhydrous sodium sulphate, filtered, and concentrated under reduce pressure. Crude mass was purified by combi flash column chromatography (5-10% ethyl acetate in hexane) to afford diethyl 2-(1-(7-chloro-6-fluoro-3,3-dimethyl-2-oxoindolin-5-yl)-1-oxopropan-2-yl) malonate (0.24 g, 33%) as an off white solid. MS (ESI): m/z 428.2 $[M+1]^+$.

Step 10. To a stirred solution compound 1 (240.0 mg, 0.56 mmol) in 1,4-dioxane (3 mL) was added concentrated hydrochloric acid (7.0 mL, 6N) at room temperature and stirred for 16 hours at 90° C. The reaction mixture was diluted with ice-water and extracted with ethyl acetate. Combined organic layer was concentrated under reduced pressure to afford 4-(7-chloro-6-fluoro-3,3-dimethyl-2-oxoindolin-5-yl)-3-methyl-4-oxobutanoic acid (200 mg, crude) as an off white solid which was forwarded to the next step. MS (ESI): m/z 328.2 $[M+1]^+$.

Step 11. To a stirred solution of 4-(7-chloro-6-fluoro-3,3-dimethyl-2-oxoindolin-5-yl)-3-methyl-4-oxobutanoic acid (200.0 mg, 0.61 mmol) in ethanol (4 mL) was added hydrazine monohydrate (0.2 mL, 3.05 mmol) at room temperature. Reaction mixture was stirred at 80° C. for 16 hours. After completion, reaction mixture was cooled at room temperature and concentrated under reduced pressure. Crude product was purified by reverse phase preparative HPLC to afford the Example #36 compound (35.8 mg, 25% in two steps) as a white solid (99.36% purity). 1H NMR (400 MHz, DMSO-d6): δ 11.17 (s, 1H), 11.02 (s, 1H), 7.50 (d, J=6.8 Hz, 1H), 3.18-3.13 (m, 1H), 2.72-2.66 (m, 1H), 2.27-2.22 (m, 1H), 1.29 (s, 6H), 1.06 (d, J=7.16 Hz, 3H).

Preparation of Example #38 (2-amino-6-(4-methyl-6-oxo-1,4,5,6-tetrahydropyridazin-3-yl)benzo[d]thiazole-4-carbonitrile)

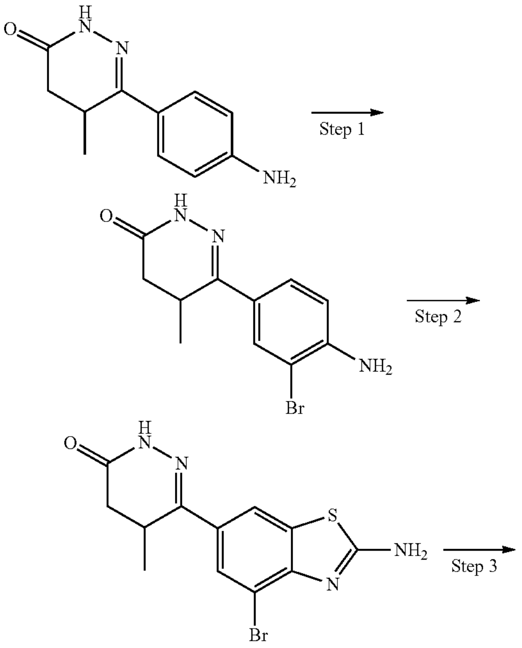

-continued

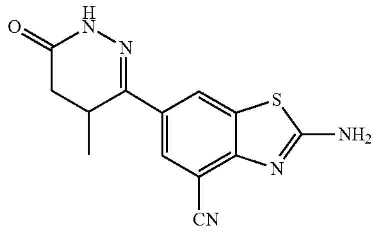

(38)

Step 1. 6-(4-amino-3-bromophenyl)-5-methyl-4,5-dihydropyridazin-3(2H)-one. The preparation of this intermediate was conducted in a similar fashion to the intermediate in Step 1 of Example #30, but for using NBS instead of NCS. LC/MS M+H=282.

Step 2. 6-(2-amino-4-bromobenzo[d]thiazol-6-yl)-5-methyl-4,5-dihydropyridazin-3(2H)-one. The preparation of this intermediate was conducted in a similar fashion to the intermediate in Step 2 of Example #30. LC/MS M+H=339.

Step 3. A mixture of 6-(2-amino-4-bromobenzo[d]thiazol-6-yl)-5-methyl-4,5-dihydropyridazin-3(2H)-one (100 mg, 0.3 mmol), $Zn(CN)_2$ (42 mg, 0.35 mmol) and $Pd(dppf)Cl_2$ (22 mg, 0.03 mmol) in DMF (4 mL) was heated to 150° C. for 2 hours under microwave irradiation. The reaction mixture was subsequently cooled, extracted with EtOAc:MeOH (100 mL, 95:5), and washed with water. The organic phase was dried ($Na_2SO_4$), concentrated under reduced pressure, and the crude product was purified using reverse-phase chromatography eluting from 95:5:0.1 water:MeCN:TFA to 75:25:0.1 MeCN:water:TFA over 20 minutes to afford the Example #38 compound (15 mg, 13%) as a solid. 1H NMR (400 MHz, DMSO-d6): δ 11.0 (s, 1H), 8.40-8.36 (m, 3H), 7.98 (s, 1H), 3.43 (q, 1H), 2.73-2.68 (m, 1H), 2.24 (d, 1H), 1.08 (d, 3H).

Preparation of Example #40 (6-(4-methyl-6-oxo-1,4,5,6-tetrahydropyridazin-3-yl)-2-oxo-1,2-dihydroquinoline-8-carbonitrile)

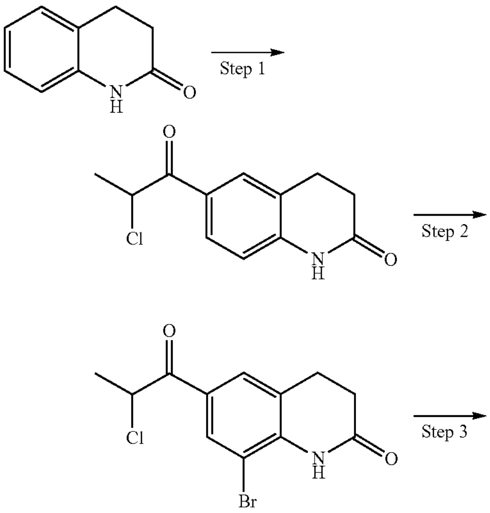

-continued

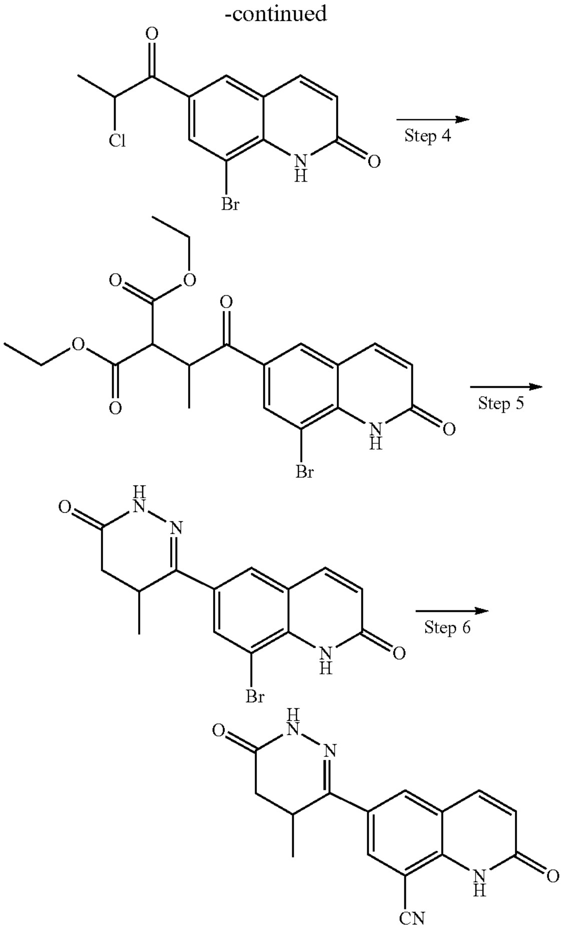

(40)

Step 1. To a 1,2-dichloroethane (20 mL) solution of 3,4-dihydroquinolin-2(1H)-one (1.0 g, 6.8 mmol) a 2-chloropropanoyl chloride (1.27 g, 10.2 mmol) was added aluminum trichloride (3.6 g, 27 mmols) in three equal portions over 15 minutes. The mixture was heated to 60° C. in an atmosphere of nitrogen for five hours. The reaction was cooled to room temperature and poured into ice water (100 mL). The volatiles were removed by rotary evaporation at low pressure which caused a precipitate to form. The precipitate was collected by suction filtration and washed with water (2x25 mL). Upon drying, the crude product, 6-(2-chloropropanoyl)-3,4-dihydroquinolin-2(1H)-one, weighed 0.8 g and was used as is in the next step.

Step 2. 6-(2-chloropropanoyl)-3,4-dihydroquinolin-2 (1H)-one (0.80 g, 3.4 mmol) was dissolved in DMF (5 mL) and NBS (1.2 g, 6.8 mmol) was added. The solution was warmed at 80° C. for 12 hours. The reaction was poured into ice water (50 mL) and the precipitate collected by suction filtration. The precipitate was washed with water (3x20 mL) and dried, to provide the product, 8-bromo-6-(2-chloropropanoyl)-3,4-dihydroquinolin-2(1H)-one, (0.94 g, 3.0 mmol).

Step 3. To a solution of 8-bromo-6-(2-chloropropanoyl)-3,4-dihydroquinolin-2(1H)-one (0.94 g, 3.0 mmol) and NBS (0.67 g, 3.8 mmol) was added benzoyl peroxide (catalytic amount). The mixture was refluxed for 5 hours. The volatiles were evaporated and the residual solid was partitioned between water (25 mL) and ethyl acetate (50 mL). The organic phase was washed with water (25 mL), dried and concentrated. The product, 8-bromo-6-(2-chloropropanoyl)-3,4-dihydroquinolin-2(1H)-one, (0.54 g, 1.7 mmol) was obtained after flash column chromatography using a gradient of ethyl acetate in hexanes.

Step 4. To anhydrous DMSO (15 mL) was added t-BuOK (280 mg, 2.5 mmol) in an atmosphere of $N_2$. The mixture was stirred for 30 minutes at 30° C. Diethyl malonate (410 mg, 2.5 mmol) was diluted with DMSO (5 mL) and added to the stirring mixture dropwise over a period of 1 hour. The reaction solution was stirred an additional hour at 30° C. 8-bromo-6-(2-chloropropanoyl)-3,4-dihydroquinolin-2 (1H)-one (540 mg, 1.7 mmol) was added in three portions to the reaction mixture over 15 minutes. The reaction was then stirred for 2 hours at 40° C. The reaction mixture was cooled to room temperature and quenched with the addition of acetic acid (2 mL). Water (50 mL) and methylene chloride (30 mL) were added to the reaction in a separatory funnel. The layers were mixed and allowed to partition. The organic phase was collected and washed with brine (3x20 mL). The organic phase was dried over sodium sulfate and concentrated to give the crude product, diethyl 2-(1-(8-bromo-2-oxo-1,2-dihydroquinolin-6-yl)-1-oxopropan-2-yl)malonate, that was used directly in the next step.

Step 5. diethyl 2-(1-(8-bromo-2-oxo-1,2-dihydroquinolin-6-yl)-1-oxopropan-2-yl)malonate (1.7 mmol) was suspended in a 1:1 solution of dioxane/water (10 mL). Sodium hydroxide (0.340 g, 8.5 mmol) was added to the mixture. The mixture was heated at 60° C. for 12 hours. The reaction mixture was allowed to cool to room temperature before AcOH (10 mmol) was added. The reaction mixture was stirred for 10 minutes then frozen and lyophilized to give a mixture of white solids. The mixture was suspended in EtOH (10 mL) and hydrazine monohydrate (0.175 g, 3.5 mmol) was added to the mixture. The reaction was heated at 65° C. overnight. The reaction mixture was allowed to cool to room temperature. The volatile components were evaporated using rotary evaporation at low pressure to give a white solid. Water (20 mL) was added to the solid and the insoluble material was filtered off to give the crude product as a brown solid (0.21 g). Purification by reverse phase HPLC gave the pure product, 8-bromo-6-(4-methyl-6-oxo-1,4,5,6-tetrahydropyridazin-3-yl)quinolin-2(1H)-one (171 mg, 0.51 mmol)

Step 6. 8-bromo-6-(4-methyl-6-oxo-1,4,5,6-tetrahydropyridazin-3-yl)quinolin-2(1H)-one (171 mg, 0.51 mmol), $Zn(CN)_2$ (117 mg, 1.0 mmol), $Pd_2(dba)_3$ (47 mg, 0.051 mmol) and zinc dust (32 mg, 0.5 mmol) were added to a three necked round bottom flask followed by addition of DMF (10 mL). Nitrogen gas was bubbled into the reaction mixture for 10 minutes. $P(tBu)_3$ (100 mg, 0.025 mmol) was added as a solution in hexanes (1 mg). The reaction mixture was then stirred in an atmosphere of nitrogen at 50° C. for 5 hours. The reaction mixture was cooled to room temperature and 30 mL of ice water were added while stirring. The precipitate was collected by suction filtration and purified by reverse phase HPLC to afford the Example #40 compound (8 mg, 0.029 mmol), as a beige solid. 1H NMR (400 MHz, DMSO-d6) δ ppm 1.10 (d, J=7.34 Hz, 3H) 2.11-2.35 (m, 1H) 2.61-2.86 (m, 2H) 3.34-3.61 (m, 1H) 6.73 (br s, 1H) 8.34 (br s, 1H) 8.43 (br s, 1H) 11.11 (s, 1H) 11.81 (br s, 1H).

Example #40 exists as a tautomer, 2-hydroxy-6-(4-methyl-6-oxo-1,4,5,6-tetrahydropyridazin-3-yl)quinoline-8-carbonitrile (#40a), as shown below:

(40a)

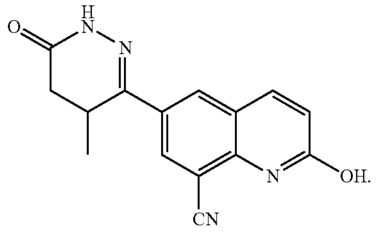

Preparation of Example #41 (7-chloro-3,3-dimethyl-5-(4-methyl-6-oxo-1,4,5,6-tetrahydropyridazin-3-yl)-2,3-dihydro-1H-isoindol-1-one)

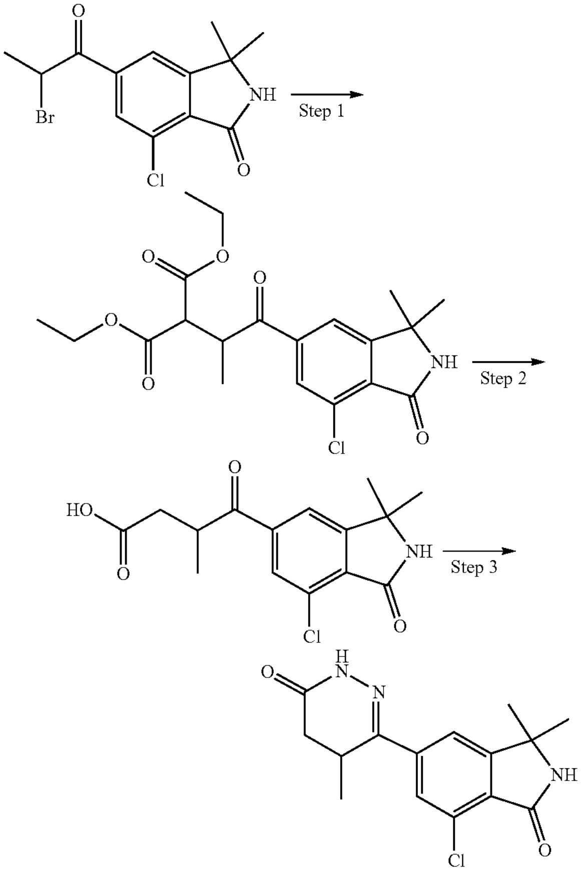

(41)

Step 1. To a stirred solution of potassium tert-butoxide (221 mg, 1.98 mmol) in dimethyl sulfoxide (5 mL) was added a solution of diethyl malonate (260 mg, 1.97 mmol) in DMSO (2 mL) drop wise over 10 minutes and stirred at room temperature for 40 minutes. A solution of 5-(2-bromopropanoyl)-7-chloro-3,3-dimethyl-2,3-dihydro-1H-isoindol-1-one (500 mg, 1.52 mmol) in DMSO (5 mL) was added drop wise over 10 minutes at 0° C. under argon atmosphere. Resulting mixture was slowly warmed to room temperature and stirred for 3 hours. After completion, reaction mixture was quenched with saturated aqueous ammonium chloride solution at 0° C. and extracted with ethyl acetate. Combined organic layer was washed with brine, dried over anhydrous sodium sulphate, filtered and concentrated under reduced pressure. Crude product was purified by combiflash chromatography (30-50% EtOAc in hexane) to afford 1,3-diethyl 2-[1-(7-chloro-3,3-dimethyl-1-oxo-2,3-dihydro-1H-isoindol-5-yl)-1-oxopropan-2-yl]propanedioate (320 mg, 51%) as yellow solid. MS (ESI): m/z 410 [M+1]+.

Step 2. A solution of 1,3-diethyl 2-[1-(7-chloro-3,3-dimethyl-1-oxo-2,3-dihydro-1H-isoindol-5-yl)-1-oxopropan-2-yl]propanedioate (130 mg, 0.318 mmol) in 6N aqueous hydrochloric acid (5 mL) was heated at 90° C. for 16 hours. After completion, volatiles were removed under reduced pressure and residue was co-distilled with toluene for twice. Crude product was triturated with diethyl ether to obtain 4-(7-chloro-3,3-dimethyl-1-oxo-2,3-dihydro-1H-isoindol-5-yl)-3-methyl-4-oxobutanoic acid (90 mg, crude) as brown gum which was carried to the next step without further purification. MS (ESI): m/z 310.1 $[M+1]^+$.

Step 3. To a stirred solution of 4-(7-chloro-3,3-dimethyl-1-oxo-2,3-dihydro-1H-isoindol-5-yl)-3-methyl-4-oxobutanoic acid (90 mg, 0.29 mmol) in ethanol (5 mL) was added hydrazine mono hydrate (0.06 ml, 1.16 mmol) at room temperature. Resulting mixture was heated at 90° C. for 16 hours. After completion, volatiles were removed under reduced pressure and obtained crude product was purified by reverse phase preparative HPLC to afford the Example #41 compound (12 mg) as an off-white solid (97.52% purity). 1H NMR (400 MHz, DMSO-d6): δ 11.15 (s, 1H), 8.82 (s, 1H), 7.95 (s, 1H), 7.77 (s, 1H), 3.51-3.48 (m, 1H), 2.78-2.72 (m, 1H), 2.32-2.25 (m, 1H), 1.46 (s, 6H), 1.08 (d, J=7.2 Hz, 3H).

Preparation of Example #42 (4-chloro-1-methyl-6-(4-methyl-6-oxo-1,4,5,6-tetrahydropyridazin-3-yl)-1,3-dihydro-2H benzo[d]imidazol-2-one)

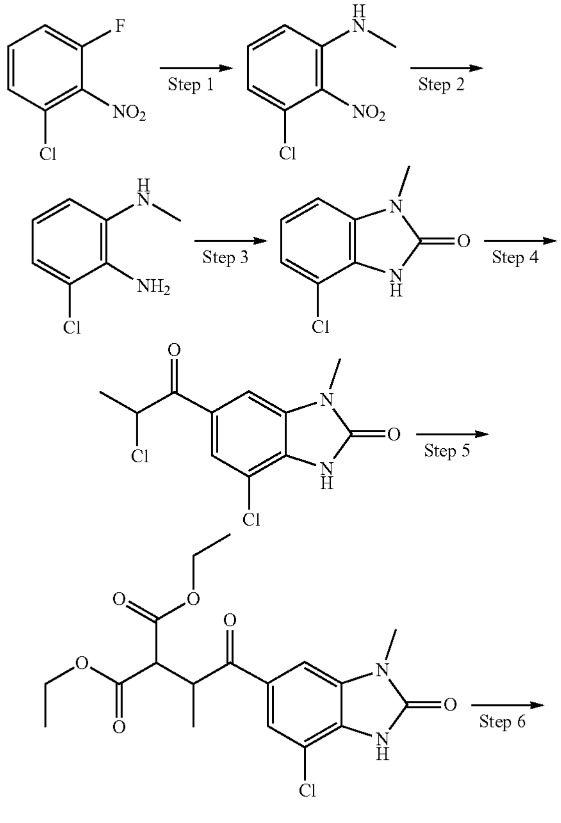

-continued

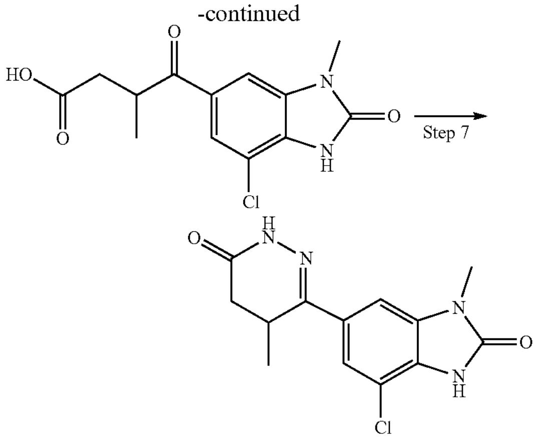

(42)

Step 1. To a stirred solution of 1-chloro-3-fluoro-2-nitrobenzene (1.0 g, 5.71 mmol) in EtOH (2 mL) was added methylamine solution (10 mL, 20 mmol, 2M in THF) and stirred at 90° C. for 16 hours. After completion, volatiles were removed under reduced pressure and crude product was purified by combiflash chromatography (20-40% EtOAc in hexane) to afford 3-chloro-N-methyl-2-nitroaniline (0.91 g, 85%) as an off white solid. MS (ESI): m/z 187.0 $[M+1]^+$.

Step 2. To a stirred solution of 3-chloro-N-methyl-2-nitroaniline (2.0 g, 10.75 mmol) in methanol (30 mL) at 0° C., was added ammonium formate (6.8 g, 107.53 mmol) and stirred at 0° C. for 20 minutes. Zinc dust (7.1 g, 107.53 mmol) was added portion wise to the reaction mixture at 0° C. and stirred at room temperature for 16 hours. After completion, the reaction mixture was filtered, washed with ethyl acetate and combined filtrate was evaporated under reduced pressure. Residue was diluted with water and extracted twice with ethyl acetate. Combined organic layer was washed with brine, dried over anhydrous sodium sulphate, filtered and concentrated under reduced pressure. Crude product was purified by combiflash chromatography (40-60% EtOAc in hexane) to afford 3-chloro-$N^1$-methylbenzene-1,2-diamine (3.95 g, 67%) as off white solid. MS (ESI): m/z 157.0 $[M+1]^+$.

Step 3. To a stirred solution of 3-chloro-$N^1$-methylbenzene-1,2-diamine (1.3 g, 8.33 mmol) in dichloromethane (10 mL) was added triethylamine (1.39 mL, 10.0 mmol) at 0° C. Triphosgene (3.71 g, 12.5 mmol) was added portion wise under cooling condition. Reaction mixture was allowed to attain room temperature and stirred for 5 h. After completion, volatiles were removed under reduced pressure and the residue was diluted with water and extracted with dichloromethane. Combined organic layer was washed with brine, dried over anhydrous sodium sulphate, filtered and concentrated under reduced pressure. Crude product was purified by combiflash chromatography (30-50% EtOAc in hexane) to afford 4-chloro-1-methyl-1,3-dihydro-2H-benzo[d]imidazol-2-one (0.5 g, 31%) as off white solid. MS (ESI): m/z 183.0 $[M+1]^+$.

Step 4. A slurry of aluminium chloride (7.33 g, 54.95 mmol) and DMF (1.41 mL, 18.13 mmol) was heated at 80° C. for 15 minutes. Resulting mixture was cooled to room temperature and 4-chloro-1-methyl-1,3-dihydro-2H-benzo[d]imidazol-2-one (1 g, 5.5 mmol) was added portion wise and maintained the temperature below 40° C. while addition was done. 2-chloropropanoyl chloride (0.52 mL, 6.87 mmol) was added drop-wise and stirred at 80° C. for 2 hours. After completion, reaction mixture was poured into crushed ice-water and extracted with ethyl acetate. Combined organic layer was washed with brine, dried over anhydrous sodium sulphate, filtered and concentrated under reduced pressure. Crude product was purified by combiflash chromatography (40-60% EtOAc in hexane) to afford 4-chloro-6-(2-chloropropanoyl)-1-methyl-1,3-dihydro-2H-benzo[d]imidazol-2-one (0.19 g, 11%) as off white solid. MS (ESI): m/z 273.0 $[M+1]^+$.

Step 5. To a stirred solution of potassium tert-butoxide (3.09 g, 27.57 mmol) in DMSO (30 mL) was added a solution of diethyl malonate (4.41 g, 27.57 mmol) in DMSO (25 mL) drop wise over 10 minutes and stirred at room temperature for 40 minutes. A solution of 4-chloro-6-(2-chloropropanoyl)-1-methyl-1,3-dihydro-2H-benzo[d]imidazol-2-one (5 g, 18.38 mmol) in DMSO (25 mL) was added drop wise over 10 minutes at 0° C. under argon atmosphere. Resulting mixture was slowly warmed to room temperature and stirred for 3 hours. After completion, reaction mixture was quenched with saturated aqueous ammonium chloride solution at 0° C. and extracted with ethyl acetate. Combined organic layer was washed with brine, dried over anhydrous sodium sulphate, filtered and concentrated under reduced pressure. Crude product was purified by combiflash chromatography (30-50% EtOAc in hexane) to afford diethyl 2-(1-(7-chloro-3-methyl-2-oxo-2,3-dihydro-1H-benzo[d]imidazol-5-yl)-1-oxopropan-2-yl)malonate (3 g, 48%) as off white solid. MS (ESI): m/z 397.0 $[M+1]^+$.

Step 6. A stirred solution of diethyl 2-(1-(7-chloro-3-methyl-2-oxo-2,3-dihydro-1H-benzo[d]imidazol-5-yl)-1-oxopropan-2-yl)malonate (3 g, 7.56 mmol) in 6N aqueous hydrochloric acid (50 mL) was heated at 90° C. for 16 hours. After completion, volatiles were removed under reduced pressure and the residue was co-distilled with toluene twice. Crude product was triturated with diethyl ether to afford 4-(7-chloro-3-methyl-2-oxo-2,3-dihydro-1H-benzo[d]imidazol-5-yl)-3-methyl-4-oxobutanoic acid (1.2 g, crude) as brown gum which was carried to the next step without further purification. MS (ESI): m/z 295.0 $[M-1]^+$.

Step 7. To a stirred solution of 4-(7-chloro-3-methyl-2-oxo-2,3-dihydro-1H-benzo[d]imidazol-5-yl)-3-methyl-4-oxobutanoic acid (500.0 mg, 1.69 mmol, crude) in ethanol (20 mL) was added hydrazine mono hydrate (0.34 ml, 6.76 mmol) at room temperature. Resulting mixture was heated at 90° C. for 16 hours. After completion, volatiles were removed under reduced pressure and obtained crude product was purified by reverse phase preparative HPLC to afford the Example #42 compound (18 mg, 4% in two steps) as an off-white solid (93.65% purity). 1H NMR (400 MHz, DMSO-d6, 100° C.): δ 10.63 (s, 1H), 10.35 (brs, 1H), 7.44-7.41 (m, 2H), 3.44 (m, 1H), 3.34 (s, 3H), 2.71-2.67 (m, 1H), 2.33-2.2 (m, 1H), 1.06 (d, J=6.4 Hz, 3H).

Preparation of Example #43 (7'-fluoro-5'-(4-methyl-6-oxo-1,4,5,6-tetrahydropyridazin-3-yl)spiro[cyclobutane-1,3'-indolin]-2'-one)

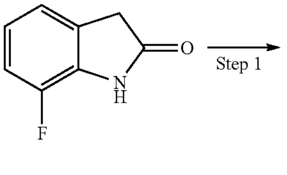

-continued

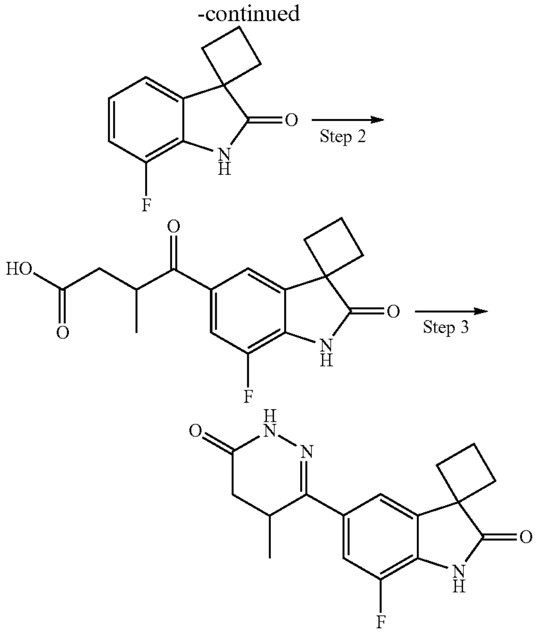

(43)

Step 1. 7-fluoroindolin-2-one (2.0 g, 13.2 mmol) and LiCl (1.7 g, 39.7 mmol) were added in THE (50 mL) and the mixture was cooled to −78° C. Next, n-BuLi (17.0 mL, 26.5 mmol) was added slowly and the reaction mixture was stirred at −78° C. for ~30 minutes. 1,3-dibromopropane (2.0 mL, 19.9 mmol) was slowly added and the reaction mixture was allowed to warm to room temperature while stirring overnight. The reaction mixture was quenched with 0.1 N HCl (75 mL) and extracted with EtOAc (2×75 mL). The combined organic phase was dried ($Na_2SO_4$) and concentrated under vacuum. The crude material was chromatographed (80 g Redi-Sep column) eluting from 100% hexanes to 30:70 EtOAc:hexanes to afford 7'-fluorospiro[cyclobutane-1,3'-indolin]-2'-one as a solid. LC/MS M+H=192.

Step 2. DMF (0.55 mL, 7.1 mmol) was added dropwise to anhydrous $AlCl_3$ (3.3 g, 24.0 mmol), the mixture was stirred at 70° C. for ~15 minutes then cooled to 40° C. Next, 7'-fluorospiro[cyclobutane-1,3'-indoline]-2'-one (500 mg, 1.6 mmol) and 3-methyltetrahydrofuran-2,5-dione (450 mg, 3.9 mmol) were slowly added. The reaction mixture was heated to 70° C. for 2 hours and next slowly poured onto ice water, filtered, and air-dried to afford the 4-(7'-fluoro-2'-oxospiro[cyclobutane-1,3'-indolin]-5'-yl)-3-methyl-4-oxobutanoic acid as a mixture of regio-isomers. LC/MS M+H=306.

Step 3. To a solution of crude 4-(7'-fluoro-2'-oxo-spiro[cyclobutane-1,3'-indoline]-5'-yl)-3-methyl-4-oxo-butanoic acid (150 mg, 0.49 mmol) in EtOH (15 mL) was added hydrazine-hydrate (0.2 mL, 1.9 mmol). The reaction was heated to 80° C. for 18 hours. The reaction mixture was cooled in an ice bath, filtered, and washed with cold EtOH. The precipitate was dried under vacuum. The crude regioisomeric mixture was purified using reverse-phase chromatography eluting from 95:5:0.1 water:MeCN:TFA to 80:20:0.1 MeCN:water:TFA collecting the minor regio-isomer as the Example #43 compound. 1H NMR (400 MHz, DMSO-d6): δ 10.95-10.93 (m, 2H), 7.85 (s, 1H), 7.49 (d, 2H), 3.46 (q, 1H), 2.72-2.68 (m, 1H), 2.49-2.33 (m, 5H), 2.29-2.15 (m, 3H), 1.08 (d, 3H).

Preparation of Example #50, 7-fluoro-5-(4-methyl-6-oxo-1,4,5,6-tetrahydropyridazin-3-yl)indolin-2-one, was conducted in a similar fashion to Example #6 but for 4-(7-fluoro-2-oxoindolin-5-yl)-3-methyl-4-oxobutanoic acid instead of 4-(7-chloro-2-oxoindolin-5-yl)-3-methyl-4-oxobutanoic acid to afford the Example #50 compound. 1H NMR (400 MHz, DMSO-d6): δ 11.03 (s, 1H), 10.93 (s, 1H), 7.51-7.47 (m, 2H), 3.61 (s, 2H), 3.37 (q, 1H), 2.68-2.64 (m, 1H), 2.22 (d, 1H), 1.05 (d, 3H).

Preparation of Example #74, 5-(7-fluoro-3,3-dimethyl-2-oxoindolin-5-yl)-6-methyl-3,6-dihydro-2H-1,3,4-thiadiazin-2-one, was conducted in a similar fashion to Example #57 but for 7-fluoro-3,3-dimethylindolin-2-one instead of 7-fluoro-2,3-dihydro-1H-indol-2-one to afford the Example #74 compound. 1H NMR (400 MHz, DMSO-d6): δ 11.66 (s, 1H), 11.09 (s, 1H), 7.65 (s, 1H), 7.55 (d, 1H), 4.73 (q, 1H), 1.47 (d, 3H), 1.31 (s, 6H).

Preparation of Example #57 (5-(7-fluoro-2-oxoindolin-5-yl)-6-methyl-3,6-dihydro-2H-1,3,4-thiadiazin-2-one)

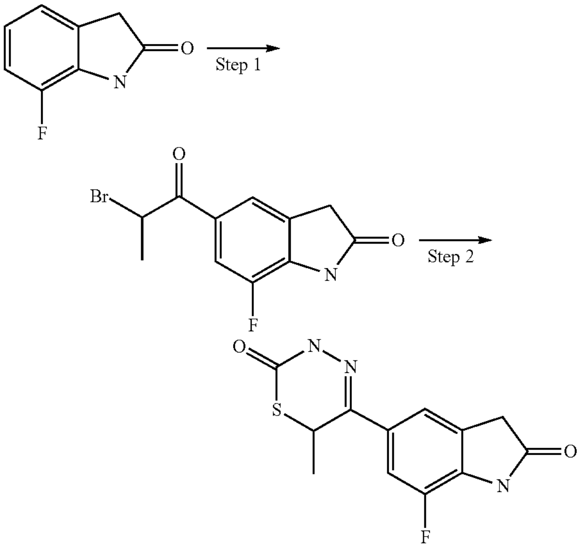

(57)

Step 1. Dimethyl formamide (7.7 mL, 99.27 mmol) was added drop wise to anhydrous aluminum chloride (47.12 g, 330.91 mmol) and stirred at 70° C. for 15 minutes. Resulting mixture was cooled to 40° C. and 7-fluoro-2,3-dihydro-1H-indol-2-one (5 g, 49.64 mmol) and 2-bromopropanoyl chloride (5.1 mL, 49.64 mmol) were slowly added and stirred at 70° C. for 2 hours. After completion, the reaction mixture was diluted with ice water and extracted with ethyl acetate. Combined organic layer was washed with brine, dried over anhydrous sodium sulphate, filtered and concentrated under reduced pressure. Crude product was purified by combiflash chromatography (30-40% EtOAc in hexane) to afford 5-(2-bromopropanoyl)-7-fluoro-2,3-dihydro-1H-indol-2-one (3 g, 32%) as a brown solid. MS (ESI): m/z 286.1 $[M+1]^+$. Alternatively, 2-chloropropanoyl chloride can be substituted in place of 2-bromopropanoyl chloride to make 5-(2-chloropropanoyl)-7-fluoro-2,3-dihydro-1H-indol-2-one, followed by step 2 to afford the Example 57 compound.

Step 2. To a stirred solution of 5-(2-bromopropanoyl)-7-fluoro-2,3-dihydro-1H-indol-2-one (3 g, 10.53 mmol) in ethanol (30 mL) was added [(methoxymethanethioyl)amino]amine (1.12 g, 10.53 mmol) at room temperature under argon atmosphere. The resulting mixture was heated at 80° C. for 16 hours. After completion, the reaction mixture was evaporated to dryness and crude product thus obtained was purified by column chromatography (50-60% EtOAc in hexane) to afford the Example #57 compound (1 g, 34%) as a brown solid. 1H NMR (400 MHz, DMSO-d6): δ 11.66 (br s, 1H), 11.10 (br s, 1H), 7.57-7.56 (m, 2H), 4.72-4.70 (m, 1H), 3.63 (s, 2H), 1.46 (d, J=6.8 Hz, 3H). LCMS: Retention time=1.92 minutes; m/z 278.0 $[M-1]^+$; HPLC purity=97.5%. Example #78 is the (S) isomer of Example #57 and was resolved by HPLC (column I-cellulose Z 150×4.6 mm, 3μ; mobile phase (hexane/ethanol/isopropylamine (70/30/0.1); flow rate 1.0 mL/minute)). HPLC retention time for Example #57 and #78 was 4.22 and 5.11 minutes, respectively.

Preparation of Example #55, 4-methyl-6-(6-methyl-2-oxo-3,6-dihydro-2H-1,3,4-thiadiazin-5-yl)benzo[d]thiazol-2 (3H)-one was conducted in a similar fashion to Example #57 but for 4-methylbenzo[d]thiazol-2 (3H)-one instead of 7-fluoro-2,3-dihydro-1H-indol-2-one to afford the Example #55 compound. 1H NMR (400 MHz, DMSO-d6): δ 11.93 (s, 1H), 11.62 (s, 1H), 7.83 (s, 1H), 7.55 (s, 1H), 4.72-4.66 (m, 1H), 2.36 (s, 3H), 1.47 (d, J=7.2, 3H).

Preparation of Example #56, 4-chloro-6-(6-methyl-2-oxo-3,6-dihydro-2H-1,3,4-thiadiazin-5-yl)benzo[d]thiazol-2 (3H)-one, was conducted in a similar fashion to Example #57 but for 4-chlorobenzo[d]thiazol-2 (3H)-one instead of 7-fluoro-2,3-dihydro-1H-indol-2-one to afford the Example #56 compound. 1H NMR (400 MHz, DMSO-d6): δ 12.47 (s, 1H), 11.76 (s, 1H), 8.04 (d, J=1.6 Hz, 1H), 7.77 (d, J=1.6 Hz, 1H), 4.75-4.70 (m, 1H), 1.47 (d, J=7.2 Hz, 3H).

Preparation of Example #58, 5-(7'-chloro-2'-oxospiro[cyclopropane-1,3'-indolin]-5'-yl)-6-methyl-3,6-dihydro-2H-1,3,4-thiadiazin-2-one, was conducted in a similar fashion to Example #57 but for 7'-chlorospiro[cyclopropane-1,3'-indolin]-2'-one instead of 7-fluoro-2,3-dihydro-1H-indol-2-one to afford the Example #58 compound. 1H NMR (400 MHz, DMSO-d6): δ 11.65 (s, 1H), 11.25 (s, 1H), 7.67 (s, 1H), 7.40 (s, 1H), 4.75-4.69 (m, 1H), 1.75-1.70 (m, 2H), 1.56 (d, J=4.2 Hz, 2H), 1.45 (d, J=7.1 Hz, 3H).

Preparation of Example #65, 5-(8-bromo-2-oxo-1,2,3,4-tetrahydroquinolin-6-yl)-6-methyl-3,6-dihydro-2H-1,3,4-thiadiazin-2-one, was conducted in a similar fashion to Example #57 but for 8-bromo-3,4-dihydro-quinolone instead of 7-fluoro-2,3-dihydro-1H-indol-2-one to afford the Example #65 compound. 1H NMR (400 MHz, CHLOROFORM-d) δ ppm 8.75 (s, 1H), 7.89 (br s 1H), 7.71 (d, 1H), 7.46 (s, 1H), 4.12 (d, 1H), 2.98 (m, 2H), 2.61 (dd, 2H), 1.59 (d, 3H).

Preparation of Example #67, (6R)-5-(8-chloro-4,4-dimethyl-2-oxo-1,2,3,4-tetrahydroquinolin-6-yl)-6-methyl-3,6-dihydro-2H-1,3,4-thiadiazin-2-one, was conducted in a similar fashion to Example #57 but for 8-chloro-4,4-dimethyl-3,4-dihydroquinolin-2(1H)-one instead of 7-fluoro-2,3-dihydro-1H-indol-2-one to afford the Example #67 compound. 1H NMR (400 MHz, DMSO-d6): δ 11.68 (brs, 1H), 9.81 (brs, 1H), 7.73 (brs, 2H), 4.81 (brs, 1H), 2.47 (s, 2H), 1.45 (d, J=6.4 Hz, 3H), 1.28 (brs, 6H).

Preparation of Example #75, 5-(7-chloro-3,3-dimethyl-2-oxoindolin-5-yl)-6-methyl-3,6-dihydro-2H-1,3,4-thiadiazin-2-one, was conducted in a similar fashion to Example #57 but for 7-chloro-3,3-dimethylindolin-2-one instead of 7-fluoro-2,3-dihydro-1H-indol-2-one to afford the Example #75 compound. 1H NMR (400 MHz, DMSO-d6): δ 11.66 (s, 1H), 11.02 (s, 1H), 7.74 (s, 1H), 7.68 (s, 1H), 4.76-4.73 (m, 1H), 1.47 (d, J=6.8 Hz, 3H), 1.31 (s, 6H).

Preparation of Example #76, 5-(7-bromo-3,3-dimethyl-2-oxoindolin-5-yl)-6-methyl-3,6-dihydro-2H-1,3,4-thiadiazin-2-one, was conducted in a similar fashion to Example #57 but for 7-bromo-3,3-dimethylindolin-2-one instead of 7-fluoro-2,3-dihydro-1H-indol-2-one to afford the Example #76 compound. 1H NMR (400 MHz, DMSO-d6): δ 11.66 (s, 1H), 10.91 (s, 1H), 7.80 (d, J=1.3, 1H), 7.77 (d, J=1.2, 1H), 4.78-4.73 (m, 1H), 1.47 (d, J=7.1 Hz, 3H), 1.30 (s, 6H).

Preparation of Example #61 (5-(7-chloro-3,3-dimethyl-2-oxoindolin-5-yl)-3,6-dihydro-2H-1,3,4-thiadiazin-2-one)

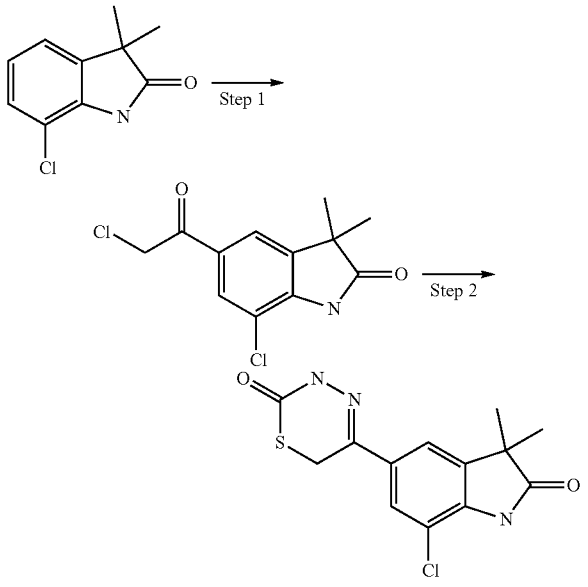

(61)

Step 1. Dimethyl formamide (0.5 mL, 7.66 mmol) was added drop wise to anhydrous aluminum chloride (3.41 g, 25.55 mmol) and stirred at 70° C. for 15 minutes. The resulting mixture was cooled to 40° C. and 7-chloro-3,3-dimethyl-2,3-dihydro-1H-indol-2-one (500 mg, 2.55 mmol) and 2-chloroacetyl chloride (0.26 ml, 3.32 mmol) were slowly added and stirred at 70° C. for 2 hours. After completion, the reaction mixture was diluted with ice water and extracted with ethyl acetate. Combined organic layer was washed with brine, dried over anhydrous sodium sulphate, filtered and concentrated under reduced pressure. Crude product thus obtained was purified by combiflash column chromatography (40-50% EtOAc in hexane) to afford 7-chloro-5-(2-chloroacetyl)-3,3-dimethyl-2,3-dihydro-1H-indol-2-one (300 mg, 43%) as yellow solid. MS (ESI): m/z 269.8 $[M-1]^+$.

Step 2. To a stirred solution of 7-chloro-5-(2-chloroacetyl)-3,3-dimethyl-2,3-dihydro-1H-indol-2-one (300 mg, 1.1 mmol) in acetonitrile (10 mL) was added [(methoxymethane-thioyl)amino]amine (117 mg, 1.1 mmol) and the reaction mixture was stirred at room temperature for 5 minutes. AcOH (0.1 mL) was added and the resulting mixture was heated at 80° C. for 16 hours. The reaction mixture was cooled to room temperature and volatiles were removed under reduce pressure. Crude product thus obtained was purified by combiflash column chromatography (60-70% EtOAc in hexane) to afford the Example #61 compound (120 mg, 35%) as an off-white solid. $^1$H NMR (400 MHz, DMSO-d6): δ 11.56 (s, 1H), 11.03 (s, 1H), 7.74 (s, 1H), 7.70 (s, 1H), 4.21 (s, 2H), 1.30 (s, 6H). LCMS: Retention time=2.48 minutes; HPLC purity=98.56%

Preparation of Example #59, 5-(7-fluoro-3,3-dimethyl-2-oxoindolin-5-yl)-3,6-dihydro-2H-1,3,4-thiadiazin-2-one, was conducted in a similar fashion to Example #61 but for 7-fluoro-3,3-dimethylindolin-2-one instead of 7-chloro-3,3-dimethyl-2,3-dihydro-1H-indol-2-one to afford the Example #59 compound. 1H NMR (400 MHz, DMSO-d6): δ 11.56 (s, 1H), 11.09 (s, 1H), 7.65 (s, 1H), 7.56 (dd, J=0.8 Hz, 11.8 Hz, 1H), 4.20 (s, 2H), 1.30 (s, 6H).

Preparation of Example #66, 5-(7-bromo-3,3-dimethyl-2-oxoindolin-5-yl)-3,6-dihydro-2H-1,3,4-thiadiazin-2-one, was conducted in a similar fashion to Example #61 but for 7-bromo-3,3-dimethylindolin-2-one instead of 7-chloro-3,3-dimethyl-2,3-dihydro-1H-indol-2-one to afford the Example #66 compound. 1H NMR (400 MHz, DMSO-d6): δ 11.57 (s, 1H), 10.91 (s, 1H), 7.82 (s, 1H), 7.77 (s, 1H), 4.21 (s, 2H), 1.30 (s, 6H).

Preparation of Example #72, 5-(2-oxo-2,3,4,5-tetrahydro-1H-benzo[b]azepin-7-yl)-3,6-dihydro-2H-1,3,4-thiadiazin-2-one, was conducted in a similar fashion to Example #61 but for 1,3,4,5-tetrahydro-2H-benzo[b]azepin-2-one instead of 7-chloro-3,3-dimethyl-2,3-dihydro-1H-indol-2-one to afford the Example #72 compound. 1H NMR (400 MHz, DMSO-d6): δ 11.57 (s, 1H), 9.72 (s, 1H), 7.76-7.64 (m, 2H), 7.03 (d, 1H), 4.21 (s, 2H), 2.73 (br t, 2H), 2.16 (br m, 4H).

Preparation of Example #62 (5-(7-chloro-2-oxoindolin-5-yl)-6-methyl-3,6-dihydro-2H-1,3,4-thiadiazin-2-one)

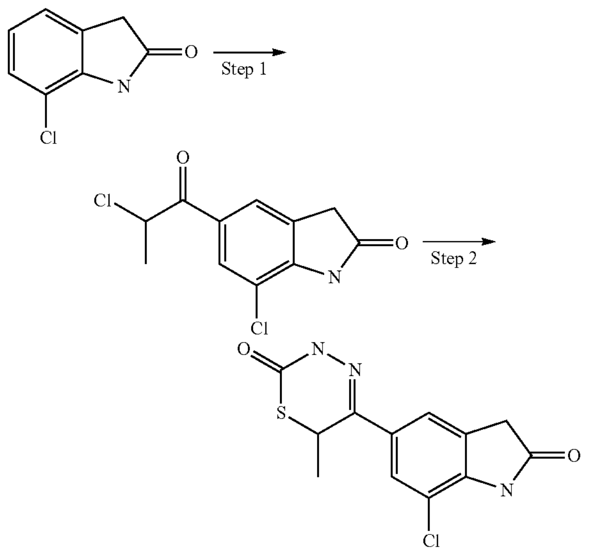

(62)

Step 1. Dimethyl formamide (3.05 mL, 39.52 mmol) was added drop wise to anhydrous aluminum chloride (16 g, 119.76 mmol) and stirred at 70° C. for 15 minutes. The resulting mixture was cooled to 40° C. and 7-chloro-2,3-dihydro-1H-indol-2-one (2 g, 11.97 mmol) and 2-chloropropanoyl chloride (1.3 mL, 15.56 mmol) were slowly added and stirred at 70° C. for 2 hours. After completion, the reaction mixture was diluted with ice water and extracted with ethyl acetate. Combined organic layer was washed with brine, dried over anhydrous sodium sulphate, filtered and concentrated under reduced pressure. Crude product thus obtained was purified by combiflash column chromatography (30-40% EtOAc in hexane) to afford 7-chloro-5-(2-chloropropanoyl)-2,3-dihydro-1H-indol-2-one (900 mg, 29%) as brown solid. MS (ESI): m/z 257.9 [M+1]$^+$.

Step 2. To a stirred solution of 7-chloro-5-(2-chloropropanoyl)-2,3-dihydro-1H-indol-2-one (500 mg, 1.76 mmol) in acetonitrile (10 mL) was added [(methoxymethanethioyl)-amino]amine (186.18 mg, 1.76 mmol) and the resulting mixture was stirred at room temperature for 5 minutes. Acetic acid (0.1 mL) was added and the reaction mixture was heated at 80° C. for 4 hours. After completion, the reaction mixture was diluted with water and extracted with ethyl acetate. Combined organic layer was washed with brine, dried over anhydrous sodium sulphate, filtered and concentrated under reduced pressure. Crude product thus obtained was purified by combiflash column chromatography (50-60% EtOAc in hexane) to afford the Example #62 compound (150 mg, 26%) as a brown solid. $^1$H NMR (400 MHz, DMSO-d6): δ 11.66 (br s, 1H), 11.03 (br s, 1H), 7.68 (s, 1H), 7.65 (s, 1H), 4.75-4.70 (m, 1H), 3.66 (s, 2H), 1.45 (d, J=6.8 Hz, 3H). LCMS: Retention time=2.01 minutes; HPLC purity=98.46%

Preparation of Example #73 (6-methyl-5-(9-methyl-2-oxo-2,3,4,5-tetrahydro-1H-benzo[b]azepin-7-yl)-3,6-dihydro-2H-1,3,4-thiadiazin-2-one)

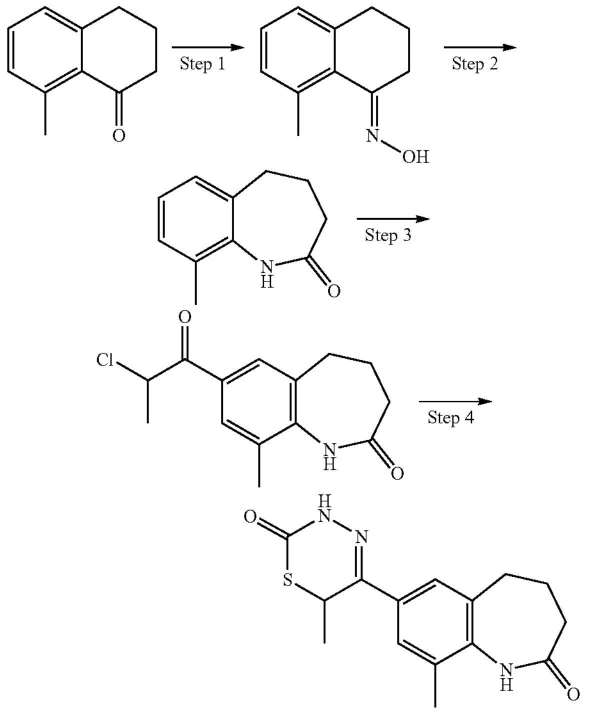

(73)

Step 1. To a stirred solution of 8-methyl-1,2,3,4-tetrahydronaphthalen-1-one (500 mg, 3.12 mmol) in methanol (10 mL) was added hydroxylamine hydrochloride (260 mg, 3.74 mmol) followed by sodium acetate (307 mg, 3.74 mmol) at room temperature under argon atmosphere and resulting mixture was stirred at 60° C. for 4 hours. After completion, the reaction mixture was cooled to ambient temperature and the resulting precipitate was removed by filtration. The filtrate was concentrated under reduced pressure to afford N-[(1E)-8-methyl-1,2,3,4-tetrahydronaphthalen-1-ylidene]-hydroxylamine (460 mg, 84%) as yellow solid. It was used in the next step without further purification. MS (ESI): m/z 176.2 $[M+1]^+$.

Step 2. To a stirred solution of phosphoric acid (1.8 mL) was added phosphorous pentoxide (1.79 g, 6.31 mmol) and the resulting mixture was heated at 100° C. for 0.5 hours. N-[(1E)-8-methyl-1,2,3,4-tetrahydronaphthalen-1-ylidene] hydroxylamine (460 mg, 2.63 mmol) was added and stirred at 100° C. for an additional 2.5 hours. After completion, the reaction mixture was poured into ice-cold water. Solid thus formed was filtered, washed with water and dried under reduce pressure to afford 9-methyl-2,3,4,5-tetrahydro-1H-1-benzazepin-2-one (400 mg, 86%) as a brown solid. MS (ESI): m/z 176.2 $[M+1]^+$.

Step 3. Dimethylformamide (0.58 mL, 7.44 mmol) was added drop-wise to anhydrous aluminum chloride (3.3 g, 24.81 mmol) and stirred at 70° C. for 15 minutes. The resulting mixture was cooled to 40° C. and 9-methyl-2,3,4,5-tetrahydro-1H-1-benzazepin-2-one (400 mg, 2.48 mmol), 2-chloropropanoyl chloride (0.3 mL, 2.98 mmol) were added. The resulting mixture was heated at 70° C. for 2 hours. After completion, the reaction mixture was diluted with ice water and extracted with ethyl acetate. The combined organic layer was washed with brine, dried over anhydrous sodium sulphate, filtered and concentrated under reduced pressure. Crude product thus obtained was purified by combiflash column chromatography (30-40% EtOAc in hexane) to afford 7-(2-chloropropanoyl)-9-methyl-2,3,4,5-tetrahydro-1H-1-benzazepin-2-one (400 mg, 66%) as brown solid. MS (ESI): m/z 266.3 $[M+1]^+$.

Step 4. To a stirred solution of 7-(2-chloropropanoyl)-9-methyl-2,3,4,5-tetrahydro-1H-1-benzazepin-2-one (250 mg, 0.94 mmol) in acetonitrile (5 mL) was added [(ethoxymethanethioyl)amino]amine (100 mg, 0.94 mmol) and stirred at room temperature for 5 minutes. AcOH (0.1 mL) was added and the resulting mixture was heated at 80° C. for 16 hours. The reaction mixture was cooled to room temperature and volatiles were removed under reduced pressure. Crude product thus obtained was purified by combiflash column chromatography (40-60% EtOAc in hexane) to afford the Example #73 compound (60 mg, 21%) as an off white solid. 1H NMR (400 MHz, DMSO-d6): δ 11.64 (s, 1H), 9.24 (s, 1H), 7.56 (s, 2H), 4.74-4.69 (m, 1H), 2.71-2.67 (m, 2H), 2.27 (s, 3H), 2.15-2.05 (m, 4H), 1.48 (d, J=6.8 Hz, 3H). LCMS: Retention time=2.47 minutes; HPLC purity=96.28%.

Preparation of Example #77 (5-(6-methyl-2-oxo-3,6-dihydro-2H-1,3,4-thiadiazin-5-yl)-2-oxoindoline-7-carbonitrile)

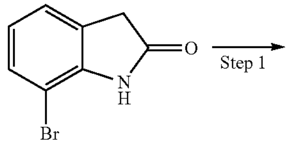

-continued

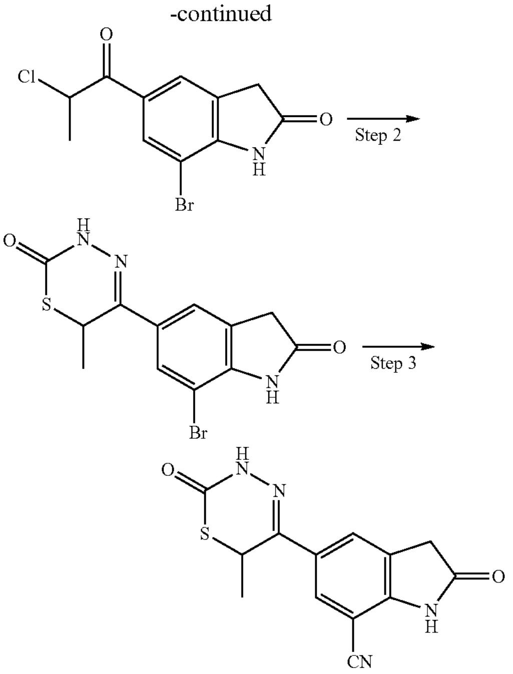

(77)

Step 1. A slurry of anhydrous $AlCl_3$ (31.4 g, 235.8 mmol) and DMF (5.4 mL, 70.7 mmol) was heated at 70° C. for 15 minutes then cooled to 40° C. 7-bromoindolin-2-one (5.0 g, 23.58 mmol) and 2-chloropropanoyl chloride (2.7 mL, 28.30 mmol) were slowly added. Resulting mixture was heated at 70° C. for 4 hours. Reaction mixture was cooled to ambient temperature, poured into crushed ice and extracted with ethyl acetate. Combined organic layer was washed with brine, dried over anhydrous sodium sulphate, filtered and concentrated under reduced pressure. Crude product was purified by combi flash column chromatography (40-60% EtOAc in hexane) to afford 7-bromo-5-(2-chloropropanoyl) indolin-2-one (4.1 g, 48%) as brown solid. MS (ESI): m/z 302.0 [M+1]+.

Step 2. To a stirred solution of 7-bromo-5-(2-chloropropanoyl)indolin-2-one (1.0 g, 3.63 mmol) in acetonitrile (10.0 mL) were added acetic acid (2.0 mL) and O-methyl hydrazine-carbothioate (0.39 g, 3.64 mmol) at room temperature. Resulting reaction mixture was heated at 90° C. for 16 hours. After completion, reaction mixture concentrated under reduced pressure. Crude product was purified by combi flash column chromatography (60-70% EtOAc in hexane) to afford 5-(7-bromo-2-oxoindolin-5-yl)-6-methyl-3,6-dihydro-2H-1,3,4-thiadiazin-2-one (1.1 g, 24%) as off-white solid. MS (ESI): m/z 340.05 [M+1]+.

Step 3. To a stirred solution of 5-(7-bromo-2-oxoindolin-5-yl)-6-methyl-3,6-dihydro-2H-1,3,4-thiadiazin-2-one (150 mg, 0.44 mmol) in DMF (4.0 mL), was added zinc cyanide (62.3 mg, 0.53 mmol) at room temperature. Reaction mixture was de-gassed for 5 minutes followed by addition of $Pd_2(dba)_3$ (12.19 mg, 0.013 mmol) and dppf (2.46 mg, 0.004 mmol). Resulting mixture was heated under microwave (MW) for 0.5 hours at 140° C. After completion reaction mixture was diluted with cold water and extracted with DCM. Combined organic layer was washed with brine, dried over anhydrous sodium sulphate, filtered and concentrated under reduced pressure. Crude mass was purified by normal phase prep-HPLC to afford the Example #77 compound (65 mg, 36%) as an off-white solid. 1H NMR (400 MHz, DMSO-d6): δ 11.73 (s, 1H), 11.58 (bs, 1H), 7.97 (s, 1H), 7.95 (s, 1H), 4.76 (q, J=8.3 Hz, 1H), 3.64 (s, 2H), 1.46 (d, J=7.1 Hz, 3H).

Preparation of Example #79 (7-chloro-5-(6-methyl-2-oxo-3,6-dihydro-2H-1,3,4-thiadiazin-5-yl)-2,3-dihydro-1H-isoindol-1-one)

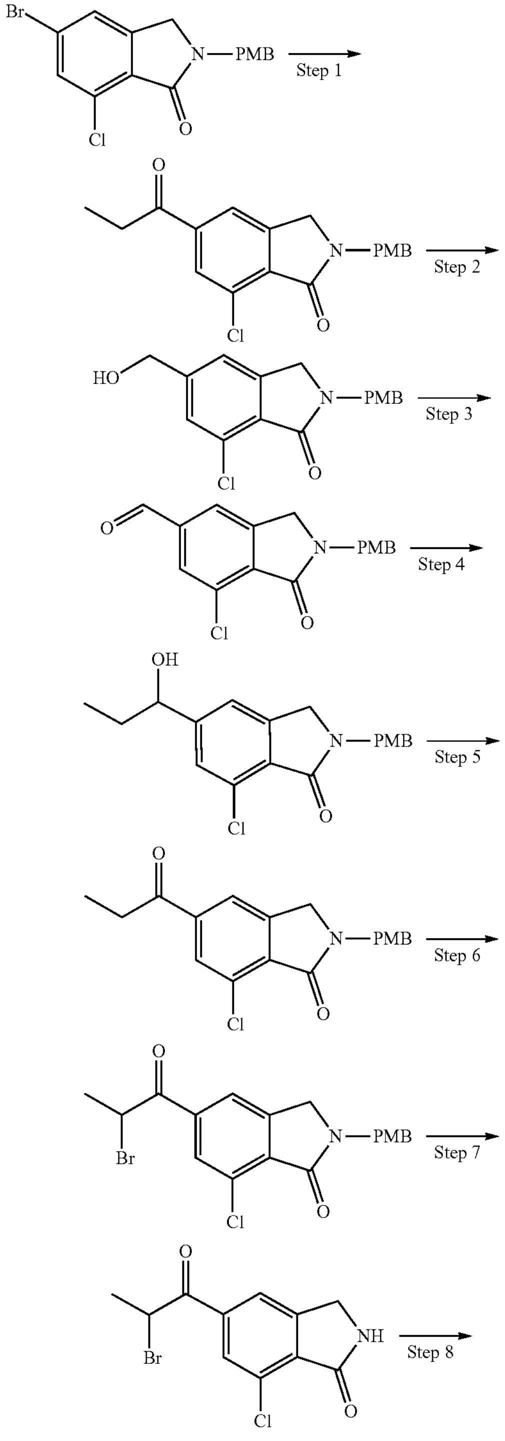

-continued

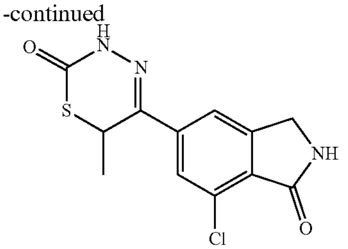

(79)

Step 1. To a stirred solution of 5-bromo-7-chloro-2-(4-methoxybenzyl)isoindolin-1-one (7.5 g, 20.5 mmol) in MeOH (150 mL) was added DIPEA (18 ml, 101.1 mmol) followed by Pd(dppf)$Cl_2$·DCM (1.6 g, 2.18 mmol) and resulting mixture was purged with argon for 10 minutes and was heated at 90° C. for 16 hours. After completion, reaction mixture was diluted with water and extracted with ethyl acetate. Combined organic layer was washed with brine, dried over anhydrous sodium sulphate, filtered and concentrated under reduced pressure. Crude product thus obtained was purified by combi flash column chromatography (10-20% EtOAc in hexane) to afford 7-chloro-2-(4-methoxybenzyl)-5-propionylisoindolin-1-one (3.2 g, 45%) as white solid. MS (ESI): m/z 344 $[M+1]^+$.

Step 2. To a stirred solution of 7-chloro-2-(4-methoxybenzyl)-5-propionylisoindolin-1-one (1 g, 2.89 mmol) in THF-EtOH (15 mL; 2:1 ratio) was added $LiBH_4$ (158 mg, 7.22 mmol) and allowed to stir at RT for 16 hours. After completion, reaction mixture was diluted with water and extracted with ethyl acetate. Combined organic layer was washed with brine, dried over anhydrous sodium sulphate, filtered and concentrated under reduced pressure. Crude product was purified by combi flash column chromatography (30-40% EtOAc in hexane) to afford 7-chloro-5-(hydroxymethyl)-2-(4-methoxybenzyl)isoindolin-1-one (500 mg, 54%) as off-white solid. MS (ESI): m/z 318 [M+1]+.

Step 3. To a stirred solution of 7-chloro-5-(hydroxymethyl)-2-(4-methoxybenzyl)isoindolin-1-one (1.5 g, 4.7 mmol) in DCM (25 mL) was added Dess martin periodinane (3.9 g, 9.4 mmol) at 0° C. and stirred at RT for 16 hours. Reaction mixture was filtered through a short pad of celite and washed with ethyl acetate. Combined filtrate part was concentrated under reduced pressure and purified by combiflash column chromatography (20-30% ethyl acetate in hexane) to afford 7-chloro-2-(4-methoxybenzyl)-1-oxoisoindoline-5-carbaldehyde (1.0 g, 67%) as off-white solid. MS (ESI): m/z 316 [M+1]+.

Step 4. To a stirred solution of 7-chloro-2-(4-methoxybenzyl)-1-oxoisoindoline-5-carbaldehyde (700 mg, 2.2 mmol) in THE (10 mL) was added EtMgBr (4.4 ml, 8.9 mmol, 2M in THF) under ice-cold condition and allowed to stir at RT for 6 hours. After completion, reaction mixture was diluted with water and extracted with ethyl acetate. Combined organic layer was washed with brine, dried over anhydrous sodium sulphate, filtered and concentrated under reduced pressure. Crude product was purified by combi flash column chromatography (30-40% ethyl acetate in hexane) to afford 7-chloro-5-(1-hydroxypropyl)-2-(4-methoxybenzyl) isoindolin-1-one (320 mg, 41%) as off-white solid. MS (ESI): m/z 346 [M+1]+.

Step 5. To a stirred solution of 7-chloro-5-(1-hydroxypropyl)-2-(4-methoxybenzyl)isoindolin-1-one (550 mg, 1.5 mmol) in DCM (15 mL) was added Dess martin periodinane (1.3 g, 3.18 mmol) at 0° C. and stirred at RT for 16 hours.

Reaction mixture was filtered through a short pad of celite and washed with ethyl acetate. Combined filtrate part was concentrated under reduced pressure and purified by combiflash column chromatography (20-30% ethyl acetate in hexane) to afford 7-chloro-2-(4-methoxybenzyl)-5-propionylisoindolin-1-one (400 mg, 73%) as off-white solid. MS (ESI): m/z 344 [M+1]+.

Step 6. To a stirred solution of 7-chloro-2-(4-methoxybenzyl)-5-propionylisoindolin-1-one (420 mg, 1.22 mmol) in THE (10 mL) was added NBS (872 mg, 4.89 mmol) portion wise at RT and stirred for 16 hours. After completion, reaction mixture was diluted with water and extracted with ethyl acetate. Combined organic layer was washed with brine, dried over anhydrous sodium sulphate, filtered and concentrated under reduced pressure. Crude product was purified by combi flash column chromatography (50-60% ethyl acetate in hexane) to afford 5-(2-bromopropanoyl)-7-chloro-2-(4-methoxybenzyl)isoindolin-1-one [contaminated with di-bromo substituted compound] (280 mg, 54%) as white solid. MS (ESI): m/z 423 [M+1]+.

Step 7. A stirred solution of 5-(2-bromopropanoyl)-7-chloro-2-(4-methoxybenzyl)isoindolin-1-one (300 mg, 0.71 mmol) in TFA (5 mL) was heated at 80° C. for 16 hours. After completion, volatiles were removed under reduce pressure the residue was diluted with water and extracted with dichloromethane. Combined organic layer was washed with brine, dried over anhydrous sodium sulphate, filtered and concentrated under reduced pressure. Crude product was purified by combiflash chromatography (70-90% EtOAc in hexane) to afford 5-(2-bromopropanoyl)-7-chloroisoindolin-1-one (135 mg, 63%) as off-white solid. MS (ESI): m/z 303 [M+1]+.

Step 8. To a stirred solution of 5-(2-bromopropanoyl)-7-chloroisoindolin-1-one (150 mg, 0.49 mmol) in EtOH (15 ml) was added O-methyl hydrazinecarbothioate (63 mg, 0.59 mmol) and heated to reflux at 90° C. for 16 hours. After completion, volatiles were removed under reduce pressure and the residue was diluted with water and extracted with ethyl acetate. Combined organic layer was washed with brine, dried over anhydrous sodium sulphate, filtered and concentrated under reduced pressure. Crude product was purified by combiflash column chromatography (70-90% EtOAc in hexane) to afford the Example #79 compound (20.5 mg) as off-white solid (98.22% purity). 1H NMR (400 MHz, DMSO-d6): δ 11.90 (s, 1H), 8.79 (s, 1H), 7.95 (s, 1H), 7.84 (s, 1H), 4.84-4.79 (m, 1H), 4.39 (s, 2H), 1.49 (d, J=7.2 Hz, 3H).

Preparation of Example #80 (7-chloro-3,3-dimethyl-5-(6-methyl-2-oxo-3,6-dihydro-2H-1,3,4-thiadiazin-5-yl)-2,3-dihydro-1H-isoindol-1-one)

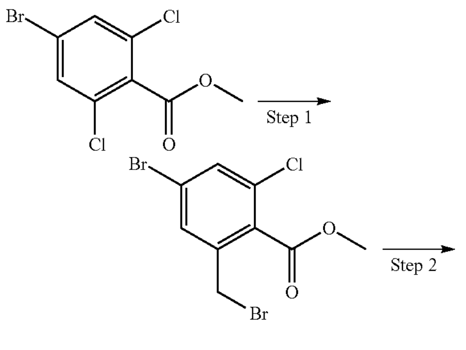

-continued

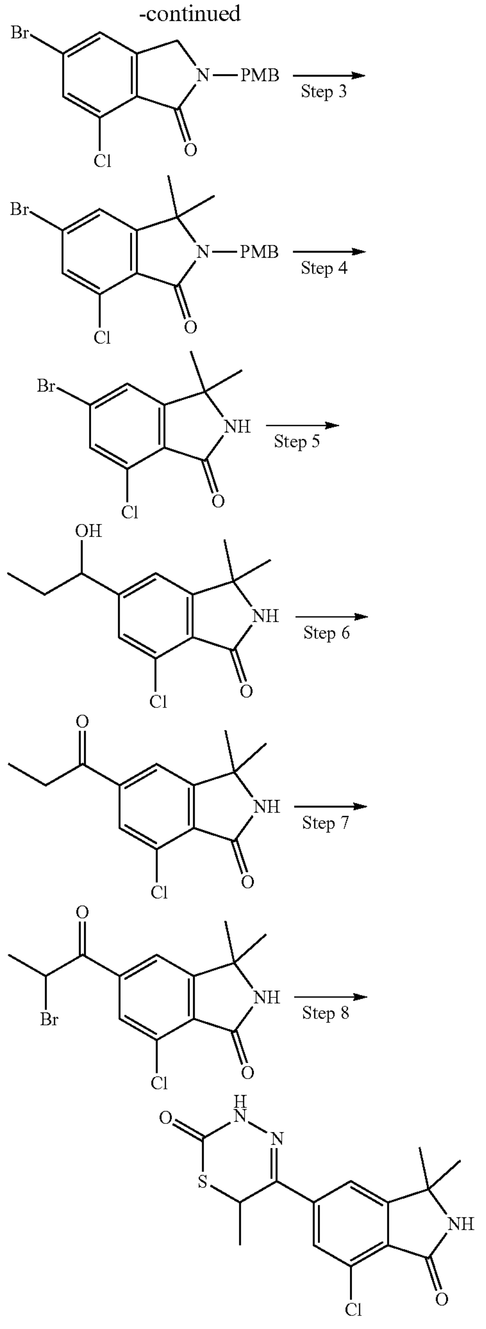

(80)

Step 1. To a stirred solution of methyl 4-bromo-2-chloro-6-methylbenzoate (5 g, 19.09 mmol) and benzoyl peroxide (0.63 g, 3.82 mmol) in carbon tetrachloride (20 mL) was added NBS (4 g, 22.91 mmol) portion wise at room temperature and resulting mixture was refluxed for 16 hours. After completion, volatiles were removed under reduced pressure. Crude product was triturated with pentane-hexane (1:1) to get desired product methyl 4-bromo-2-(bromomethyl)-6-chlorobenzoate (5 g, crude) as brownish solid which was carried to the next step without further purification. MS (ESI): m/z 340 $[M+1]^+$.

Step 2. To a stirred solution of methyl 4-bromo-2-(bromomethyl)-6-chlorobenzoate (5 g, 14.70 mmol) and TEA (6.1 ml, 43.76 mmol) in DMF (50 mL) was added 4-methoxy benzyl amine (3.8 mL, 29.4 mmol) and was allowed to stir at RT for 5 hours. After completion, reaction mixture was diluted with water and extracted with ethyl acetate. Combined organic layer was washed with brine, dried over anhydrous sodium sulphate, filtered and concentrated under reduced pressure. Crude product was purified by combiflash column chromatography (20-30% EtOAc in hexane) to afford 5-bromo-7-chloro-2-(4-methoxybenzyl) isoindolin-1-one (3.3 g, 61% in two steps) as off-white solid. MS (ESI): m/z 366 $[M+1]^+$.

Step 3. To a stirred solution of 5-bromo-7-chloro-2-(4-methoxybenzyl)isoindolin-1-one (1.5 g, 4.11 mmol) in THF, NaH (493 mg, 12.32 mmol, 60% in mineral oil) was added at 0° C. under argon atmosphere and resulting mixture was allowed to stir at RT for 30 minutes. Methyl iodide (1.0 ml, 16 mmol) was added and resulting mixture was heated at 70° C. for 3 hours. After completion, reaction mixture was quenched with aqueous ammonium chloride solution and extracted with ethyl acetate. Combined organic layer was washed with brine, dried over anhydrous sodium sulphate, filtered and concentrated under reduce pressure. Crude product thus obtained was purified by combiflash column chromatography (10-20% ethyl acetate in hexane) to afford 5-bromo-7-chloro-2-(4-methoxybenzyl)-3,3-dimethylisoindolin-1-one (900 mg, 56%) as white solid. MS (ESI): m/z 394 $[M+1]^+$.

Step 4. A stirred solution of 5-bromo-7-chloro-2-(4-methoxybenzyl)-3,3-dimethylisoindolin-1-one (500 mg, 1.27 mmol) in TFA (10 mL) was heated at 80° C. for 16 hours. After completion, volatiles were removed under reduce pressure the residue was diluted with water and extracted with dichloromethane. Combined organic layer was washed with brine, dried over anhydrous sodium sulphate, filtered and concentrated under reduced pressure. Crude product was purified by combiflash chromatography (70-90% ethyl acetate in hexane) to afford 5-bromo-7-chloro-3,3-dimethyl-2,3-dihydro-1H-isoindol-1-one (230 mg, 66%) as off-white solid. MS (ESI): m/z 274 $[M+1]^+$.

Step 5. To a stirred of nBuLi (1.5 mL, 0.75 mmol, 2M in THF) in THF (5 mL) was added iPrMgCl·LiCl (0.7 mL, 0.91 mmol, 1.3M in THF) at −78° C. under argon atmosphere. A solution of 5-bromo-7-chloro-3,3-dimethyl-2,3-dihydro-1H-isoindol-1-one (200 mg, 0.735 mmol) in THF (10 mL) was added to the reaction mixture and resulting mixture was warmed to RT while stirred for 1 hour. Reaction mixture was cooled to −78° C. and propionaldehyde (0.32 ml, 4.41 mmol) was added and stirred at −78° C. for 2 hours. After completion, reaction mixture was quenched with aqueous ammonium chloride solution and extracted with ethyl acetate. Combined organic layer was washed with brine, dried over anhydrous sodium sulphate, filtered and concentrated under reduce pressure. Crude product was purified by combiflash column chromatography (40-60% EtOAc in hexane) to afford 7-chloro-5-(1-hydroxypropyl)-3,3-dimethyl-2,3-dihydro-1H-isoindol-1-one (80 mg, 43%) as white solid. MS (ESI): m/z 254 [M+1]+.

Step 6. To a stirred solution of 7-chloro-5-(1-hydroxypropyl)-3,3-dimethyl-2,3-dihydro-1H-isoindol-1-one (460 mg, 1.82 mmol) in DCM (10 mL) was added Dess martin periodinane (1.54 g, 3.63 mmol) at 0° C. and stirred at RT for 16 hours. The reaction mixture was filtered through a short pad of celite and washed with ethyl acetate. The combined filtrate part was concentrated under reduced pressure and purified by combiflash column chromatography (50-60% EtOAc in hexane) to afford 7-chloro-3,3-dimethyl-5-propanoyl-2,3-dihydro-1H-isoindol-1-one (325 mg, 72%) as white solid. MS (ESI): m/z 252 [M+1]+.

Step 7. To a stirred solution of 5-(2-bromopropanoyl)-7-chloro-3,3-dimethyl-2,3-dihydro-1H-isoindol-1-one (150 mg, 0.60 mmol) in THF (5 mL) was added NBS (266 mg, 1.45 mmol) portion wise at RT and resulting mixture was stirred at RT for 16 hours. Reaction mixture was poured into ice-water and extracted with ethyl acetate. Combined organic layer was washed with brine, dried over anhydrous sodium sulphate, filtered and concentrated under reduce pressure. Crude product was purified by combiflash column chromatography (40-60% ethyl acetate in hexane) to afford 5-(2-bromopropanoyl)-7-chloro-3,3-dimethyl-2,3-dihydro-1H-isoindol-1-one (100 mg, 50%) as white solid. MS (ESI): m/z 330 [M+1]+.

Step 8. To a stirred solution of 5-(2-bromopropanoyl)-7-chloro-3,3-dimethyl-2,3-dihydro-1H-isoindol-1-one (250 mg, 0.76 mmol) in EtOH (10 ml) was added O-methyl hydrazinecarbothioate (97 mg, 0.912 mmol) and heated to reflux at 90° C. for 16 hours. After completion, volatiles were removed under reduce pressure and the residue was diluted with water and extracted with ethyl acetate. Combined organic layer was washed with brine, dried over anhydrous sodium sulphate, filtered and concentrated under reduced pressure. Crude product was purified by PREP-HPLC to afford the Example #80 compound (35 mg, 15%) as an off-white solid (97.59% purity). $^1H$ NMR (400 MHz, DMSO-d6): δ 11.90 (s, 1H), 8.88 (s, 1H), 7.99 (s, 1H), 7.81 (s, 1H), 4.87-4.82 (m, 1H), 1.50-1.46 (m, 9H).

Preparation of Example #84 (4-chloro-6-(2-oxo-2,3-dihydro-1H-pyrrolo[2,3-b]pyridin-5-yl)benzo[d]oxazol-2 (3H)-one)

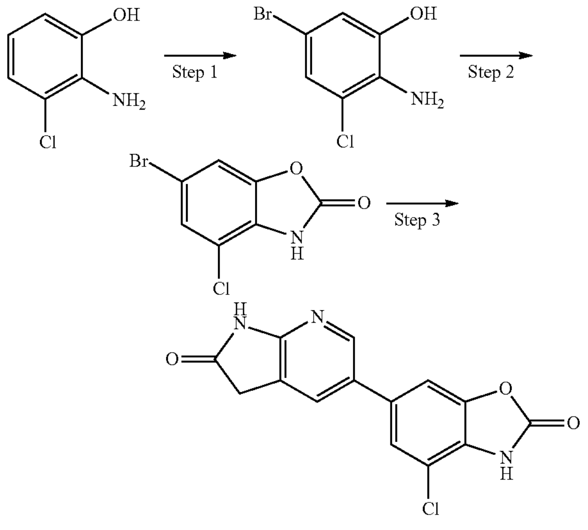

(84)

Step 1. To a stirred solution of 2-amino-3-chlorophenol (2 g, 13.97 mmol) in DCM (100 mL) was added bromine (1.08 mL, 20.98 mmol) drop wise at 0° C. and the resulting mixture was stirred at room temperature for 16 hours. Solid thus formed was filtered, washed with DCM and dried. Solid residue was partitioned between aqueous saturated $NaHCO_3$ solution and DCM. Organic layer was washed with water, brine and was dried over anhydrous sodium sulphate, filtered and concentrated to afford 2-amino-5-bromo-3-chlorophenol (1.3 g, 41%) as brown powder. MS (ESI): m/z 221.6 $[M-1]^+$.

Step 2. To a stirred solution of 2-amino-5-bromo-3-chlorophenol (1.3 g, 5.88 mmol) in THE (20 mL) was added CDI (4.58 g, 28.24 mmol) and the resulting mixture was heated at 65° C. for 2 hours. After completion, reaction mixture was diluted with water and extracted with ethyl acetate. Combined organic layer was washed with brine, dried over anhydrous sodium sulphate, filtered and concentrated under reduced pressure to afford 6-bromo-4-chloro-2,3-dihydro-1,3-benzoxazol-2-one (800 mg, 54%) as brown powder. MS (ESI): m/z 246.0 $[M-1]^+$.

Step 3. To a stirred solution 6-bromo-4-chloro-2,3-dihydro-1,3-benzoxazol-2-one (200 mg, 0.81 mmol) in 1,4-dioxane (4 mL) and water (1 mL) in a microwave vessel was added 5-(tetramethyl-1,3,2-dioxaborolan-2-yl)-1H,2H,3H-pyrrolo[2,3-b]pyridin-2-one (316 mg, 1.22 mmol) followed by $K_3PO_4$ (430 mg, 2.02 mmol) and the resulting mixture was purged with argon for 10 minutes. Pd(dtbpf)$Cl_2$ (53 mg, 0.08 mmol) was added and the reaction mixture was heated under microwave irradiation at 100° C. for 1 hour. After completion, the reaction mixture was diluted with water and extracted with 10% MeOH in DCM. Combined organic layer was washed with brine, dried over anhydrous sodium sulphate, filtered and concentrated under reduced pressure. Crude product thus obtained was purified by reverse phase prep HPLC to afford the Example #84 compound (30 mg, 12%) as an off white solid. 1H NMR (400 MHz, DMSO-d6): δ 12.35 (br s, 1H), 11.10 (s, 1H), 8.38 (s, 1H), 7.90 (s, 1H), 7.62 (s, 1H), 7.53 (s, 1H), 3.60 (s, 2H). LCMS: Retention time=1.85 minutes; HPLC purity=93.25%

Preparation of Example #85 (5-(7-chloro-3,3-dimethyl-2-oxoindolin-5-yl)-1,3-dihydro-2H-pyrrolo[2,3-b]pyridin-2-one)

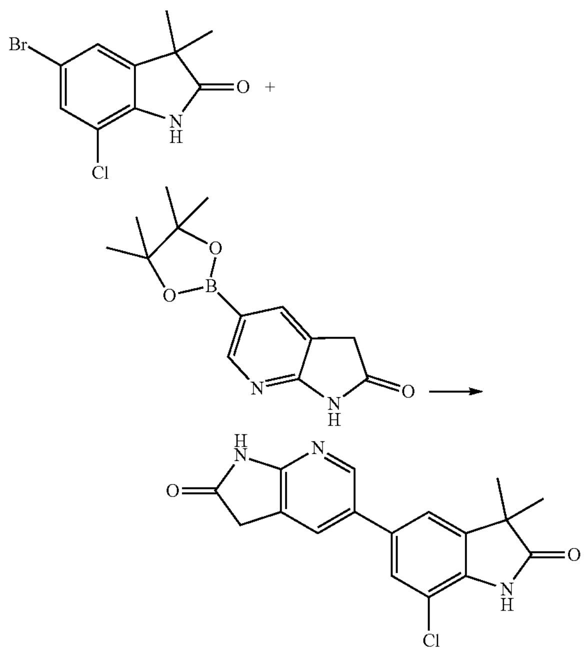

(85)

Refer to Steps 1-2 of Example #87 for the preparation of 5-bromo-7-chloro-3,3-dimethyl-2,3-dihydro-1H-indol-2-one. Then to a stirred solution of 5-bromo-7-chloro-3,3-dimethyl-2,3-dihydro-1H-indol-2-one (150 mg, 0.55 mmol) in dioxane (4 mL) and water (1 mL) was added 5-(4,4,5,5-tetramethyl-1,3,2-dioxaborolan-2-yl)-1,3-dihydro-2H-pyrrolo[2,3-b]pyridin-2-one (214 mg, 0.82 mmol) followed by $K_3PO_4$ (292 mg, 1.37 mmol) and the resulting mixture was purged with argon for 10 minutes. Pd(dtbpf)$Cl_2$ (36 mg, 0.5 mmol) was added and the reaction mixture was heated under microwave irradiation at 100° C. for 1 hour. After completion, reaction mixture was diluted with water and extracted with ethyl acetate. Combined organic layer was washed with brine, dried over anhydrous sodium sulphate, filtered and concentrated under reduced pressure. Crude product thus obtained was purified by column chromatography (3-10% MeOH in DCM) to afford the Example #85 compound (50 mg, 28%) as an off white solid. 1H NMR (400 MHz, DMSO-d6): δ 11.06 (s, 1H), 10.84 (s, 1H), 8.37 (s, 1H), 7.89 (s, 1H), 7.64 (s, 1H), 7.53 (s, 1H), 3.60 (s, 2H), 1.32 (s, 6H). LCMS: Retention time=2.42 minutes; HPLC purity=96.99%

Preparation of Example #86, 7-chloro-3,3-dimethyl-5-(pyrimidin-5-yl)indolin-2-one, was conducted in a similar fashion to Example #85, but for pyrimidine-5-boronic acid instead of 5-(4,4,5,5-tetramethyl-1,3,2-dioxaborolan-2-yl)-1,3-dihydro-2H-pyrrolo[2,3-b]pyridin-2-one to afford the Example #86 compound. 1H NMR (400 MHz, DMSO-d6) δ: 10.97 (br-s, 1H), 9.18-9.14 (m, 3H), 7.84 (m, 1H), 7.78 (m, 1H), 1.34 (s, 6H).

Preparation of Example #87 (6-(7-chloro-3,3-dimethyl-2-oxoindolin-5-yl)-3,4-dihydro-1,8-naphthyridin-2(1H)-one)

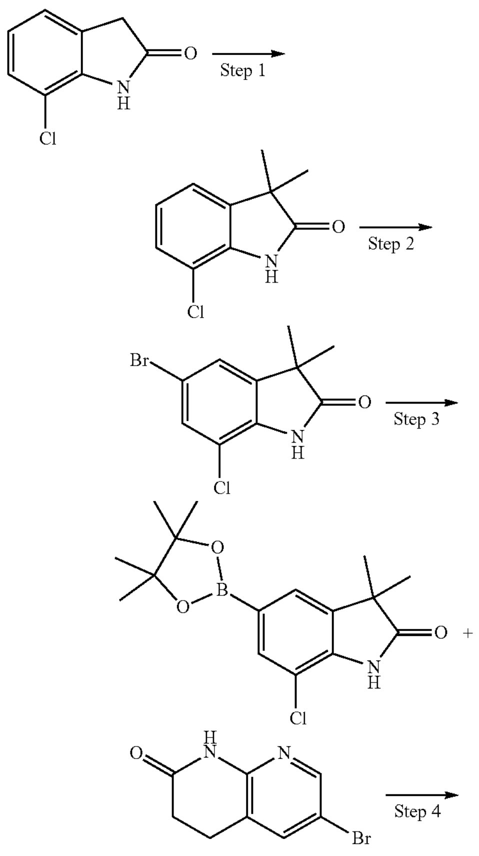

-continued

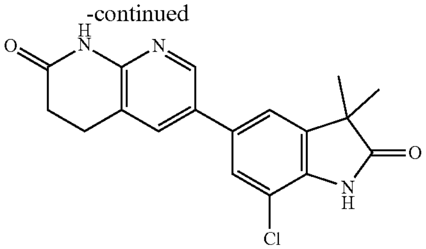

(87)

Step 1. To a stirred solution of 7-chloro-2,3-dihydro-1H-indol-2-one (5 g, 29.83 mmol) in dry THE (50 mL) was added lithium chloride (3.79 g, 89.50 mmol) and the resulting mixture was cooled to −78° C. Lithium diisopropylamide (29.8 mL, 59.67 mmol, 2.0 M in THF/heptane/ethylbenzene) was added and stirred at −78° C. for 15 minutes. Methyl iodide (3.76 mL, 59.67 mmol) was added and the reaction mixture was stirred at room temperature for 5 hours. After completion, the reaction mixture was quenched with aqueous ammonium chloride solution and extracted with ethyl acetate. Combined organic layer was washed with brine, dried over anhydrous sodium sulphate, filtered and concentrated under reduce pressure. Crude product thus obtained was purified by column chromatography (10-20% EtOAc in hexane) to afford 7-chloro-3,3-dimethyl-2,3-dihydro-1H-indol-2-one (2.8 g, 48%) as yellow solid. MS (ESI): m/z 196.2 $[M+1]^+$.

Step 2. To a stirred solution of 7-chloro-3,3-dimethyl-2,3-dihydro-1H-indol-2-one (1.5 g, 7.65 mmol) in trifluoroacetic acid (15 mL) was added N-bromo succinimide (892 mg, 9.18 mmol) portion wise and reaction mixture was stirred at room temperature for 16 hours. After completion, trifluoroacetic acid was evaporated under reduce pressure. The residue was diluted with ethyl acetate, water and layers were separated. Organic layer was dried over anhydrous sodium sulphate, filtered, concentrated under reduced pressure. Crude product thus obtained was purified by combiflash column chromatography (10-20% EtOAc in hexane) to afford 5-bromo-7-chloro-3,3-dimethyl-2,3-dihydro-1H-indol-2-one (800 mg, 38%) as yellow solid. MS (ESI): m/z 274.1 & 276.1 $[M+1]^+$.

Step 3. To a stirred solution of 5-bromo-7-chloro-3,3-dimethyl-2,3-dihydro-1H-indol-2-one (500 mg, 1.83 mmol) in dioxane (5 mL) was added bis(pinacolato)diboron (558 mg, 2.2 mmol) followed by KOAc (360 mg, 3.66 mmol) and the resulting mixture was purged with argon for 10 minutes. Pd(dppf)Cl2·dcm (150 mg, 0.183 mmol) was added and the reaction mixture was heated at 95° C. for 16 hours. After completion, the reaction mixture was diluted with water and extracted with ethyl acetate. Combined organic layer was washed with brine, dried over anhydrous sodium sulphate, filtered and concentrated under reduced pressure. Crude product thus obtained was purified by combiflash column chromatography (30-40% EtOAc in hexane) to afford 7-chloro-3,3-dimethyl-5-(tetramethyl-1,3,2-dioxaborolan-2-yl)-2,3-dihydro-1H-indol-2-one (300 mg, 51%) as brown solid. MS (ESI): m/z 322.2 [M+1]+.

Step 4. To a stirred solution of 7-chloro-3,3-dimethyl-5-(tetramethyl-1,3,2-dioxaborolan-2-yl)-2,3-dihydro-1H-indol-2-one (100 mg, 0.3 mmol) in dioxane (4 mL) and water (1 mL) was added 6-bromo-3,4-dihydro-1H-1,8-naphthyridin-2-one (106 mg, 0.46 mmol) followed by $K_3PO_4$ (360 mg, 3.66 mmol) and the resulting mixture was purged with argon for 10 minutes. Pd(dtbpf)$Cl_2$ (150 mg, 0.183 mmol) was added and the reaction mixture was heated under microwave irradiation at 100° C. for 1 hour. After completion, the reaction mixture was diluted with water and extracted with ethyl acetate. Combined organic layer was washed with brine, dried over anhydrous sodium sulphate, filtered and concentrated under reduced pressure. Crude product thus obtained was purified by reverse phase prep HPLC to afford the Example #87 compound (40 mg, 38%) as an off white solid. 1H NMR (400 MHz, DMSO-d6): δ 10.86 (s, 1H), 10.54 (s, 1H), 8.43 (s, 1H), 7.94 (s, 1H), 7.67 (s, 1H), 7.58 (s, 1H), 2.96-2.92 (m, 2H), 2.57-2.54 (m, 2H), 1.33 (s, 6H). LCMS: Retention time=2.12 minutes; HPLC purity=99.16%.

Preparation of Example #25, 7-chloro-3,3-dimethyl-5-(6-oxo-1,6-dihydropyridazin-3-yl)indolin-2-one, was conducted in a similar fashion to Example #87 but for 6-bromopyridazin-3(2H)-one instead of 6-bromo-3,4-dihydro-1H-1,8-naphthyridin-2-one to afford the Example #25 compound. 1H NMR (400 MHz, DMSO-d6): δ 8.06 (d, 1H), 7.80 (s, 1H), 7.75 (s, 1H), 6.98 (d, 1H), 1.32 (s, 1H).

The Example number, compound names (mass ([M+1]+)) and respective chemical structures are described below.

Example # and Name (Mass)

#1. 8-(2-methoxypyridin-4-yl)-6-(4-methyl-6-oxo-1,4,5,6-tetrahydropyridazin-3-yl)-3,4-dihydroquinolin-2(1H)-one (364);

#2. 6-(4-methyl-6-oxo-1,4,5,6-tetrahydropyridazin-3-yl)-8-(thiazol-2-yl)-3,4-dihydroquinolin-2(1H)-one (340);

#3. 8-bromo-6-(4-methyl-6-oxo-1,4,5,6-tetrahydropyridazin-3-yl)-3,4-dihydroquinolin-2(1H)-one (336);

#4. 8-(2-methoxythiazol-5-yl)-6-(4-methyl-6-oxo-1,4,5,6-tetrahydropyridazin-3-yl)-3,4-dihydroquinolin-2(1H)-one (370);

#5. 5-methyl-6-(1-methyl-2-((4-(methylsulfonyl)phenyl)amino)-1H-benzo[d]imidazol-6-yl)-4,5-dihydropyridazin-3(2H)-one (412);

#6. 7-chloro-5-(4-methyl-6-oxo-1,4,5,6-tetrahydropyridazin-3-yl)indolin-2-one (278);

#7. 7-(4-chlorophenyl)-5-(6-oxo-1,6-dihydropyridazin-3-yl)indolin-2-one (337);

#8. 7'-chloro-5'-(4-methyl-6-oxo-1,4,5,6-tetrahydropyridazin-3-yl)spiro[cyclopropane-1,3'-indolin]-2'-one (304);

#9. 8-(4-chlorophenyl)-6-(6-oxo-1,6-dihydropyridazin-3-yl)-3,4-dihydroquinolin-2(1H)-one (351);

#10. 6-(2-(benzo[d]thiazol-6-ylamino)-1-methyl-1H-benzo[d]imidazol-6-yl)-5-methyl-4,5-dihydropyridazin-3(2H)-one (390);

#11. 8-bromo-4,4-dimethyl-6-(4-methyl-6-oxo-1,4,5,6-tetrahydropyridazin-3-yl)-3,4-dihydroquinolin-2(1H)-one (364);

#12. 8-(3-fluorophenyl)-6-(4-methyl-6-oxo-1,4,5,6-tetrahydropyridazin-3-yl)-3,4-dihydroquinolin-2(1H)-one (352);

#13. 6-(4-methyl-6-oxo-1,4,5,6-tetrahydropyridazin-3-yl)-8-(pyridin-3-yl)-3,4-dihydroquinolin-2(1H)-one (334);

#14. 8-(6-methoxypyridin-3-yl)-6-(4-methyl-6-oxo-1,4,5,6-tetrahydropyridazin-3-yl)-3,4-dihydroquinolin-2(1H)-one (364);

#15. 4-methyl-6-(6-oxo-1,4,5,6-tetrahydropyridazin-3-yl)benzo[d]thiazol-2 (3H)-one (261);

#16. 6-(1-cyclopropyl-2-((4-(methylsulfonyl)phenyl)amino)-1H-benzo[d]imidazol-6-yl)-5-methyl-4,5-dihydropyridazin-3(2H)-one (438);

#17. 3,3-dimethyl-5-(4-methyl-6-oxo-1,6-dihydropyridazin-3-yl)-7-(thiazol-4-yl)indolin-2-one (352);

#18. 9-(6-methoxypyridin-3-yl)-7-(4-methyl-6-oxo-1,4,5,6-tetrahydropyridazin-3-yl)-1,3,4,5-tetrahydro-2H-benzo[b]azepin-2-one (378);

#19. 6-(2-(1-(4-methoxyphenyl)cyclopropyl)-1H-benzo[d]imidazol-6-yl)-5-methyl-4,5-dihydropyridazin-3(2H)-one (375);

#20. 7-(4-methyl-6-oxo-1,4,5,6-tetrahydropyridazin-3-yl)-9-(thiazol-2-yl)-1,3,4,5-tetrahydro-2H-benzo[b]azepin-2-one (354);

#21. 5-methyl-6-(1-methyl-2-(phenylamino)-1H-benzo[d]imidazol-6-yl)-4,5-dihydropyridazin-3(2H)-one (334);

#22. 6-(2-(benzo[d]thiazol-6-yloxy)-1H-benzo[d]imidazol-6-yl)-5-methyl-4,5-dihydropyridazin-3(2H)-one (377);

#23. 7-bromo-3,3-dimethyl-5-(4-methyl-6-oxo-1,4,5,6-tetrahydropyridazin-3-yl)indolin-2-one (350);

#24. 7-chloro-3,3-dimethyl-5-(4-methyl-6-oxo-1,4,5,6-tetrahydropyridazin-3-yl)indolin-2-one (306);

#25. 7-chloro-3,3-dimethyl-5-(6-oxo-1,6-dihydropyridazin-3-yl)indolin-2-one (289);

#26. 7-fluoro-3,3-dimethyl-5-(4-methyl-6-oxo-1,4,5,6-tetrahydropyridazin-3-yl)indolin-2-one (290);

#27. 7-fluoro-3,3-dimethyl-5-(6-oxo-1,6-dihydropyridazin-3-yl)indolin-2-one (274);

#28. 7'-fluoro-5'-(4-methyl-6-oxo-1,4,5,6-tetrahydropyridazin-3-yl)spiro[cyclopropane-1,3'-indolin]-2'-one (288);

#29. 4-chloro-6-(4-methyl-6-oxo-1,4,5,6-tetrahydropyridazin-3-yl)benzo[d]thiazol-2 (3H)-one (296);

#30. 6-(2-amino-4-chlorobenzo[d]thiazol-6-yl)-5-methyl-4,5-dihydropyridazin-3(2H)-one (295);

#31. 6-(2-amino-4-fluorobenzo[d]thiazol-6-yl)-5-methyl-4,5-dihydropyridazin-3(2H)-one (279);

#32. 7-bromo-3,3-dimethyl-5-(6-oxo-1,6-dihydropyridazin-3-yl)indolin-2-one (334);

#33. (R)-7-chloro-3,3-dimethyl-5-(4-methyl-6-oxo-1,4,5,6-tetrahydropyridazin-3-yl)indolin-2-one (306);

#34. 6-(4-fluoro-2-(methylamino)benzo[d]thiazol-6-yl)-5-methyl-4,5-dihydropyridazin-3(2H)-one (292);

#35. 8-chloro-6-(4-methyl-6-oxo-1,4,5,6-tetrahydropyridazin-3-yl)quinolin-2(1H)-one (290);

#36. 7-chloro-6-fluoro-3,3-dimethyl-5-(4-methyl-6-oxo-1,4,5,6-tetrahydropyridazin-3-yl)indolin-2-one (324);

#37. 6-(4-fluoro-2-(3-hydroxyazetidin-1-yl)benzo[d]thiazol-6-yl)-5-methyl-4,5-dihydropyridazin-3(2H)-one (335);

#38. 2-amino-6-(4-methyl-6-oxo-1,4,5,6-tetrahydropyridazin-3-yl)benzo[d]thiazole-4-carbonitrile (285);

#39. 7-chloro-5-(4-methyl-6-oxo-1,4,5,6-tetrahydropyridazin-3-yl)isoindolin-1-one (278);

#40. 6-(4-methyl-6-oxo-1,4,5,6-tetrahydropyridazin-3-yl)-2-oxo-1,2-dihydroquinoline-8-carbonitrile (280);

#41. 7-chloro-3,3-dimethyl-5-(4-methyl-6-oxo-1,4,5,6-tetrahydropyridazin-3-yl)isoindolin-1-one (306);

#42. 4-chloro-1-methyl-6-(4-methyl-6-oxo-1,4,5,6-tetrahydropyridazin-3-yl)-1,3-dihydro-2H-benzo[d]imidazol-2-one (293);

#43. 7'-fluoro-5'-(4-methyl-6-oxo-1,4,5,6-tetrahydropyridazin-3-yl)spiro[cyclobutane-1,3'-indolin]-2'-one (301);

#44. 7-chloro-3,3-dimethyl-5-(6-oxo-1,4,5,6-tetrahydropyridazin-3-yl)indolin-2-one (291);

#45. 6-(8-bromo-2-hydroxyquinolin-6-yl)-5-methyl-4,5-dihydropyridazin-3(2H)-one (334);

#46. 6-(4-fluoro-2-(((1-methyl-1H-pyrazol-4-yl)methyl)amino)benzo[d]thiazol-6-yl)-5-methyl-4,5-dihydropyridazin-3(2H)-one (373);

#47. 6-(7-chloro-3-methyl-1H-indazol-5-yl)-5-methyl-4,5-dihydropyridazin-3(2H)-one (277);

#48. 6-(8-cyclopropyl-2-hydroxyquinolin-6-yl)-5-methyl-4,5-dihydropyridazin-3(2H)-one (295);

#49. 6-(2-(3-methoxyazetidin-1-yl)benzo[d]thiazol-6-yl)-5-methyl-4,5-dihydropyridazin-3(2H)-one (330);

#50. 7-fluoro-5-(4-methyl-6-oxo-1,4,5,6-tetrahydropyridazin-3-yl)indolin-2-one (261);

#51. (S)-7-chloro-3,3-dimethyl-5-(4-methyl-6-oxo-1,4,5,6-tetrahydropyridazin-3-yl)isoindolin-2-one (305);

#52. 4-chloro-6-(6-oxo-1,6-dihydropyridazin-3-yl)benzo[d]thiazol-2 (3H)-one (280);

#53. 5-(4-methyl-6-oxo-1,4,5,6-tetrahydropyridazin-3-yl)-2-oxoindoline-7-carbonitrile (268);

#54. (R)-7-fluoro-5-(4-methyl-6-oxo-1,4,5,6-tetrahydropyridazin-3-yl)indolin-2-one (261);

#55. 4-methyl-6-(6-methyl-2-oxo-3,6-dihydro-2H-1,3,4-thiadiazin-5-yl)benzo[d]thiazol-2 (3H)-one (293);

#56. 4-chloro-6-(6-methyl-2-oxo-3,6-dihydro-2H-1,3,4-thiadiazin-5-yl)benzo[d]thiazol-2 (3H)-one (313);

#57. 5-(7-fluoro-2-oxoindolin-5-yl)-6-methyl-3,6-dihydro-2H-1,3,4-thiadiazin-2-one (279);

#58. 5-(7'-chloro-2'-oxospiro[cyclopropane-1,3'-indolin]-5'-yl)-6-methyl-3,6-dihydro-2H-1,3,4-thiadiazin-2-one (322);

#59. 5-(7-fluoro-3,3-dimethyl-2-oxoindolin-5-yl)-3,6-dihydro-2H-1,3,4-thiadiazin-2-one (293);

#60. (R)-5-(2-hydroxy-8-methylquinolin-6-yl)-6-methyl-3,6-dihydro-2H-1,3,4-thiadiazin-2-one (287);

#61. 5-(7-chloro-3,3-dimethyl-2-oxoindolin-5-yl)-3,6-dihydro-2H-1,3,4-thiadiazin-2-one (310);

#62. 5-(7-chloro-2-oxoindolin-5-yl)-6-methyl-3,6-dihydro-2H-1,3,4-thiadiazin-2-one (294);

#63. 6-methyl-5-(7-(4-(methylsulfonyl)phenyl)-2-oxoindolin-5-yl)-3,6-dihydro-2H-1,3,4-thiadiazin-2-one (415);

#64. 5-(9-chloro-2-oxo-2,3,4,5-tetrahydro-1H-benzo[b]azepin-7-yl)-6-methyl-3,6-dihydro-2H-1,3,4-thiadiazin-2-one (324);

#65. 5-(8-bromo-2-oxo-1,2,3,4-tetrahydroquinolin-6-yl)-6-methyl-3,6-dihydro-2H-1,3,4-thiadiazin-2-one (354);

#66. 5-(7-bromo-3,3-dimethyl-2-oxoindolin-5-yl)-3,6-dihydro-2H-1,3,4-thiadiazin-2-one (354);

#67. (6R)-5-(8-chloro-4,4-dimethyl-2-oxo-1,2,3,4-tetrahydroquinolin-6-yl)-6-methyl-3,6-dihydro-2H-1,3,4-thiadiazin-2-one (338);

#68. 5-(3,3-dimethyl-2-oxo-7-(thiazol-4-yl)indolin-5-yl)-6-methyl-3,6-dihydro-2H-1,3,4-thiadiazin-2-one (372);

#69. 5-(7-bromo-2-oxoindolin-5-yl)-6-methyl-3,6-dihydro-2H-1,3,4-thiadiazin-2-one (340);

#70. 6-methyl-5-(2-oxo-7-phenylindolin-5-yl)-3,6-dihydro-2H-1,3,4-thiadiazin-2-one (337);

#71. 5-(7-(4-chlorophenyl)-2-oxoindolin-5-yl)-6-methyl-3,6-dihydro-2H-1,3,4-thiadiazin-2-one (372);

#72. 5-(2-oxo-2,3,4,5-tetrahydro-1H-benzo[b]azepin-7-yl)-3,6-dihydro-2H-1,3,4-thiadiazin-2-one (275);

#73. 6-methyl-5-(9-methyl-2-oxo-2,3,4,5-tetrahydro-1H-benzo[b]azepin-7-yl)-3,6-dihydro-2H-1,3,4-thiadiazin-2-one (304);

#74. 5-(7-fluoro-3,3-dimethyl-2-oxoindolin-5-yl)-6-methyl-3,6-dihydro-2H-1,3,4-thiadiazin-2-one (307);

#75. 5-(7-chloro-3,3-dimethyl-2-oxoindolin-5-yl)-6-methyl-3,6-dihydro-2H-1,3,4-thiadiazin-2-one (324);

#76. 5-(7-bromo-3,3-dimethyl-2-oxoindolin-5-yl)-6-methyl-3,6-dihydro-2H-1,3,4-thiadiazin-2-one (368);

#77. 5-(6-methyl-2-oxo-3,6-dihydro-2H-1,3,4-thiadiazin-5-yl)-2-oxoindoline-7-carbonitrile (286);

#78. (S)-5-(7-fluoro-2-oxoindolin-5-yl)-6-methyl-3,6-dihydro-2H-1,3,4-thiadiazin-2-one (279);

#79. 5-(7-chloro-1-oxoisoindolin-5-yl)-6-methyl-3,6-dihydro-2H-1,3,4-thiadiazin-2-one (296);

#80. 5-(7-chloro-3,3-dimethyl-1-oxoisoindolin-5-yl)-6-methyl-3,6-dihydro-2H-1,3,4-thiadiazin-2-one (324);

#81. 5-(8-chloro-2-hydroxyquinolin-6-yl)-6-methyl-3,6-dihydro-2H-1,3,4-thiadiazin-2-one (308);

#82. 5-(7-chloro-2,2-dioxido-1,3-dihydrobenzo[c]isothiazol-5-yl)-6-methyl-3,6-dihydro-2H-1,3,4-thiadiazin-2-one (332);

#83. 6-methyl-5-(8-methyl-2-oxo-1,2,3,4-tetrahydroquinolin-6-yl)-3,6-dihydro-2H-1,3,4-thiadiazin-2-one (289);

#84. 4-chloro-6-(2-oxo-2,3-dihydro-1H-pyrrolo[2,3-b]pyridin-5-yl)benzo[d]oxazol-2 (3H)-one (300);

#85. 5-(7-chloro-3,3-dimethyl-2-oxoindolin-5-yl)-1,3-dihydro-2H-pyrrolo[2,3-b]pyridin-2-one (328).

#86. 7-chloro-3,3-dimethyl-5-(pyrimidin-5-yl)indolin-2-one (274);

#87. 6-(7-chloro-3,3-dimethyl-2-oxoindolin-5-yl)-3,4-dihydro-1,8-naphthyridin-2(1H)-one (340);

#88. 4-chloro-6-(5-oxo-4,5-dihydro-1,3,4-thiadiazol-2-yl) benzo[d]thiazol-2 (3H)-one (286); and

#89. 5-(7-chloro-3,3-dimethyl-2-oxoindolin-5-yl)-1,3,4-thiadiazol-2 (3H)-one (296).

The respective compound chemical structures for Examples 1-89 are depicted below.

(1)

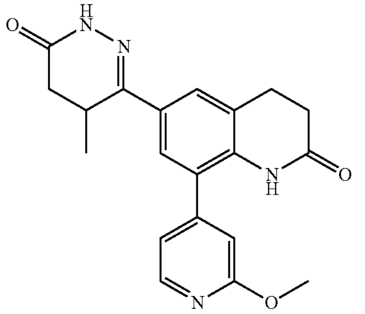

(2)

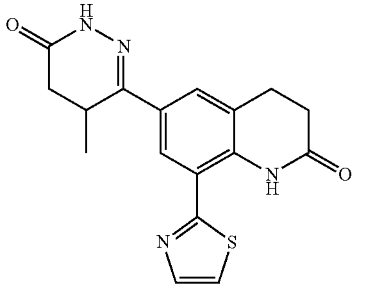

(3)

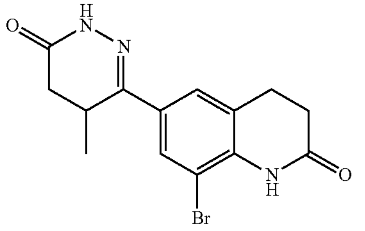

-continued (4)

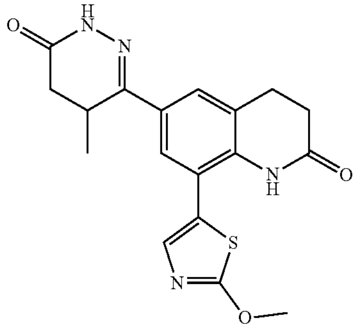

(5)

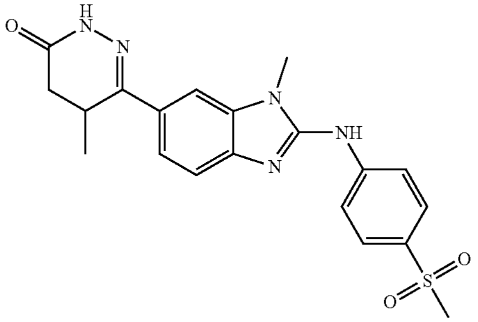

(6)

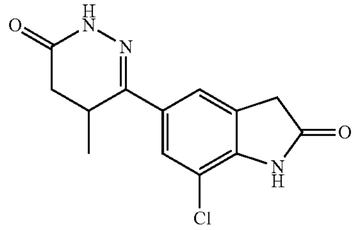

(7)

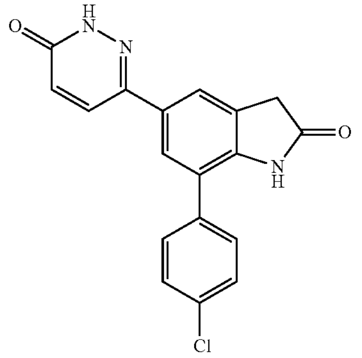

(8)

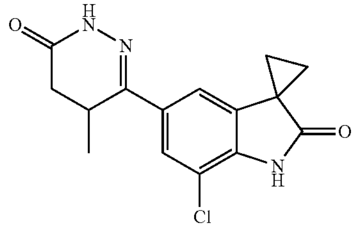

-continued
(9)
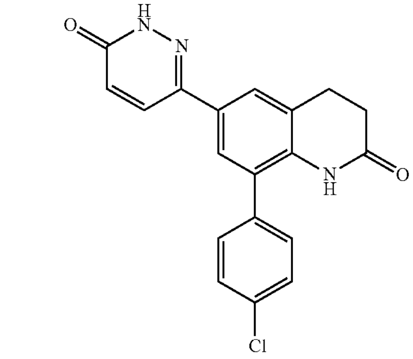
(10)
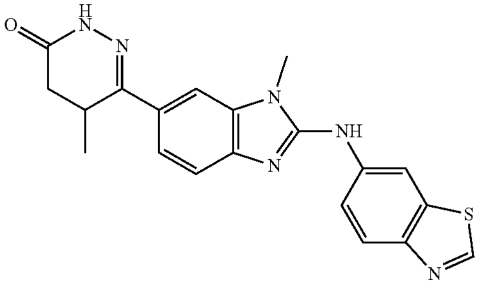
(11)
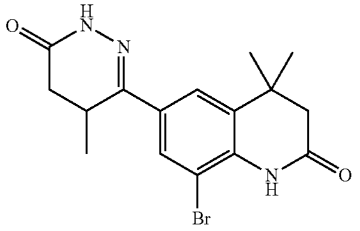
(12)
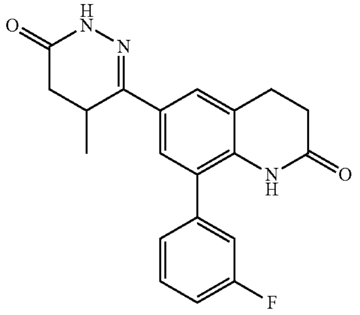
(13)
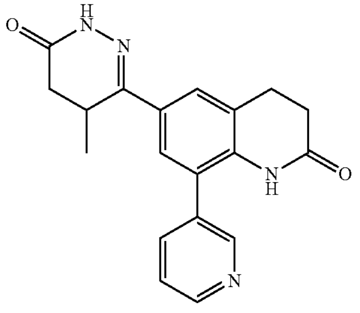
-continued
(14)
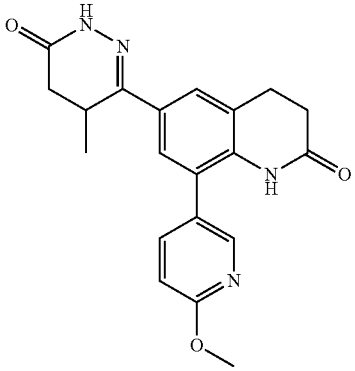
(15)
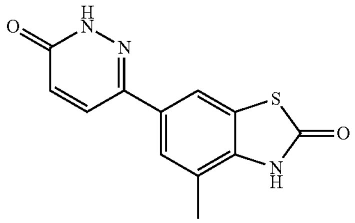
(16)
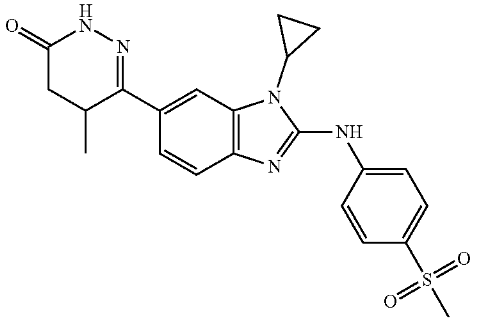
(17)
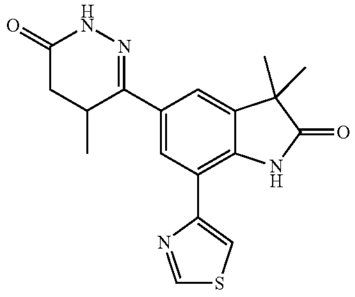
(18)
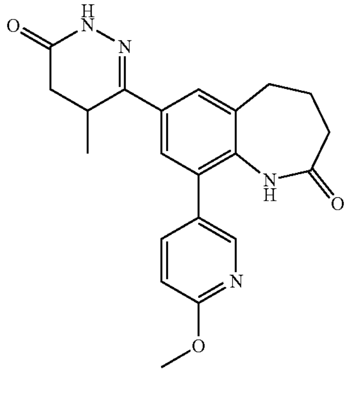

-continued
(19)
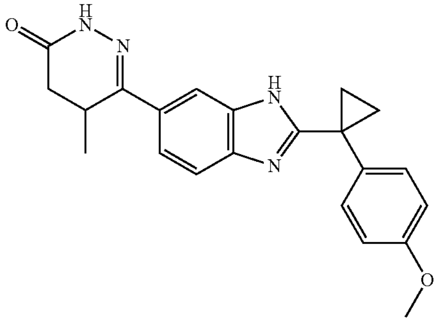
(20)
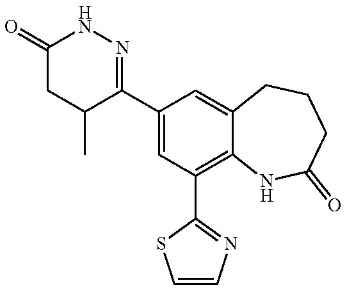
(21)
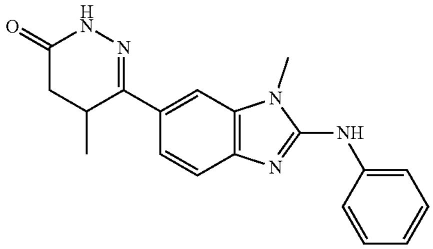
(22)
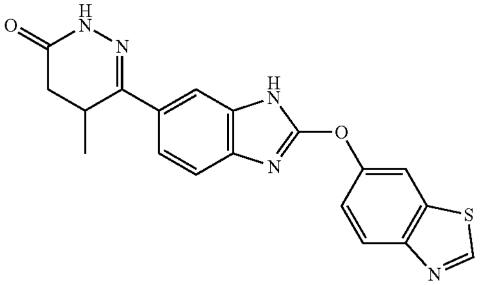
(23)
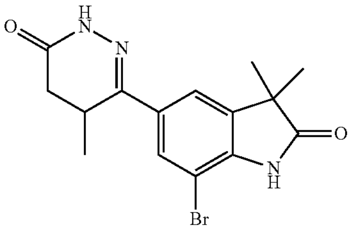
(24)
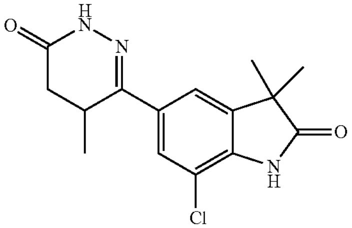
-continued
(25)
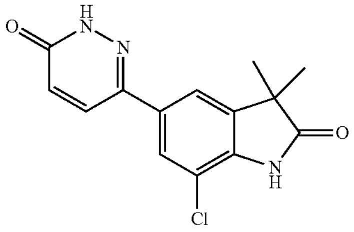
(26)
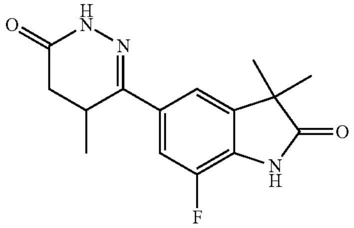
(27)
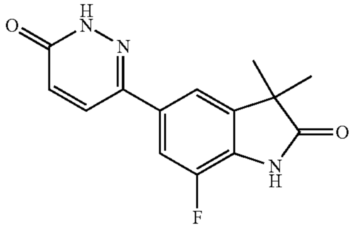
(28)
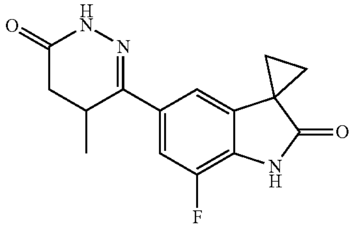
(29)
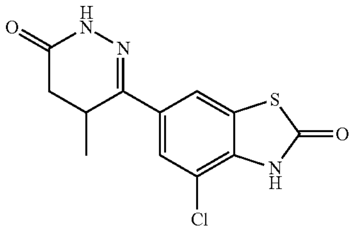
(30)
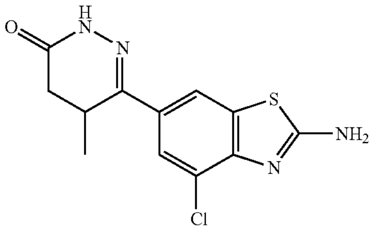

-continued
(31)
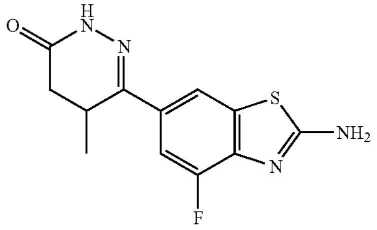
(32)
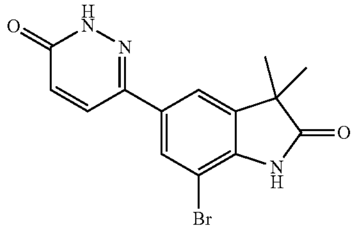
(33)
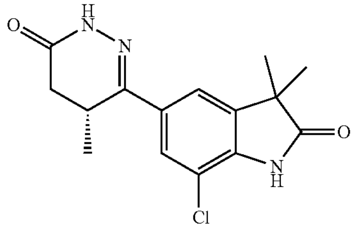
(34)
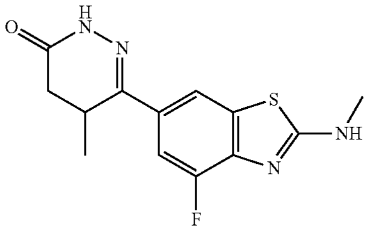
(35)
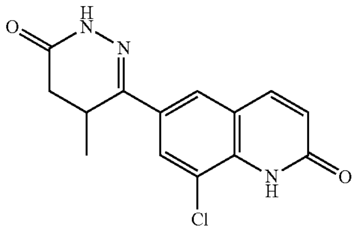
(36)
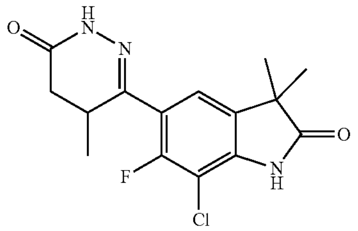
-continued
(37)
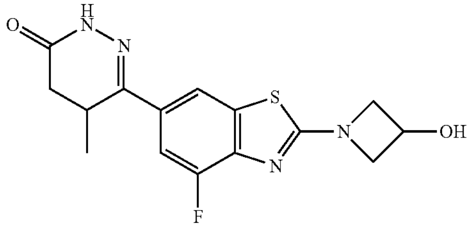
(38)
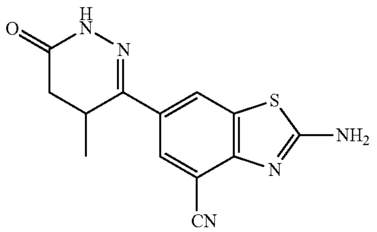
(39)
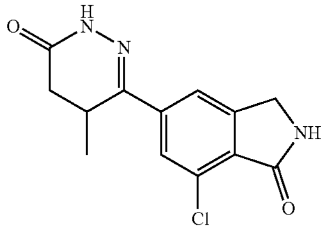
(40)
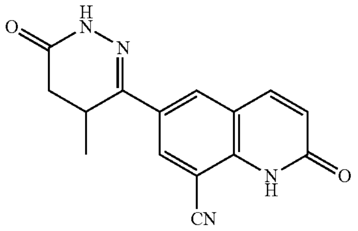
(41)
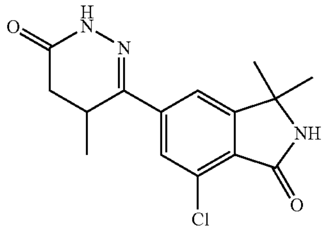
(42)
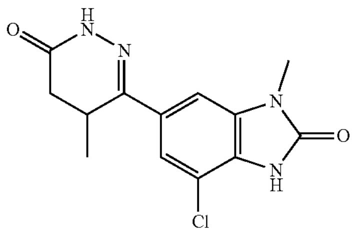

-continued
(43)
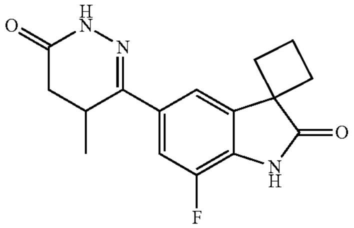
(44)
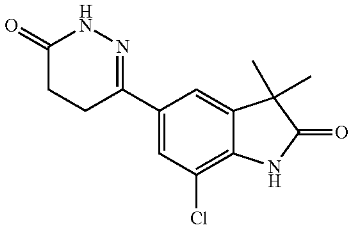
(45)
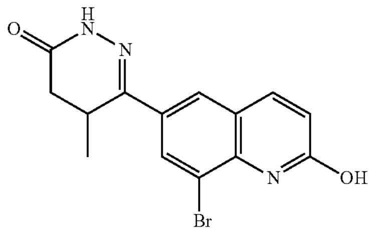
(46)
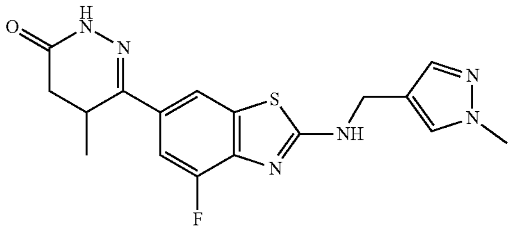
(47)
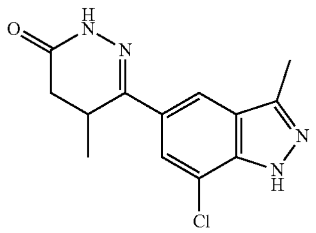
(48)
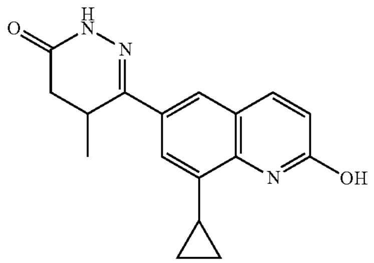
-continued
(49)
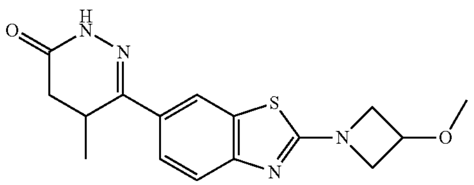
(50)
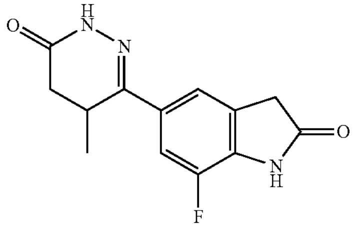
(51)
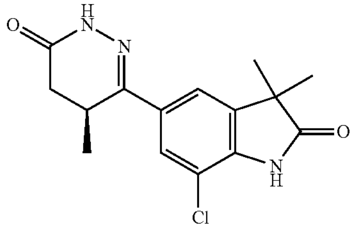
(52)
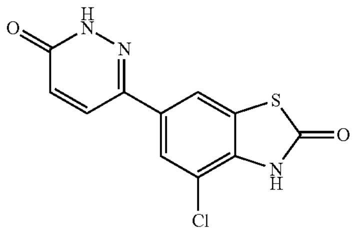
(53)
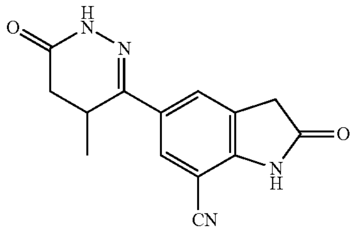
(54)
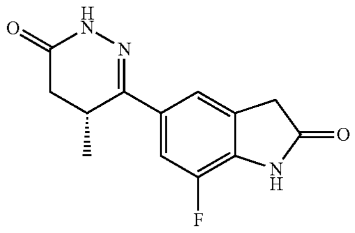
(55)
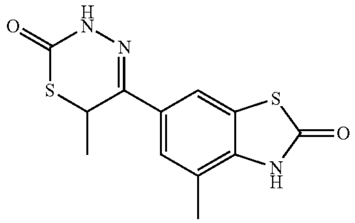

-continued
(56)
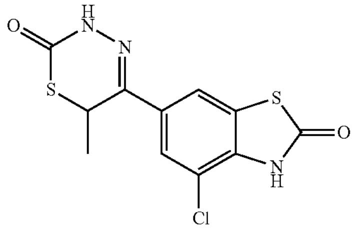
(57)
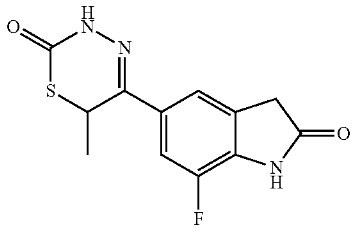
(58)
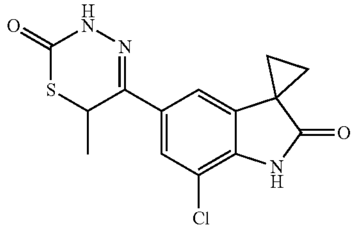
(59)
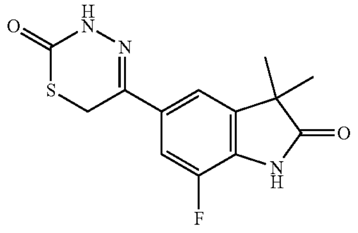
(60)
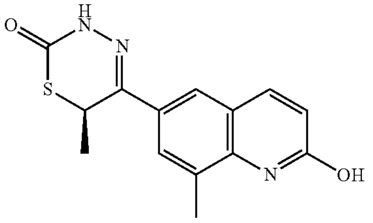
(61)
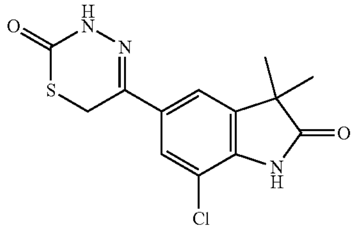
-continued
(62)
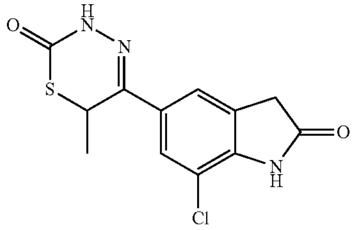
(63)
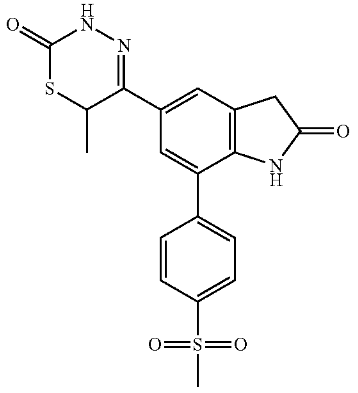
(64)
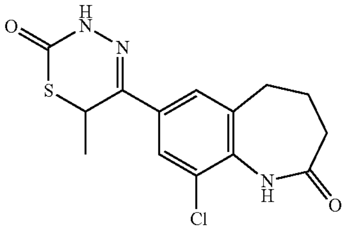
(65)
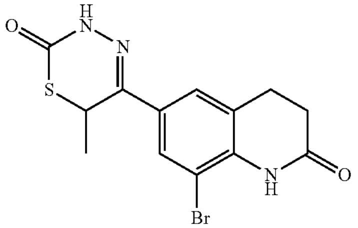
(66)
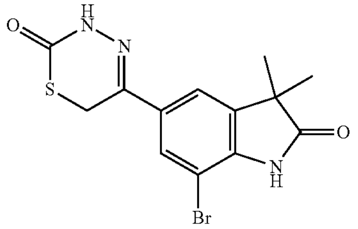
(67)
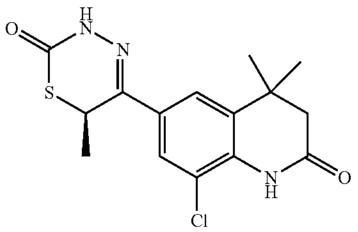

-continued
(68)
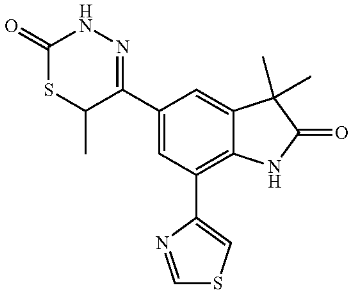
(69)
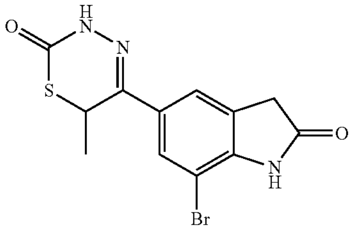
(70)
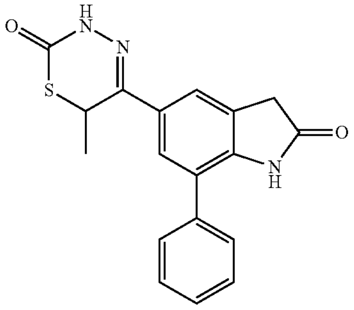
(71)
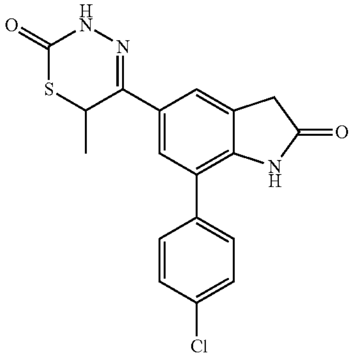
(72)
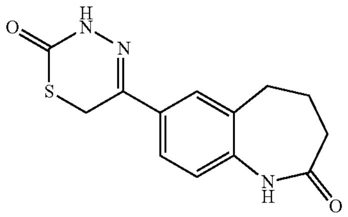
-continued
(73)
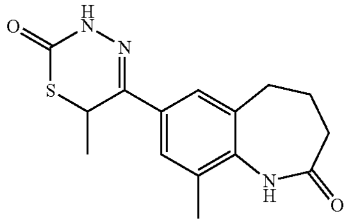
(74)
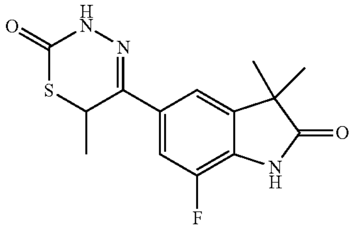
(75)
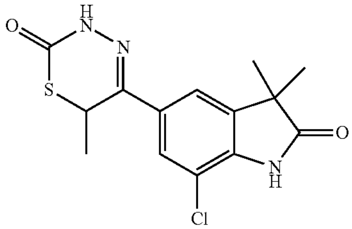
(76)
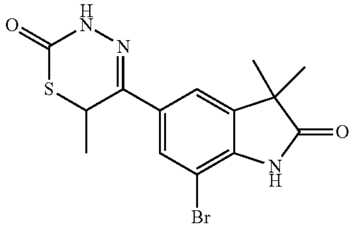
(77)
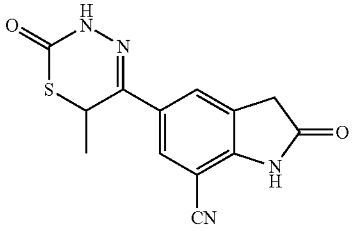
(78)
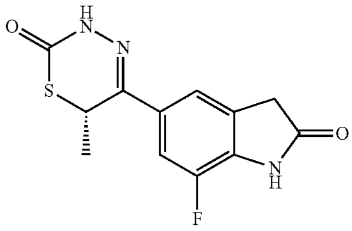

-continued (79)

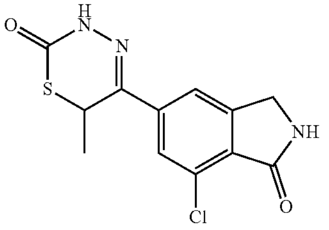

(80)

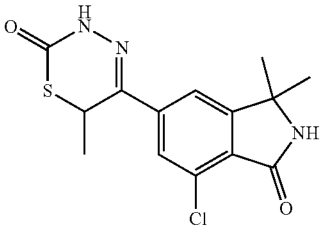

(81)

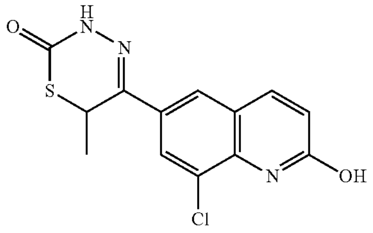

(82)

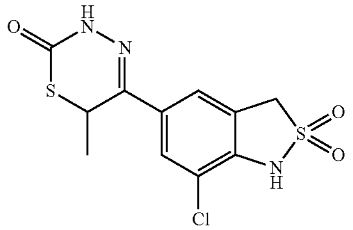

(83)

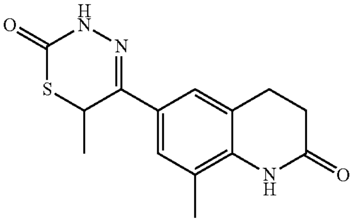

(84)

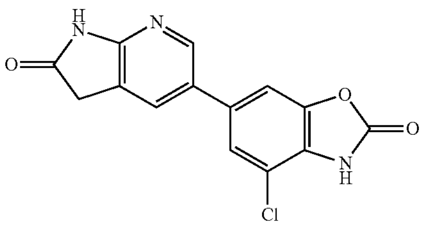

(85)

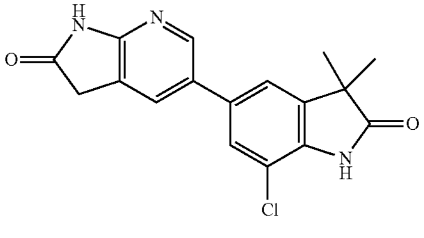

-continued (86)

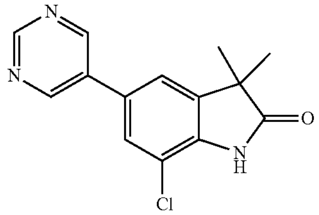

(87)

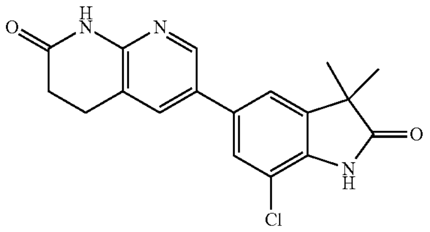

(88)

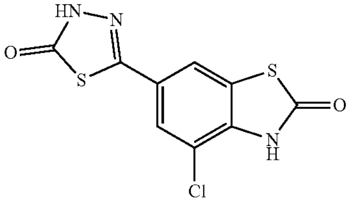

(89)

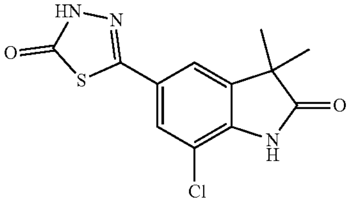

Pimobendan, a dihydropyridazinone inodilator/vasodilator has the chemical name, 6-(2-(4-methoxyphenyl)-1H-benzo[d]imidazol-6-yl)-5-methyl-4,5-dihydropyridazin-3(2H)-one, and structure shown below.

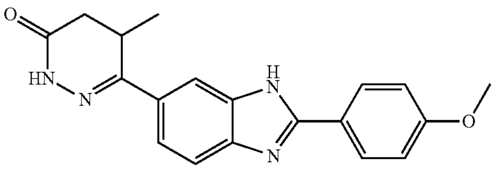 [SMILES: COc1ccc(-c2nc3ccc(C4=NNC(=O)CC4C)cc3[nH]2)cc1]

Pimobendan is absorbed rapidly when orally administered with a bioavailability of about 60-65%. The tmax and elimination half-life of pimobendan is about 2 hours and 1.6 hours, respectively. The des-methyl metabolite has a tmax and elimination half-life of about 3.2 hours and 5 hours, respectively. Pimobendan acts as a positive inotrope by sensitizing the affinity of calcium for binding to troponin C on cardiac myocytes and inhibiting PDE3. The inhibition of PDE3 also results in both arterial dilation and venodilation thereby improving cardiac output without increasing the myocardial oxygen consumption and is therefore used in the treatment of congestive heart failure secondary to myxomatous mitral valve disease or dilated cardiomyopathy in dogs. Cardiac troponin I (cTnI) is a protein unique to the heart and is a specific and sensitive biomarker of myocardial damage. In healthy animals, the concentration of cardiac troponin in blood should be virtually zero, so any significant elevation indicates some degree of myocardial damage. Monitoring the effect of PDE3 candidates on cTnI circulating in the blood can provide an alert to any concerns for cardiomyocyte damage and help inform safety assessments in future studies. In addition, cTnI can be used as a prognostic biomarker due to its strong association with mortality in dogs.

Biological Methods:

cPDE3A Assay (Fluorescent Polarization)

The canine PDE3A assay kit was purchased from BPS Bioscience (San Diego, CA) which included dog PDE3A recombinant enzyme, FAM-cyclic-3',5'-AMP (20 μM), PDE3 assay buffer, binding agent, binding agent diluent and microtiter 96-well plates. Compounds were initially dissolved in DMSO. The stock concentration was subsequently diluted in cPDE assay buffer (10× stock) and serially diluted to give a concentration response curve starting at 10 μM (≥7 total concentrations). Following the serial dilution, compound solution (0.1% final DMSO) was transferred to an assay plate (96-well) where the remaining canine PDE3A assay reagents were dispensed according to the BPS Bioscience® protocol (catalog #79735) procedure using a final concentration of 5 pg/μL of enzyme. Each compound was evaluated for the inhibition of the canine PDE3A enzyme activity using the measurement of fluorescent polarization changes. The 50% inhibition concentration ($IC_{50}$) nM was calculated and reported. As a comparison to the current cPDE3 inhibitors of the invention, pimobendan had a cPDE3 $IC_{50}$ value of about 1530 nM. The cPDE3 inhibitory data ($IC_{50}$) in nanomolar (nM) for the compounds of the invention are shown in Table 1.

Human iPS Cardiomyocyte Contractility Assay

Frozen human iCell® cardiomyocytes (FujiFilm® Cellular Dynamics Inc.) were thawed and plated in the center of each well of an Axion® Biosystems cytoview 24-well microelectrode array plate that was coated with human fibronectin in a 5-6 μL droplet at a density of 7-10×$10^6$ cells/mL. The cells were maintained in culture in a 37° C. humidified incubator at 5% $CO_2$. After at least seven days in culture with maintenance media changes every 2-3 days, the cells were paced at 2 Hz for approximately 48 hours on the Axion® Biosystems Maestro Pro instrument using the field potential application in the Axis Navigator software before returning to the spontaneous beating for at least 10 minutes in the contractility application (i.e., Axion® Biosystems procedure for Positive Inotropy Protocol). A baseline recording for three minutes was recorded prior to the addition of test articles to the plate followed by recording spontaneous beating for at least sixty minutes with three-minute recording every ten minutes. Readings were taken at 3, 13, 23, 33, 43 and 53 minutes. Compounds were dissolved in DMSO and tested at a final concentration of 30 μM with a final DMSO concentration of 0.3%. Compound solutions were transferred to the cell plates on the instrument after the baseline recording. Each compound was evaluated for the contractility response relative to the vehicle control (DMSO). Statistically significant changes in contractility at the last time point (53 minutes) as defined by changes in mean % delta beat amplitude is described with a "+" notation in Table 1. Contractility changes at the last time point that were not significant from vehicle were described with "*". For these, significance was obtained at earlier time points.

TABLE 1

| cPDE3 Inhibition ($IC_{50}$) in nM and Contractility | |
|---|---|
| Ex# | $IC_{50}$ |
| 1 (+) | 29.2 |
| 2 (+) | 23.5 |
| 3 (+) | 3.2 |
| 4 (+) | 24.8 |
| 5 (+) | 4.9 |
| 6 (*) | 6.2 |
| 7 (+) | 40.6 |
| 8 (+) | 3.9 |
| 9 (+) | 13.6 |
| 10 (+) | 7.3 |
| 11 (+) | 51.3 |
| 12 (+) | 90.9 |
| 13 (+) | 44.4 |
| 14 (+) | 50.2 |
| 15 (+) | 17.6 |
| 16 (+) | 5 |
| 17 (+) | 62.4 |
| 18 (+) | 42.1 |
| 19 (*) | 22.2 |
| 20 (+) | 32.4 |
| 21 (+) | 22.7 |
| 22 (+) | 33.1 |
| 23 (+) | 9.1 |
| 24 (+) | 5.4 |
| 25 (+) | 15.7 |
| 26 (+) | 7.4 |
| 27 (*) | 38.3 |
| 28 (+) | 3.4 |
| 29 (+) | 3.2 |
| 30 (+) | 4 |
| 31 (*) | 5.5 |
| 32 (+) | 26.7 |
| 33 (+) | 3.2 |
| 34 (NT) | 3.7 |
| 35 (NT) | 3.2 |
| 36 (NT) | 3.6 |
| 37 (NT) | 6.1 |
| 38 (+) | 7.4 |
| 39 (NT) | 10.5 |
| 40 (+) | 12 |
| 41 (NT) | 15.4 |
| 42 (+) | 16.2 |
| 43 (NT) | 35.5 |
| 44 (+) | 94 |
| 45 (+) | 3.2 |
| 46 (NT) | 3.4 |
| 47 (NT) | 4 |
| 48 (+) | 18 |
| 49 (NT) | 48.6 |
| 50 (+) | 4.9 |
| 51 (*) | 336 |
| 52 (NT) | 24.7 |
| 53 (*) | 32.7 |
| 54 (NT) | 7.4 |
| 55 (+) | 3.8 |
| 56 (+) | 3.6 |
| 57 (+) | 14.2 |
| 58 (+) | 8.4 |
| 59 (+) | 22.2 |
| 60 (+) | 4.7 |
| 61 (*) | 14.8 |
| 62 (+) | 11.2 |
| 63 (+) | 30.5 |
| 64 (+) | 3.2 |
| 65 (+) | 4.3 |
| 66 (+) | 24.4 |
| 67 (+) | 48.3 |
| 68 (+) | 118 |
| 69 (+) | 10.9 |
| 70 (+) | 80.7 |
| 71 (+) | 90.4 |
| 72 (+) | 28.2 |
| 73 (+) | 4.9 |
| 74 (+) | 13.3 |
| 75 (+) | 9.7 |
| 76 (+) | 15.2 |

TABLE 1-continued

| cPDE3 Inhibition ($IC_{50}$) in nM and Contractility | |
|---|---|
| Ex# | $IC_{50}$ |
| 77 (+) | 41.6 |
| 78 (+) | 7.8 |
| 79 (NT) | 20.3 |
| 80 (NT) | 20.6 |
| 81 (*) | 3.2 |
| 82 (NT) | 26.4 |
| 83 (+) | 3.2 |
| 84 (+) | 112 |
| 85 (+) | 49.7 |
| 86 (+) | 115 |
| 87 (+) | 3.4 |
| 88 (NT) | 29.2 |
| 89 (+) | 25.3 |
| pimobendan (+) | 1530 |

(NT)—Not Tested

As can be observed in Table 1, the compounds of the invention have a much greater affinity for cPDE3 than other known cPDE3 inhibitors. On average, the compounds of the invention have an $IC_{50}$ binding affinity (27.1 nM (2408/89)) to the cPDE3 receptor that are about 57-fold greater than pimobendan (1530/27). For examples 19, 57, 61, 62 and 73 the average cPDE3 $IC_{50}$ is about 13.5 which is about 113-fold greater than pimobendan. For examples 23, 24, 74, 75 and 76, compounds with a longer terminal half-life, the average cPDE3 $IC_{50}$ is about 10.5 nM which is about 129-fold greater than pimobendan. Therefore, lower doses of any one of the compounds of the invention can lead to increased levels of cPDE3 inhibition and higher levels of c-AMP and subsequent inotropic effects, thereby driving cardiac muscle contraction and smooth muscle dilation. As strong inotropes, the compounds of the invention can be useful for the treatment of CHF, MMVD and/or asymptomatic heart failure in animals, particularly, canines.

Myocardial contractility represents the innate ability of the heart muscle to contract. The ability to produce changes in force during contraction result from incremental degrees of binding between different types of tissues, i.e., between filaments of myosin and actin tissue. Contractility is an intrinsic property of these myocardial fibers. The degree of binding depends upon the concentration of calcium ions in the cell and also to myofilament responsiveness to calcium. Within an in-vivo intact heart, the action/response of the sympathetic nervous system is driven by precisely timed releases of a catecholamine, which is a process that determines the concentration of calcium ions in the cytosol of cardiac muscle cells. The factors causing an increase in contractility work by causing an increase in intracellular calcium ions ($Ca^{2+}$) during contraction. A measurable relative increase in contractility is a property of the myocardium similar to the term "inotropy". Contractility may be iatrogenically altered by the administration of inotropic agents. Drugs that positively render the effects of catecholamines such as norepinephrine, epinephrine and pimobendan that enhance contractility are considered to have a positive inotropic effect. As such, an increase in contractility generally results in increased cardiac output. Human cardiomyocytes that are chronically paced (2 Hz) for several days synchronize such that contractility or pharmacologically induced impedance changes can be measured. Pimobendan dose dependently increases contractility of cardiomyocytes as defined by changes in mean % delta beat amplitude. By contracting more, there will be an increase in left ventricular pressure. Cardiomyocyte contractibility of the compounds of the invention, as defined by changes in mean % delta beat amplitude, were determined to have a positive inotropic effect (i.e., a stronger cardiac muscle contraction force).

Further, Example #57 (30 μM) was tested in a contractility amplitude (CA) assay using adult human primary ventricular cardiomyocytes dissociated from human donor hearts to determine the potential of the compound to exert its positive inotropic effect by a single ($Ca^{2+}$ sensitization or inhibition of PDE3) or dual ($Ca^{2+}$ sensitization and inhibition of PDE3) mechanism of action. Cardiomyocytes were incubated at 35° C. under continuous perfusion (2 mL/minute) in a buffer (vehicle) solution (HEPES (10 mM), NaCl (145 mM), KCl (4 mM), $MgCl_2$ 1 mM), $CaCl_2$) (1.8 mM) and dextrose (11.1 mM)) plus 0.1% DMSO). Cells were equilibrated for a minimum of 5 minutes and stimulated with 1.0 Hz with a 1.5× stimulation intensity. A 100 μM IBMX (3-isobutyl-1-methylxanthine) non-selective inhibitor of PDE was used. Treatment time and stimulation was 300 seconds at 1.0 Hz. Data was collected using MyoBLAZER™ (v 2.9.2) software. Equilibrated cells (n=12) were stimulated with supra-threshold voltage at 1 Hz pacing frequency (bipolar pulse of 3 ms duration). Starting at 1 V, the amplitude of the stimulating pulse was increased until the cardiomyocytes started generating contraction-relaxation cycles. Contractility amplitude was calculated from the average of the last 20 contractility transients. Contractility amplitude for vehicle, IBMX and IBMX with Example #57 was 100, 136.8 and 267.6, respectively. Differences in CA between vehicle and IBMX; vehicle and IBMX+Ex #57; and IBMX and IBMX+Ex #57 were significantly different. IBMX increased CA by inhibiting PDE, however, there was an even larger increase in CA in the presence of Ex #57. Additionally, the CA assay was used to assess the potential of Ex #57 to exert a shift in the calcium concentration $EC_{50}$. The $EC_{50}$ for cardiomyocytes without Ex #57 was 1286 μM wherein the $EC_{50}$ with Ex #57 was 821 μM. From this second CA study, contractility of the myocytes was dose dependent on calcium concentration. Contractility at 100 μM, 1000 μM and 10,000 μM $CaCl_2$ was 3.11, 56.31 and 228.61, respectively. With the addition of 30 μM Ex #57, respective contractility values increased to 40.17, 182.67 and 284.27. Overall, these contractility studies clearly show that there is an additive effect of calcium sensitization, independent of PDE3 inhibition, thereby supporting the dual-modal cardiotonic activity.

Lastly, plasma half-life was assessed for a number of compounds in dogs. Beagle dogs were given an oral dose (0.1 mg/kg) of the respective compound accounting for a dose amount of about 1 mg/dog. Pimopendan was administered at a 0.3 mg/kg dose. Plasma samples were obtained over a 72-hour period and plasma half-life was calculated. The dog plasma half-lives (t %) in hours are presented in Table 2.

TABLE 2

| Dog Plasma Compound Half-life (hours) | |
|---|---|
| Example # | t½ (hrs) |
| 12 | 10.4 |
| 19 | 16 |
| 23 | 94 |
| 24 | 50 |
| 25 | 50 |
| 55 | 3.2 |
| 56 | 15 |
| 57 | 10 |

TABLE 2-continued

| Dog Plasma Compound Half-life (hours) | |
|---|---|
| Example # | t½ (hrs) |
| 58 | 7 |
| 59 | 5.2 |
| 61 | 8.5 |
| 62 | 5 |
| 66 | 10.2 |
| 68 | 12 |
| 71 | 5.4 |
| 72 | 3.9 |
| 73 | 7.5 |
| 74 | 55 |
| 75 | 50 |
| 76 | 40 |
| 85 | 9 |
| 86 | 96 |
| pimobendan | 0.4 |

As can be observed in Table 2, the compounds of the invention have a much greater half-life than pimobendan. Therefore, it is likely that the compounds of the invention can be dosed once daily (versus twice daily like pimobendan) or even dosed once every few days (e.g., twice a week).

NT-proBNP is a standard circulating biomarker of canine MMVD secreted by ventricular cardiomyocytes in response to stretching from volume or pressure overload. It is a well-defined diagnostic and prognostic biological indicator of myocardial wall stress and can be used as a biomarker for acute changes in left ventricular loading conditions. In some in-house studies, NT-proBNP was assessed as a biomarker that showed a 30% reduction in NT-proBNP, which has been associated by others to indicate a reduction in cardiac wall stress and improved quality of life. In one instance, Example #26 had reduced NT-proBNP levels by 49% and 62% at doses of 0.03 and 0.1 mg/kg, respectively, over a 12 hour period. In contrast, the labeled dose of pimobendan had a 41% decrease in NT-proBNP at 24 hours post does. This positive pharmacological effect suggests a clinically relevant reduction in myocardial stress, thus potentially delaying cardiac disease progression.

We claim:

1. A compound selected from the group consisting of:

8-(2-methoxypyridin-4-yl)-6-(4-methyl-6-oxo-1,4,5,6-tetrahydropyridazin-3-yl)-3,4-dihydroquinolin-2(1H)-one;

6-(4-methyl-6-oxo-1,4,5,6-tetrahydropyridazin-3-yl)-8-(thiazol-2-yl)-3,4-dihydroquinolin-2(1H)-one;

8-(2-methoxythiazol-5-yl)-6-(4-methyl-6-oxo-1,4,5,6-tetrahydropyridazin-3-yl)-3,4-dihydroquinolin-2(1H)-one;

7-chloro-5-(4-methyl-6-oxo-1,4,5,6-tetrahydropyridazin-3-yl) indolin-2-one;

7-(4-chlorophenyl)-5-(6-oxo-1,6-dihydropyridazin-3-yl) indolin-2-one;

7'-chloro-5'-(4-methyl-6-oxo-1,4,5,6-tetrahydro-pyridazin-3-yl)spiro[cyclopropane-1,3'-indolin]-2'-one;

8-(4-chlorophenyl)-6-(6-oxo-1,6-dihydropyridazin-3-yl)-3,4-dihydroquinolin-2(1H)-one;

8-(3-fluorophenyl)-6-(4-methyl-6-oxo-1,4,5,6-tetrahydropyridazin-3-yl)-3,4-dihydroquinolin-2(1H)-one;

6-(4-methyl-6-oxo-1,4,5,6-tetrahydropyridazin-3-yl)-8-(pyridin-3-yl)-3,4-dihydroquinolin-2(1H)-one;

3,3-dimethyl-5-(4-methyl-6-oxo-1,6-dihydropyridazin-3-yl)-7-(thiazol-4-yl) indolin-2-one;

9-(6-methoxypyridin-3-yl)-7-(4-methyl-6-oxo-1,4,5,6-tetrahydropyridazin-3-yl)-1,3,4,5-tetrahydro-2H-benzo[b]azepin-2-one;

6-(2-(1-(4-methoxyphenyl)cyclopropyl)-1H-benzo[d]imidazol-6-yl)-5-methyl-4,5-dihydropyridazin-3(2H)-one;

7-bromo-3,3-dimethyl-5-(4-methyl-6-oxo-1,4,5,6-tetrahydropyridazin-3-yl) indolin-2-one;

7-chloro-3,3-dimethyl-5-(4-methyl-6-oxo-1,4,5,6-tetrahydropyridazin-3-yl) indolin-2-one;

7-chloro-3,3-dimethyl-5-(6-oxo-1,6-dihydropyridazin-3-yl) indolin-2-one;

7-fluoro-3,3-dimethyl-5-(4-methyl-6-oxo-1,4,5,6-tetrahydropyridazin-3-yl) indolin-2-one;

7-fluoro-3,3-dimethyl-5-(6-oxo-1,6-dihydropyridazin-3-yl) indolin-2-one;

7'-fluoro-5'-(4-methyl-6-oxo-1,4,5,6-tetrahydro-pyridazin-3-yl)spiro[cyclopropane-1,3'-indolin]-2'-one;

7-chloro-3,3-dimethyl-5-(6-oxo-1,4,5,6-tetrahydro-pyridazin-3-yl) indolin-2-one;

4-chloro-6-(4-methyl-6-oxo-1,4,5,6-tetrahydropyridazin-3-yl)benzo[d]thiazol-2 (3H)-one;

6-(2-amino-4-chlorobenzo[d]thiazol-6-yl)-5-methyl-4,5-dihydropyridazin-3(2H)-one;

6-(2-amino-4-fluorobenzo[d]thiazol-6-yl)-5-methyl-4,5-dihydropyridazin-3(2H)-one;

7-bromo-3,3-dimethyl-5-(6-oxo-1,6-dihydropyridazin-3-yl) indolin-2-one;

(R)-7-chloro-3,3-dimethyl-5-(4-methyl-6-oxo-1,4,5,6-tetrahydropyridazin-3-yl) indolin-2-one;

6-(4-fluoro-2-(methylamino)benzo[d]thiazol-6-yl)-5-methyl-4,5-dihydropyridazin-3(2H)-one;

6-(8-chloro-2-hydroxyquinolin-6-yl)-5-methyl-4,5-dihydropyridazin-3(2H)-one;

7-chloro-6-fluoro-3,3-dimethyl-5-(4-methyl-6-oxo-1,4,5,6-tetrahydropyridazin-3-yl) indolin-2-one;

6-(4-fluoro-2-(3-hydroxyazetidin-1-yl)benzo[d]thiazol-6-yl)-5-methyl-4,5-dihydropyridazin-3(2H)-one;

2-amino-6-(4-methyl-6-oxo-1,4,5,6-tetrahydropyridazin-3-yl)benzo[d]thiazole-4-carbonitrile;

7-chloro-5-(4-methyl-6-oxo-1,4,5,6-tetrahydropyridazin-3-yl) isoindolin-1-one;

2-hydroxy-6-(4-methyl-6-oxo-1,4,5,6-tetrahydro-pyridazin-3-yl) quinoline-8-carbonitrile;

7-chloro-3,3-dimethyl-5-(4-methyl-6-oxo-1,4,5,6-tetrahydropyridazin-3-yl) isoindolin-1-one;

4-chloro-1-methyl-6-(4-methyl-6-oxo-1,4,5,6-tetrahydro-pyridazin-3-yl)-1,3-dihydro-2H-benzo[d]imidazol-2-one;

7'-fluoro-5'-(4-methyl-6-oxo-1,4,5,6-tetrahydro-pyridazin-3-yl)spiro[cyclobutane-1,3'-indolin]-2'-one;

6-(8-bromo-2-hydroxyquinolin-6-yl)-5-methyl-4,5-dihydropyridazin-3(2H)-one;

6-(4-fluoro-2-(((1-methyl-1H-pyrazol-4-yl)methyl)amino)benzo[d]thiazol-6-yl)-5-methyl-4,5-dihydro-pyridazin-3(2H)-one;

6-(7-chloro-3-methyl-1H-indazol-5-yl)-5-methyl-4,5-dihydropyridazin-3(2H)-one;

6-(8-cyclopropyl-2-hydroxyquinolin-6-yl)-5-methyl-4,5-dihydropyridazin-3(2H)-one;

6-(2-(3-methoxyazetidin-1-yl)benzo[d]thiazol-6-yl)-5-methyl-4,5-dihydropyridazin-3(2H)-one;

7-fluoro-5-(4-methyl-6-oxo-1,4,5,6-tetrahydropyridazin-3-yl) indolin-2-one;

(S)-7-chloro-3,3-dimethyl-5-(4-methyl-6-oxo-1,4,5,6-tetrahydropyridazin-3-yl) isoindolin-2-one;

4-chloro-6-(6-oxo-1,6-dihydropyridazin-3-yl)benzo[d]thiazol-2 (3H)-one;

5-(4-methyl-6-oxo-1,4,5,6-tetrahydropyridazin-3-yl)-2-oxoindoline-7-carbonitrile;

4-methyl-6-(6-methyl-2-oxo-3,6-dihydro-2H-1,3,4-thiadiazin-5-yl)benzo[d]thiazol-2 (3H)-one;

4-chloro-6-(6-methyl-2-oxo-3,6-dihydro-2H-1,3,4-thiadiazin-5-yl)benzo[d]thiazol-2 (3H)-one;

5-(7-fluoro-2-oxoindolin-5-yl)-6-methyl-3,6-dihydro-2H-1,3,4-thiadiazin-2-one;

5-(7'-chloro-2'-oxospiro[cyclopropane-1,3'-indolin]-5'-yl)-6-methyl-3,6-dihydro-2H-1, 3,4-thiadiazin-2-one;

5-(7-fluoro-3,3-dimethyl-2-oxoindolin-5-yl)-3,6-dihydro-2H-1,3,4-thiadiazin-2-one;

5-(7-chloro-3,3-dimethyl-2-oxoindolin-5-yl)-3,6-dihydro-2H-1,3,4-thiadiazin-2-one;

5-(7-chloro-2-oxoindolin-5-yl)-6-methyl-3,6-dihydro-2H-1,3,4-thiadiazin-2-one;

6-methyl-5-(7-(4-(methylsulfonyl)phenyl)-2-oxoindolin-5-yl)-3,6-dihydro-2H-1,3,4-thiadiazin-2-one;

5-(7-bromo-3,3-dimethyl-2-oxoindolin-5-yl)-3,6-dihydro-2H-1,3,4-thiadiazin-2-one;

5-(3,3-dimethyl-2-oxo-7-(thiazol-4-yl) indolin-5-yl)-6-methyl-3,6-dihydro-2H-1,3,4-thiadiazin-2-one;

5-(7-(4-chlorophenyl)-2-oxoindolin-5-yl)-6-methyl-3,6-dihydro-2H-1,3,4-thiadiazin-2-one;

5-(2-oxo-2,3,4,5-tetrahydro-1H-benzo[b]azepin-7-yl)-3,6-dihydro-2H-1,3,4-thiadiazin-2-one;

6-methyl-5-(9-methyl-2-oxo-2,3,4,5-tetrahydro-1H-benzo[b]azepin-7-yl)-3,6-dihydro-2H-1,3,4-thiadiazin-2-one;

5-(7-fluoro-3,3-dimethyl-2-oxoindolin-5-yl)-6-methyl-3,6-dihydro-2H-1,3,4-thiadiazin-2-one;

5-(7-chloro-3,3-dimethyl-2-oxoindolin-5-yl)-6-methyl-3,6-dihydro-2H-1,3,4-thiadiazin-2-one;

5-(7-bromo-3,3-dimethyl-2-oxoindolin-5-yl)-6-methyl-3,6-dihydro-2H-1,3,4-thiadiazin-2-one;

5-(6-methyl-2-oxo-3,6-dihydro-2H-1,3,4-thiadiazin-5-yl)-2-oxoindoline-7-carbonitrile;

(S)-5-(7-fluoro-2-oxoindolin-5-yl)-6-methyl-3,6-dihydro-2H-1,3,4-thiadiazin-2-one;

5-(7-chloro-1-oxoisoindolin-5-yl)-6-methyl-3,6-dihydro-2H-1,3,4-thiadiazin-2-one;

5-(7-chloro-3,3-dimethyl-1-oxoisoindolin-5-yl)-6-methyl-3,6-dihydro-2H-1,3,4-thiadiazin-2-one;

5-(8-chloro-2-hydroxyquinolin-6-yl)-6-methyl-3,6-dihydro-2H-1,3,4-thiadiazin-2-one;

5-(7-chloro-2,2-dioxido-1,3-dihydrobenzo[c]isothiazol-5-yl)-6-methyl-3,6-dihydro-2H-1,3,4-thiadiazin-2-one;

6-methyl-5-(8-methyl-2-oxo-1,2,3,4-tetrahydroquinolin-6-yl)-3,6-dihydro-2H-1,3,4-thiadiazin-2-one;

4-chloro-6-(2-oxo-2,3-dihydro-1H-pyrrolo[2,3-b]pyridin-5-yl)benzo[d]oxazol-2 (3H)-one;

5-(7-chloro-3,3-dimethyl-2-oxoindolin-5-yl)-1,3-dihydro-2H-pyrrolo[2,3-b]pyridin-2-one;

7-chloro-3,3-dimethyl-5-(pyrimidin-5-yl) indolin-2-one;

6-(7-chloro-3,3-dimethyl-2-oxoindolin-5-yl)-3,4-dihydro-1,8-naphthyridin-2(1H)-one;

4-chloro-6-(5-oxo-4,5-dihydro-1,3,4-thiadiazol-2-yl) benzo[d]thiazol-2 (3H)-one; and 5-(7-chloro-3,3-dimethyl-2-oxoindolin-5-yl)-1,3,4-thiadiazol-2 (3H)-one, stereoisomers thereof, and veterinarily acceptable salts thereof.

2. The compound of claim 1 selected form the group consisting of:

8-(2-methoxypyridin-4-yl)-6-(4-methyl-6-oxo-1,4,5,6-tetrahydropyridazin-3-yl)-3,4-dihydroquinolin-2(1H)-one;

8-(2-methoxythiazol-5-yl)-6-(4-methyl-6-oxo-1,4,5,6-tetrahydropyridazin-3-yl)-3,4-dihydroquinolin-2(1H)-one;

7-chloro-5-(4-methyl-6-oxo-1,4,5,6-tetrahydropyridazin-3-yl) indolin-2-one;

7'-chloro-5'-(4-methyl-6-oxo-1,4,5,6-tetrahydro-pyridazin-3-yl)spiro[cyclopropane-1,3'-indolin]-2'-one;

8-(4-chlorophenyl)-6-(6-oxo-1,6-dihydropyridazin-3-yl)-3,4-dihydroquinolin-2(1H)-one;

8-(3-fluorophenyl)-6-(4-methyl-6-oxo-1,4,5,6-tetrahydropyridazin-3-yl)-3,4-dihydroquinolin-2(1H)-one;

6-(4-methyl-6-oxo-1,4,5,6-tetrahydropyridazin-3-yl)-8-(pyridin-3-yl)-3,4-dihydroquinolin-2(1H)-one;

9-(6-methoxypyridin-3-yl)-7-(4-methyl-6-oxo-1,4,5,6-tetrahydropyridazin-3-yl)-1,3,4,5-tetrahydro-2H-benzo[b]azepin-2-one;

6-(2-(1-(4-methoxyphenyl)cyclopropyl)-1H-benzo[d]imidazol-6-yl)-5-methyl-4,5-dihydropyridazin-3(2H)-one;

7-bromo-3,3-dimethyl-5-(4-methyl-6-oxo-1,4,5,6-tetrahydropyridazin-3-yl) indolin-2-one;

7-chloro-3,3-dimethyl-5-(4-methyl-6-oxo-1,4,5,6-tetrahydropyridazin-3-yl) indolin-2-one;

7-chloro-3,3-dimethyl-5-(6-oxo-1,6-dihydropyridazin-3-yl) indolin-2-one;

7-fluoro-3,3-dimethyl-5-(4-methyl-6-oxo-1,4,5,6-tetrahydropyridazin-3-yl) indolin-2-one;

7-fluoro-3,3-dimethyl-5-(6-oxo-1,6-dihydropyridazin-3-yl) indolin-2-one;

7'-fluoro-5'-(4-methyl-6-oxo-1,4,5,6-tetrahydro-pyridazin-3-yl)spiro[cyclopropane-1,3'-indolin]-2'-one;

7-chloro-3,3-dimethyl-5-(6-oxo-1,4,5,6-tetrahydro-pyridazin-3-yl) indolin-2-one;

6-(2-amino-4-chlorobenzo[d]thiazol-6-yl)-5-methyl-4,5-dihydropyridazin-3(2H)-one;

6-(2-amino-4-fluorobenzo[d]thiazol-6-yl)-5-methyl-4,5-dihydropyridazin-3(2H)-one;

7-bromo-3,3-dimethyl-5-(6-oxo-1,6-dihydropyridazin-3-yl) indolin-2-one;

(R)-7-chloro-3,3-dimethyl-5-(4-methyl-6-oxo-1,4,5,6-tetrahydropyridazin-3-yl) indolin-2-one;

6-(4-fluoro-2-(methylamino)benzo[d]thiazol-6-yl)-5-methyl-4,5-dihydropyridazin-3(2H)-one;

6-(8-chloro-2-hydroxyquinolin-6-yl)-5-methyl-4,5-dihydropyridazin-3(2H)-one;

7-chloro-6-fluoro-3,3-dimethyl-5-(4-methyl-6-oxo-1,4,5,6-tetrahydropyridazin-3-yl) indolin-2-one;

6-(4-fluoro-2-(3-hydroxyazetidin-1-yl)benzo[d]thiazol-6-yl)-5-methyl-4,5-dihydropyridazin-3(2H)-one;

2-amino-6-(4-methyl-6-oxo-1,4,5,6-tetrahydropyridazin-3-yl)benzo[d]thiazole-4-carbonitrile;

7-chloro-5-(4-methyl-6-oxo-1,4,5,6-tetrahydropyridazin-3-yl) isoindolin-1-one;

2-hydroxy-6-(4-methyl-6-oxo-1,4,5,6-tetrahydro-pyridazin-3-yl) quinoline-8-carbonitrile;

7-chloro-3,3-dimethyl-5-(4-methyl-6-oxo-1,4,5,6-tetrahydropyridazin-3-yl) isoindolin-1-one;

4-chloro-1-methyl-6-(4-methyl-6-oxo-1,4,5,6-tetrahydro-pyridazin-3-yl)-1,3-dihydro-2H-benzo[d]imidazol-2-one;

7'-fluoro-5'-(4-methyl-6-oxo-1,4,5,6-tetrahydro-pyridazin-3-yl)spiro[cyclobutane-1,3'-indolin]-2'-one;

4-chloro-6-(6-methyl-2-oxo-3,6-dihydro-2H-1,3,4-thiadiazin-5-yl)benzo[d]thiazol-2 (3H)-one;

5-(7-fluoro-2-oxoindolin-5-yl)-6-methyl-3,6-dihydro-2H-1,3,4-thiadiazin-2-one;

5-(7'-chloro-2'-oxospiro[cyclopropane-1,3'-indolin]-5'-yl)-6-methyl-3,6-dihydro-2H-1,3,4-thiadiazin-2-one;

5-(7-fluoro-3,3-dimethyl-2-oxoindolin-5-yl)-3,6-dihydro-2H-1,3,4-thiadiazin-2-one;

5-(7-chloro-3,3-dimethyl-2-oxoindolin-5-yl)-3,6-dihydro-2H-1,3,4-thiadiazin-2-one;

5-(7-chloro-2-oxoindolin-5-yl)-6-methyl-3,6-dihydro-2H-1,3,4-thiadiazin-2-one;

6-methyl-5-(7-(4-(methylsulfonyl)phenyl)-2-oxoindolin-5-yl)-3,6-dihydro-2H-1,3,4-thiadiazin-2-one;

5-(7-bromo-3,3-dimethyl-2-oxoindolin-5-yl)-3,6-dihydro-2H-1,3,4-thiadiazin-2-one;

5-(7-(4-chlorophenyl)-2-oxoindolin-5-yl)-6-methyl-3,6-dihydro-2H-1,3,4-thiadiazin-2-one;

6-methyl-5-(9-methyl-2-oxo-2,3,4,5-tetrahydro-1H-benzo[b]azepin-7-yl)-3,6-dihydro-2H-1,3,4-thiadiazin-2-one;

5-(7-fluoro-3,3-dimethyl-2-oxoindolin-5-yl)-6-methyl-3,6-dihydro-2H-1,3,4-thiadiazin-2-one;

5-(7-chloro-3,3-dimethyl-2-oxoindolin-5-yl)-6-methyl-3,6-dihydro-2H-1,3,4-thiadiazin-2-one;

5-(7-bromo-3,3-dimethyl-2-oxoindolin-5-yl)-6-methyl-3,6-dihydro-2H-1,3,4-thiadiazin-2-one;

5-(6-methyl-2-oxo-3,6-dihydro-2H-1,3,4-thiadiazin-5-yl)-2-oxoindoline-7-carbonitrile;

(S)-5-(7-fluoro-2-oxoindolin-5-yl)-6-methyl-3,6-dihydro-2H-1,3,4-thiadiazin-2-one;

5-(7-chloro-1-oxoisoindolin-5-yl)-6-methyl-3,6-dihydro-2H-1,3,4-thiadiazin-2-one;

5-(7-chloro-3,3-dimethyl-1-oxoisoindolin-5-yl)-6-methyl-3,6-dihydro-2H-1,3,4-thiadiazin-2-one;

6-methyl-5-(8-methyl-2-oxo-1,2,3,4-tetrahydroquinolin-6-yl)-3,6-dihydro-2H-1,3,4-thiadiazin-2-one;

5-(7-chloro-3,3-dimethyl-2-oxoindolin-5-yl)-1,3-dihydro-2H-pyrrolo[2,3-b]pyridin-2-one; and 7-chloro-3,3-dimethyl-5-(pyrimidin-5-yl) indolin-2-one, stereoisomers thereof, and veterinary acceptable salts thereof.

3. The compound of claim 2 selected from the group consisting of:

8-(3-fluorophenyl)-6-(4-methyl-6-oxo-1,4,5,6-tetrahydropyridazin-3-yl)-3,4-dihydroquinolin-2(1H)-one;

6-(2-(1-(4-methoxyphenyl)cyclopropyl)-1H-benzo[d]imidazol-6-yl)-5-methyl-4,5-dihydropyridazin-3(2H)-one;

7-bromo-3,3-dimethyl-5-(4-methyl-6-oxo-1,4,5,6-tetrahydropyridazin-3-yl) indolin-2-one;

7-chloro-3,3-dimethyl-5-(4-methyl-6-oxo-1,4,5,6-tetrahydropyridazin-3-yl) indolin-2-one;

7-fluoro-3,3-dimethyl-5-(4-methyl-6-oxo-1,4,5,6-tetrahydropyridazin-3-yl) indolin-2-one;

7-fluoro-3,3-dimethyl-5-(6-oxo-1,6-dihydropyridazin-3-yl) indolin-2-one;

7'-fluoro-5'-(4-methyl-6-oxo-1,4,5,6-tetrahydropyridazin-3-yl)spiro[cyclopropane-1,3'-indolin]-2'-one;

6-(2-amino-4-chlorobenzo[d]thiazol-6-yl)-5-methyl-4,5-dihydropyridazin-3(2H)-one;

6-(2-amino-4-fluorobenzo[d]thiazol-6-yl)-5-methyl-4,5-dihydropyridazin-3(2H)-one;

7-bromo-3,3-dimethyl-5-(6-oxo-1,6-dihydropyridazin-3-yl) indolin-2-one;

(R)-7-chloro-3,3-dimethyl-5-(4-methyl-6-oxo-1,4,5,6-tetrahydropyridazin-3-yl) indolin-2-one;

4-chloro-6-(6-methyl-2-oxo-3,6-dihydro-2H-1,3,4-thiadiazin-5-yl)benzo[d]thiazol-2 (3H)-one;

5-(7-fluoro-2-oxoindolin-5-yl)-6-methyl-3,6-dihydro-2H-1,3,4-thiadiazin-2-one;

5-(7'-chloro-2'-oxospiro[cyclopropane-1,3'-indolin]-5'-yl)-6-methyl-3,6-dihydro-2H-1,3,4-thiadiazin-2-one;

5-(7-chloro-3,3-dimethyl-2-oxoindolin-5-yl)-3,6-dihydro-2H-1,3,4-thiadiazin-2-one;

5-(7-chloro-2-oxoindolin-5-yl)-6-methyl-3,6-dihydro-2H-1,3,4-thiadiazin-2-one;

5-(7-bromo-3,3-dimethyl-2-oxoindolin-5-yl)-3,6-dihydro-2H-1,3,4-thiadiazin-2-one;

6-methyl-5-(9-methyl-2-oxo-2,3,4,5-tetrahydro-1H-benzo[b]azepin-7-yl)-3,6-dihydro-2H-1,3,4-thiadiazin-2-one;

5-(7-fluoro-3,3-dimethyl-2-oxoindolin-5-yl)-6-methyl-3,6-dihydro-2H-1,3,4-thiadiazin-2-one;

5-(7-chloro-3,3-dimethyl-2-oxoindolin-5-yl)-6-methyl-3,6-dihydro-2H-1,3,4-thiadiazin-2-one;

5-(7-bromo-3,3-dimethyl-2-oxoindolin-5-yl)-6-methyl-3,6-dihydro-2H-1,3,4-thiadiazin-2-one;

5-(6-methyl-2-oxo-3,6-dihydro-2H-1,3,4-thiadiazin-5-yl)-2-oxoindoline-7-carbonitrile;

(S)-5-(7-fluoro-2-oxoindolin-5-yl)-6-methyl-3,6-dihydro-2H-1,3,4-thiadiazin-2-one;

5-(7-chloro-3,3-dimethyl-2-oxoindolin-5-yl)-1, 3-dihydro-2H-pyrrolo[2,3-b]pyridin-2-one; and 7-chloro-3,3-dimethyl-5-(pyrimidin-5-yl) indolin-2-one, stereoisomers thereof, and veterinary acceptable salts thereof.

4. The compound of claim 3 that is a compound selected from the group consisting of:

6-(2-(1-(4-methoxyphenyl)cyclopropyl)-1H-benzo[d]imidazol-6-yl)-5-methyl-4,5-dihydropyridazin-3(2H)-one;

7-bromo-3,3-dimethyl-5-(4-methyl-6-oxo-1,4,5,6-tetrahydropyridazin-3-yl) indolin-2-one;

7-chloro-3,3-dimethyl-5-(4-methyl-6-oxo-1,4,5,6-tetrahydropyridazin-3-yl) indolin-2-one;

5-(7-fluoro-2-oxoindolin-5-yl)-6-methyl-3,6-dihydro-2H-1,3,4-thiadiazin-2-one;

5-(7-chloro-3,3-dimethyl-2-oxoindolin-5-yl)-3,6-dihydro-2H-1,3,4-thiadiazin-2-one;

5-(7-chloro-2-oxoindolin-5-yl)-6-methyl-3,6-dihydro-2H-1,3,4-thiadiazin-2-one;

6-methyl-5-(9-methyl-2-oxo-2,3,4,5-tetrahydro-1H-benzo[b]azepin-7-yl)-3,6-dihydro-2H-1,3,4-thiadiazin-2-one;

5-(7-fluoro-3,3-dimethyl-2-oxoindolin-5-yl)-6-methyl-3,6-dihydro-2H-1,3,4-thiadiazin-2-one;

5-(7-chloro-3,3-dimethyl-2-oxoindolin-5-yl)-6-methyl-3,6-dihydro-2H-1,3,4-thiadiazin-2-one;

5-(7-bromo-3,3-dimethyl-2-oxoindolin-5-yl)-6-methyl-3,6-dihydro-2H-1,3,4-thiadiazin-2-one; and 7-chloro-3,3-dimethyl-5-(pyrimidin-5-yl)indolin-2-one, stereoisomers thereof, and veterinary acceptable salts thereof.

5. The compound of claim 4 that is selected from the group consisting of 6-(2-(1-(4-methoxyphenyl)cyclopropyl)-1H-benzo[d]imidazol-6-yl)-5-methyl-4,5-dihydropyridazin-3(2H)-one;

5-(7-fluoro-2-oxoindolin-5-yl)-6-methyl-3,6-dihydro-2H-1,3,4-thiadiazin-2-one;

5-(7-chloro-3,3-dimethyl-2-oxoindolin-5-yl)-3,6-dihydro-2H-1,3,4-thiadiazin-2-one;

5-(7-chloro-2-oxoindolin-5-yl)-6-methyl-3,6-dihydro-2H-1,3,4-thiadiazin-2-one; and 6-methyl-5-(9-methyl-2-oxo-2,3,4,5-tetrahydro-1H-benzo[b]azepin-7-yl)-3,6-dihydro-2H-1,3,4-thiadiazin-2-one, stereoisomers thereof, and veterinary acceptable salts thereof.

6. The compound of claim 4 that is selected from the group consisting of 7-bromo-3,3-dimethyl-5-(4-methyl-6-oxo-1,4,5,6-tetrahydropyridazin-3-yl) indolin-2-one;

7-chloro-3,3-dimethyl-5-(4-methyl-6-oxo-1,4,5,6-tetrahydropyridazin-3-yl) indolin-2-one;

5-(7-fluoro-3,3-dimethyl-2-oxoindolin-5-yl)-6-methyl-3,6-dihydro-2H-1,3,4-thiadiazin-2-one;

5-(7-chloro-3,3-dimethyl-2-oxoindolin-5-yl)-6-methyl-3,6-dihydro-2H-1,3,4-thiadiazin-2-one;

5-(7-bromo-3,3-dimethyl-2-oxoindolin-5-yl)-6-methyl-3,6-dihydro-2H-1,3,4-thiadiazin-2-one; and 7-chloro-3,3-dimethyl-5-(pyrimidin-5-yl)indolin-2-one, stereoisomers thereof, and veterinary acceptable salts thereof.

7. The compound of claim 4 that is selected from the group consisting of 6-(2-(1-(4-methoxyphenyl)cyclopropyl)-1H-benzo[d]imidazol-6-yl)-5-methyl-4,5-dihydropyridazin-3(2H)-one;

7-bromo-3,3-dimethyl-5-(4-methyl-6-oxo-1,4,5,6-tetrahydropyridazin-3-yl)indolin-2-one;

7-chloro-3,3-dimethyl-5-(4-methyl-6-oxo-1,4,5,6-tetrahydropyridazin-3-yl)indolin-2-one;

5-(7-fluoro-2-oxoindolin-5-yl)-6-methyl-3,6-dihydro-2H-1,3,4-thiadiazin-2-one;

5-(7-chloro-2-oxoindolin-5-yl)-6-methyl-3,6-dihydro-2H-1,3,4-thiadiazin-2-one; and 5-(7-chloro-3,3-dimethyl-2-oxoindolin-5-yl)-6-methyl-3,6-dihydro-2H-1,3,4-thiadiazin-2-one, stereoisomers thereof, and veterinary acceptable salts thereof.

8. The compound of claim 7 that is 6-(2-(1-(4-methoxyphenyl)cyclopropyl)-1H-benzo[d]imidazol-6-yl)-5-methyl-4,5-dihydropyridazin-3(2H)-one, stereoisomers thereof, and veterinary acceptable salts thereof.

9. The compound of claim 7 that is 7-bromo-3,3-dimethyl-5-(4-methyl-6-oxo-1,4,5,6-tetrahydropyridazin-3-yl) indolin-2-one, stereoisomers thereof, and veterinary acceptable salts thereof.

10. The compound of claim 7 that is 7-chloro-3,3-dimethyl-5-(4-methyl-6-oxo-1,4,5,6-tetrahydropyridazin-3-yl) indolin-2-one, stereoisomers thereof, and veterinary acceptable salts thereof.

11. The compound of claim 7 that is 5-(7-fluoro-2-oxoindolin-5-yl)-6-methyl-3,6-dihydro-2H-1,3,4-thiadiazin-2-one; stereoisomers thereof, and veterinary acceptable salts thereof.

12. The compound of claim 7 that is 5-(7-chloro-2-oxoindolin-5-yl)-6-methyl-3,6-dihydro-2H-1,3,4-thiadiazin-2-one; and stereoisomers thereof, and veterinary acceptable salts thereof.

13. The compound of claim 7 that is 5-(7-chloro-3,3-dimethyl-2-oxoindolin-5-yl)-6-methyl-3,6-dihydro-2H-1,3,4-thiadiazin-2-one, stereoisomers thereof, and veterinary acceptable salts thereof.

14. A composition comprising a compound of claim 1, stereoisomer thereof, or a veterinary acceptable salt thereof.

15. The composition of claim 14, wherein the compound is selected from the group selected from 6-(2-(1-(4-methoxyphenyl)cyclopropyl)-1H-benzo[d]imidazol-6-yl)-5-methyl-4,5-dihydropyridazin-3(2H)-one;

7-bromo-3,3-dimethyl-5-(4-methyl-6-oxo-1,4,5,6-tetrahydropyridazin-3-yl) indolin-2-one;

7-chloro-3,3-dimethyl-5-(4-methyl-6-oxo-1,4,5,6-tetrahydropyridazin-3-yl) indolin-2-one;

5-(7-fluoro-2-oxoindolin-5-yl)-6-methyl-3,6-dihydro-2H-1,3,4-thiadiazin-2-one;

5-(7-chloro-3,3-dimethyl-2-oxoindolin-5-yl)-3,6-dihydro-2H-1,3,4-thiadiazin-2-one;

5-(7-chloro-2-oxoindolin-5-yl)-6-methyl-3,6-dihydro-2H-1,3,4-thiadiazin-2-one;

6-methyl-5-(9-methyl-2-oxo-2,3,4,5-tetrahydro-1H-benzo[b]azepin-7-yl)-3,6-dihydro-2H-1,3,4-thiadiazin-2-one;

5-(7-fluoro-3,3-dimethyl-2-oxoindolin-5-yl)-6-methyl-3,6-dihydro-2H-1,3,4-thiadiazin-2-one;

5-(7-chloro-3,3-dimethyl-2-oxoindolin-5-yl)-6-methyl-3,6-dihydro-2H-1,3,4-thiadiazin-2-one;

5-(7-bromo-3,3-dimethyl-2-oxoindolin-5-yl)-6-methyl-3,6-dihydro-2H-1,3,4-thiadiazin-2-one; and 7-chloro-3,3-dimethyl-5-(pyrimidin-5-yl) indolin-2-one, stereoisomers thereof, and veterinary acceptable salts thereof.

16. The composition of claim 14, further comprising a veterinary acceptable excipient.

17. The composition of claim 16, wherein the composition is administered orally.

18. The composition of claim 14, wherein the composition further comprises an additional pharmaceutical agent selected from the group consisting of an ACE inhibitor, furosemide or a spironolactone.

19. A method of treating an animal with myxomatous mitral valve disease, congestive heart failure and/or asymptomatic heart failure, by administering a therapeutic amount of a compound of claim 1, stereoisomer thereof, or veterinary acceptable salt thereof, to an animal in need thereof.

20. The method of claim 19, wherein the animal is co-administered an additional pharmaceutical agent selected from the group consisting of an ACE inhibitor, furosemide or a spironolactone.

* * * * *